US012668644B2

(12) United States Patent
Buelow et al.

(10) Patent No.: US 12,668,644 B2
(45) Date of Patent: Jun. 30, 2026

(54) ANTIBODY-BASED METHOD TO IDENTIFY, PURIFY, AND MANIPULATE CELL TYPES AND PROCESSES

(71) Applicant: Albert Einstein College of Medicine, Bronx, NY (US)

(72) Inventors: Hannes E. Buelow, Bronx, NY (US); Ulrich G. Steidl, New Rochelle, NY (US); Steven C. Almo, Pelham, NY (US); Robert A. Townley, Shorewood, WI (US); Richard Pisczcaztowski, Rutherford, NJ (US); Ron Seidel, III, Bronx, NY (US); Sriram Sundaravel, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 1201 days.

(21) Appl. No.: 17/612,665

(22) PCT Filed: May 26, 2020

(86) PCT No.: PCT/US2020/034522
§ 371 (c)(1),
(2) Date: Nov. 19, 2021

(87) PCT Pub. No.: WO2020/243078
PCT Pub. Date: Dec. 3, 2020

(65) Prior Publication Data
US 2022/0227886 A1 Jul. 21, 2022

Related U.S. Application Data

(60) Provisional application No. 62/853,881, filed on May 29, 2019.

(51) Int. Cl.
| | |
|---|---|
| *C07K 16/44* | (2006.01) |
| *A61K 47/68* | (2017.01) |
| *A61K 49/00* | (2006.01) |
| *G01N 33/569* | (2006.01) |

(52) U.S. Cl.
CPC .......... *C07K 16/44* (2013.01); *A61K 47/6815* (2017.08); *A61K 47/6835* (2017.08); *A61K*

*49/0058* (2013.01); *G01N 33/56966* (2013.01); *G01N 2400/40* (2013.01)

(58) Field of Classification Search
None
See application file for complete search history.

(56) References Cited

U.S. PATENT DOCUMENTS

2017/0080101 A1 * 3/2017 Dixon .................. C07K 14/475

FOREIGN PATENT DOCUMENTS

WO WO-2011094584 A2 * 8/2011 ............... C07K 1/22

OTHER PUBLICATIONS

GyÃ¶rgy, et al (2008) (Natural autoantibodies reactive with glycosaminoglycans in rheumatoid arthritis. Arthritis Res Ther 10, R110, 2008) teaches (Year: 2008).*
Williamson et al (Efficient N-Terminal Labeling of Proteins by Use of Sortase; Protein Modification; Angew Chem Int Ed Engl. Sep. 10, 2012;51(37):9377-80) (Year: 2012).*
Tomlinson et al (Cell separation: Terminology and practical considerations. J Tissue Eng. 2012). (Year: 2012).*
Caterson, "Fell-Muir Lecture: Chondroitin sulphate glycosaminoglycans: fun for some and confusion for others", International Journal of Experimental Pathology, Feb. 2012, vol. 93, No. 1, p. 1-10.
International Search Report and Written Opinion mailed Sep. 4, 2020, for related International Application No. PCT/US20/34522, 11 pages.

* cited by examiner

*Primary Examiner* — Gregory S Emch
*Assistant Examiner* — Sarah A Alsomairy
(74) *Attorney, Agent, or Firm* — Fox Rothschild LLP

(57) ABSTRACT

This disclosure relates to compositions and methods of identifying, isolating, and modulating cells and tissues based on their cellular glycosaminoglycan pattern. In some aspects, provided are anti-GAG motif antibodies or antigen-binding fragments thereof and their use for determining a glycosaminoglycan (GAG) glycotype for a cell. Also provided are methods of isolating cells, identifying cells, detecting a disease or disorder, and/or treating a disease or disorder based on a cellular glycotype.

10 Claims, 19 Drawing Sheets

Specification includes a Sequence Listing.

1

ANTIBODY-BASED METHOD TO IDENTIFY, PURIFY, AND MANIPULATE CELL TYPES AND PROCESSES

CROSS-REFERENCE TO RELATED APPLICATIONS

This application is a National Stage Application under 35 U.S.C. § 371 of International Application No. PCT/US20/34522 filed May 26, 2020, which claims the benefit of U.S. Provisional Application 62/853,881 filed on May 29, 2019. The entire contents of these applications are incorporated herein by reference in their entirety.

STATEMENT REGARDING FEDERALLY SPONSORED RESEARCH

This invention was made with government support under U01GM094665, U54GM094662, RC1GM090825, and U01CA241981, awarded by the National Institutes of Health (NIH). The government has certain rights in the invention.

REFERENCE TO A SEQUENCE LISTING

This application contains a Sequence Listing, which has been submitted electronically in ASCII format and is hereby incorporated by reference in its entirety. Said ASCII copy, created on Oct. 13, 2025, is named 182219-00145_ST25.txt and is 120,388 bytes in size.

FIELD OF THE INVENTION

The invention relates to compositions and methods of identifying, isolating, and modulating cells and tissues based on their cellular glycosaminoglycan pattern.

BACKGROUND

The surface characteristics of cells in multicellular organisms are a direct reflection of their function. Sensitive methods for detecting and defining the unique surface characteristics of cells offer great opportunities for gaining new mechanistic insights and developing new therapeutic strategies. Glycosaminoglycans (GAG) such as heparan sulfates (HS) or chondroitin/dermatan sulfates (CS/DS) are ubiquitous on the cell surface of metazoans and are expressed with extraordinary temporal and spatial resolution. Since HS and CS/DS may be amongst the most diverse molecules in nature, they provide the potential to strongly discriminate between different cell types.

However, current analytical methods for HS and CS/DS glycan structure determination are expensive, technically challenging and often low resolution, thus limiting their discriminatory power and widespread use. Thus, novel tools to define structural characteristics of HS or CS/DS on the surface of cells and to use these characteristics to distinguish between cells for diagnostic and therapeutic applications are urgently needed.

SUMMARY OF THE INVENTION

The invention relates to anti-GAG motif binding agents, including, but not limited to anti-GAG motif antibodies and antigen binding fragments thereof, as well as method of using these anti-GAG motif binding agents thereof for the identification, isolation, and manipulation of cells and tissues based on cellular glycotypes.

In one aspect, provided is a method of identifying a glycosaminoglycan (GAG) glycotype for a cell, the method comprising:

(a) contacting the cell with one or more anti-GAG motif antibodies or antigen-binding fragments thereof, (b) assessing the binding of the one or more anti-GAG motif antibodies or antigen-binding fragments thereof to the cell; and (c) assigning a GAG glycotype to the cell based on binding of the one or more antibodies or antigen-binding fragments thereof to the cell.

In one aspect, provided is a method of isolating a target cell from a mixture of cells based on the target cell's GAG glycotype, the method comprising:

(a) contacting the mixture of cells with one or more anti-GAG motif antibodies or antigen-binding fragments thereof that bind to one or more GAG motifs on the surface of the target cell; and (b) separating the target cell from the cell mixture.

In one embodiment, the one or more anti-GAG motif antibodies or antigen-binding fragments thereof comprises an affinity tag. In one embodiment, the method further comprises a step of contacting the target cell bound to the one or more anti-GAG motif antibodies or antigen binding fragments thereof with a medium that has a higher affinity for the affinity tag than the remainder of the mixture or composition.

In one aspect, provided is a method of identifying a cell based on its GAG glycotype, the method comprising:

(a) contacting the cell to one or more anti-GAG motif antibodies or antigen-binding fragments thereof, (b) assessing the binding of the one or more anti-GAG motif antibodies or antigen-binding fragments thereof to the cell; and (c) comparing the binding of the one or more anti-GAG motif antibodies or antigen-binding fragments thereof to the cell to the binding of the one or more anti-GAG motif antibodies or antigen-binding fragments thereof to a reference cell.

In one aspect, provided is a method of detecting a disease or disorder in a subject, the method comprising:

(a) providing one or more cells derived from the subject;

(b) contacting the one or more cells with one or more anti-GAG motif antibodies or antigen binding fragments thereof, (c) measuring binding of the one or more anti-GAG motif antibodies or antigen binding fragments to the one or more cells; and (d) detecting the disease or disorder if binding of the one or more anti-GAG motif antibodies or antigen binding fragments to the one or more cells is detected.

In one aspect, provided is a method of detecting a disease or disorder in a subject, the method comprising:

(a) providing one or more cells derived from the subject;

(b) contacting the one or more cells with one or more anti-GAG motif antibodies or antigen binding fragments thereof, (c) measuring binding of the one or more anti-GAG motif antibodies or antigen binding fragments thereof to the one or more cells; and (d) detecting the disease or disorder if binding of the one or more anti-GAG motif antibodies or antigen binding fragments thereof to the one or more cells is not detected.

In some embodiments, the one or more cells are provided in a sample. In some embodiments, the sample is a blood, bone marrow, serum, plasma, urine, feces, or tissue biopsy sample.

In one aspect, provided is a method of monitoring the progression of a disease or disorder in a subject, the method comprising:

(a) providing one or more cells derived from the subject;

(b) contacting one or more cells with one or more anti-GAG motif antibodies or antigen binding fragments thereof, (c) measuring binding of the one or more anti-GAG motif antibodies or antigen binding fragments thereof to the one or more cells; and (d) comparing the binding of the one or more anti-GAG motif antibodies or antigen binding fragments thereof to the one or more cells with the binding of the one or more anti-GAG motif antibodies or antigen binding fragments thereof to one or more cells obtained from the same patient at an earlier time.

In one aspect, provided is a method of treating and/or preventing a disease in a subject in need thereof, the method comprising administering to the subject an effective amount of one or more anti-GAG motif antibodies or antigen binding fragments thereof, wherein at least one anti-GAG motif antibody or antigen binding fragments thereof is conjugated to a therapeutic moiety, and wherein the one or more anti-GAG motif antibodies or antigen binding fragments thereof bind to one or more GAG motifs on the surface of the target cell or target tissue. In some embodiments, at least one of the one or more GAG motif antibodies or antigen-binding fragments thereof is conjugated to a detectable moiety. In some embodiments, the detectable moiety is fluorescent.

In some embodiments of the methods disclosed herein, at least one of the one or more GAG motif antibodies or antigen-binding fragments thereof is conjugated to an affinity tag.

In some embodiments of the methods disclosed herein, at least one of the one or more GAG motif antibodies or antigen-binding fragments thereof is conjugated to a magnetic moiety.

In some embodiments of the methods disclosed herein, at least one of the one or more GAG motif antibodies or antigen-binding fragments thereof is conjugated to a Sortase motif.

In one aspect, provided is a method of delivering a payload to a target cell based on the target cell's glycotype, the method comprising contacting a cell with an anti-GAG motif antibody or antigen binding fragment thereof, wherein the anti-GAG motif antibody or antigen-binding fragment thereof is conjugated to the payload and wherein the anti-GAG motif antibody or antigen-binding fragment thereof bind to one or more GAG motifs on the surface of the target cell.

BRIEF DESCRIPTION OF THE FIGURES

FIG. 1 illustrates the organization of a heparan sulfate (HS) glycan chain (FIG. 1A) and HS disaccharide (FIG. 1).

FIG. 2 illustrates that anti-GAG motif scFvs expressed on the surface of reporter cells can be used to glycotype cell lines by measuring cell-cell interactions.

FIG. 3 illustrates the concept of "glycotyping".

FIG. 5 illustrates that anti-HS motif antibodies or antigen binding fragments can be used to characterize primary hematopoietic cell lineages.

FIG. 7 illustrates that anti-HS motif antibodies can be used to identify functionally distinct cell populations that cannot be distinguished based on the existing CD system.

FIG. 8 illustrates conserved HS scFv patterning within human megakaryocyte and erythroid differentiation. FIG.

8A shows representative FACS density plot (upper panel) and morphology (lower panel) of human CD34$^+$ cells.

FIG. 10 illustrates HS modification alteration of the TF-1 cell line upon erythroid and megakaryocyte differentiation.

DETAILED DESCRIPTION OF THE INVENTION

The invention relates to anti-glycosaminoglycans (GAG) motif antibodies and antigen binding fragments thereof as well as method of using these antibodies and antigen binding fragments thereof for the identification, isolation, and manipulation of cells and tissues based on cellular glycotypes.

After binding of anti-GAG motif antibodies or antigen binding fragments thereof to cells, the cells remain intact and alive, allowing isolation, downstream analysis and manipulation of the isolated cells. Conversely, conjugation of anti-GAG motif antibodies or antigen binding fragments to cytotoxic agents allows targeted killing of undesired and/or pathogenic cells.

The surface characteristics of cells in multicellular organisms are a direct reflection of their function within the organism and are often used to classify them. Sensitive methods for detecting and defining novel or unique cell surface features at "higher resolution" and with greater dynamic precision could offer great mechanistic insight and therapeutic potential for the detection of malignancies and development of novel therapeutic approaches. For example, the cluster of differentiation (CD) marker system has revolutionized characterization, isolation, and targeting of hematopoietic, and many other cells. However, the number of reliable CD markers to isolate or target specific and homogenous cell types, and the resolution of separation of different cell types, widely varies between markers used and cell populations studied.

Figure 1A:
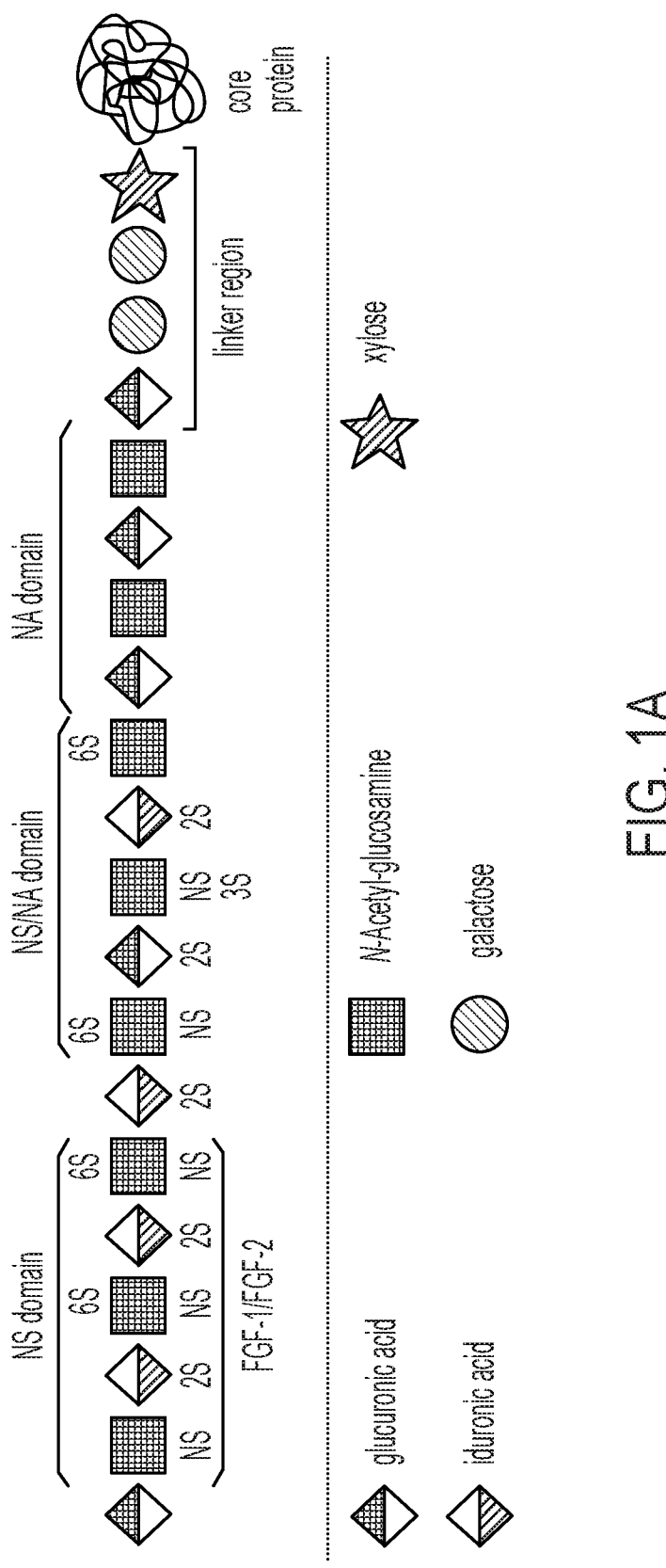
In FIG. 1A, HS domain structure is indicated (NS, N-sulfated; NS/NA, N-sulfated/acetylated; NA, N-acetylated) as well as putative protein binding motifs (e.g. FGF-1). HS is attached to core proteins via a tetrasaccharide linker region.
Figure 1B:
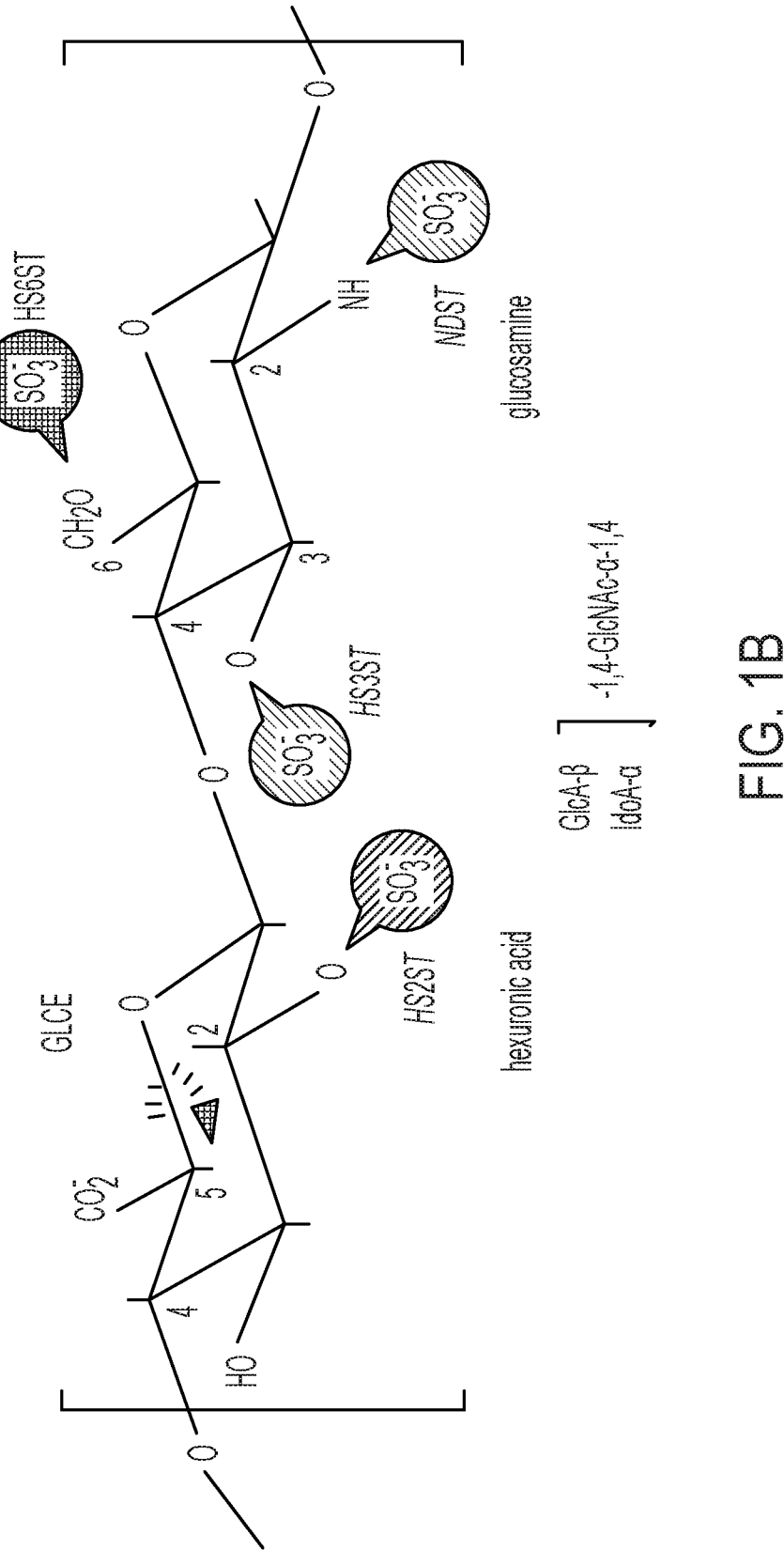
In FIG. 1B, a characteristic HS disaccharide is shown as well as the linkages that connect them. Gene names of enzymes that introduce various HS modifications are shown. GLCE, HS C5-glucuronyl-epimerase; HS6ST, HS 6-O-sulfotransferase; HS2ST, HS 2-O-sulfotransferase; HS3ST, HS 3-O-sulfotransferase; NDST, N-deacetylase-N-sulfotransferase.

GAGs such as heparan sulfate (HS) are ubiquitous, essential glycans, which are invariably attached to proteins (to form e.g. HS proteoglycans (HSPG)) and, are common to all cellular surfaces in multicellular organisms. HS glycans comprise long, unbranched polymers of disaccharides (glucuronic/iduronic acid—N-Acetyl-glucosamine for HS (see FIG. 1) and contribute to a multitude of functions in metazoan development, homeostasis, microbial infection, and immunity. An evolutionarily conserved network of HS modifying enzymes catalyzes the partial modification of the HS glycan polymer by de-acetylation, epimerization and sulfation (see FIG. 1). As a consequence, HS are often described as the most chemically and physically complex macromolecules in nature. Genetic and biochemical evidence demonstrate that many functions of HSPGs are controlled by specific HS modification patterns. These modification patterns are characteristic of specific cell and tissue types and states, and govern a wide spectrum of glycan-protein interactions.

The above said applies also to chondroitin/dermatan sulfate (CS/DS), which differs from HS only in that glucosamine is replaced by galactosamine. A conceptually similar, but molecularly distinct set of modification enzymes modifies CS/DS in various positions along the glycan chains to create a comparable molecular diversity.

GAG Glycotype

In one aspect, disclosed herein are methods of determining the GAG glycotype of a cell, a cell type and/or a tissue. As used herein, a "GAG glycotype", or short, "glycotype" is a classification system that classifies cells or tissues based on their binding to one or more antibodies or antigen-binding fragments thereof that bind to HS motifs or CS/DS motifs. As such, the GAG glycotype is a characterization of the sum of HS and CS/DS cell surface characteristics.

In one aspect, provided are antibodies or antigen-binding fragments thereof that recognize GAG motifs (such as a HS motif or a CS/DS motif) and that can be used for determining a GAG glycotype. As used herein, an "HS motif" is a combination of different HS modifications that are spatially arranged along a glycan chain attached to a protein on a cell's surface to provide a binding motif (antigen) for an anti-HS-motif-antibody or antigen-binding fragment thereof. As used herein, a "CS/DS motif" is a combination of different CS/DS modifications that are spatially arranged along a glycan chain attached to a protein on a cell's surface to provide a binding motif (antigen) for an anti-CS-motif-antibody or antigen-binding fragment thereof. In vivo, some HS motifs appear quite common and are widely distributed across tissues, whereas others seem less common, and can be as rare as single cell-specific in the nematode *C. elegans*.

Antibodies and Antibody Fragments that Bind to GAG Motifs

In one aspect, provided are antibodies or antigen-binding fragments thereof that bind to GAG motifs. In some embodiments, the anti-GAG motif antibodies or antigen-binding fragments thereof bind to an HS motif. In some embodiments, the anti-GAG motif antibodies or antigen-binding fragments thereof bind to a CS/DS motif.

In some embodiments, the anti-GAG motif antibody or antigen-binding fragment thereof is an anti-HS motif antibody or an anti-CD/DS motif antibody in scFv format previously described, see Table 1 and Table 2. For a limited number of scFvs listed in Table 1, individual HS modifications required for binding have been determined in vitro and in vivo.

TABLE 1

Selected anti-HS motif antibodies(scFv format). Indicated are individual anti-HS motif antibodies (in scFv format), the parental heavy chain from the antibody is derived from, the sequence of heavy chain CDR3 (CDR3H), known HS modification that are part of the HS motif recognized by the indicated antibody, and the corresponding scientific reference (Ref). "+" = required. "−" = not required. in. = inhibitory. (+) = partially required. # control antibody shown to not bind to HS. NAc = N-acetylated glucosamine. NS = N-sulfated glucosamine. C5 = C5-epimerization. 2S = 2-O-sulfation. 6S = 6-O-sulfation. 3S = 3-O-sulfation. [1] Dennissen et al (2002). J Biol Chem 277, 10982-10986. [2] Attreed et al (2012). Nat Methods 9, 477-479. [3] van de Westerlo et al (2002). Blood 99, 2427-2433. [4] Attreed et al (2015). Methods Mol Biol 1229, 253-268. [5] Attreed et al (2016). Glycobiology 26, 862-870. [6] van Kuppevelt et al (1998). J Biol Chem 273, 12960-12966. [7] Smits, N.C., Lensen et al (2006). Methods Enzymol 416, 61-87. [8] Wijnhoven et al (2008). Glycoconj J 25, 177-185. [9] ten Dam et al (2004). J Biol Chem 279, 38346-38352. [10] Smits et al (2010). J Biol Chem 285, 41143-41151. [11] Jenniskens et al (2000). J Neurosci 20, 4099-4111.

| Antibody name | CDR3H sequence | Cellular HS modifications required for binding to antibody | | | | | | | | | Ref. |
| | | In vitro | | | | | | In vivo | | | |
| | | NAc | NS | C5 | 2S | 6S | 3S | 2S | 6S | 3S | |
| AO4B08 | SLRMNGWRAHQ | | + | + | + | + | | + | + | | [1, 2] |
| EV3B2 (EW4D2) | GKMKLNR | | + | + | + | + | | | | | [1, 3] |
| EV3C3 | GYRPRF | | | | | | | | | | [1] |
| EV3D1 | SISMNGVGVRIQ | + | + | | | (+) | (+) | | | | [1] |
| EW3D10 (EW3D3) | GRTVGRN | | + | | | + | | | | | [3] |
| EW3E4 | DRRNTQKTRYRT | | | | | | | | | | [3] |
| EW3F5 | SGRQARQGRFPK | | | | | | | | | | [3] |
| EW3G6 | GGTTRIRK | (+) | | | | | | + | in. | +/− | [3-5] |
| EW4A4 | GTKLKMTK | − | | | | | | + | + | + | [3-5] |
| EW4A11 | ERNTIRR | | | | | | | | | | [3] |
| EW4B5 | GRLHLPRK | | | | | | | | | | [3] |
| EW4B7 | SSSRHHRLHR | | | | | | | | | | [3] |
| EW4B10 | QRWKPAVTPKLV | | | | | | | | | | [3] |
| EW4C10 | ARMTGHVRNVMI | | | | | | | | | | [3] |
| EW4D5 | PVSHRKWRVTV | | | | | | | | | | [3] |
| EW4E1 | GRRHKLIR | | | | | | | | | | [3] |
| EW4E9 | LRGTKMFRH | | | | | | | | | | [3] |
| EW4E10 | SRKTPKPFMRK | | | | | | | | | | [3] |
| EW4G1 | GARLKR | | | | | | | | | | [3] |
| EW4G2 | GKVKLPN | | | | | | | | | | [3] |
| EW4G10 | GTKKLGK | | | | | | | | | | [3] |
| HS3A8 (EW3H12) | GMRPRL | | + | + | + | + | | + | + | | [1-3] |
| HS3B7 | SRKTRKPFMRK | + | + | + | in. | + | | | | | [1] |
| HS3G8 | YYHYKVN | | | | | | | | | | [6] |
| HS4A5 | WVTEP | | + | + | + | + | | | | | [1] |
| HS4C3 | GRRLKD | | + | (+) | + | + | + | (+) | + | + | [7] |
| HS4D4 | GMRPRL | | + | + | + | + | (+) | | | | [1] |
| HS4D10 | SLRMNGCGAHQ | | | | | | | | | | [6] |
| HS4E4 | HAPLRNTRTNT | + | + | + | + | in. | | | | | [1] |
| LKIV69 | GSRSSR | | + | + | + | | | | | | [8] |
| MW3G3 | QKKRPRF | + | | + | + | | | | | | [9] |
| NS4F5 | SGRKGRMR | + | | + | + | | | | | | [10] |
| RB4EA12 | RRYALDY | + | + | + | in. | + | | | | | [1] |
| AO4B05 | LKQQGIS | | | | | | | | | | [11] |
| AO4F12 | AMTQKKPRKLSL | | | | | | | | | | [11] |
| RB4EG12 | SGRKYFRARDMN | | | | | | | | | | [11] |
| MPB49 # | WRNDRQ | | | | | | | | | | [7] |

TABLE 2

Selected anti-CS motif antibodies (scFv format). Indicated are individual anti-CS motif antibodies (in scFv format), the parental heavy chain from the antibody is derived from, the sequence of heavy chain CDR3, and the corresponding scientific reference. [12] Smetsers et al (2004). J Invest Dermatol 122, 707-716. [13] Purushothaman et al (2007). J Biol Chem 282, 19442-19452.

| Antibody name | CDR3H sequence | Reference |
|---|---|---|
| IO3D9 | GIKHRHTQ | [12] |
| IO3H10 | AKRLDW | [12] |
| IO3H12 | MKTRLDV | [12] |
| IO4C2 | GKQRYS | [12] |
| GD3G7 | GRWTQMT | [13] |

Also provided are scFvs generated based on information available in the references listed in Tables 1 and Table 2 as well as references therein (e.g. Tomlinson et al., J. Mol. Biol. (1992), 227:776-798; Nissim et al., EMBO (1994), 13(3): 692-698; Marks et al., J. Mol. Biol. (1991) 222:581-597). The variable light chain of the scFvs was synthesized de novo based on the V$_{\lambda3}$-BSA sequence from Marks et al. (J. Mol. Biol. (1991) 222:581-597) and the linker on Huston et al. (PNAS (1988) 85:5879-5883). In some embodiments, the anti-GAG motif antibody or antigen-binding fragment thereof are scFvs and comprise one or more of the SEQ ID NOs:1-42. Variable heavy chains are indicated in bold and the variable light chain in regular font, respectively. The linker is underlined as follows: linker. Each heavy and light variable chain comprises three CDRs. The heavy chain CDRs are CDR1H, CDR2H, and CDR3H. The light chain CDRs are CDR1L, CDR2L, and CDR3L. The complementary regions are underlined as follows: CDR1, CDR2, and CDR3.

Anti-HS motif scFvs
(A04B08)

SEQ ID NO: 1

AMAEVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCARSLRMNG

WRAHQWGQGTLVTVSRGGGGSGGGGSGGGGSSELTQDPAVSVALGQTVRITCQG

DSLRSYYASWYQQKPGQAPVLVIYGKNNRPSGIPDRFSGSSSGNTASLTITGAQAEDE

ADYYCNSRDSSGNHVVFGGGTKLTVLGAAA (EV3B2, EW4D2)

SEQ ID NO: 2

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGK

MKLNRWGQGTLVTVSRGGGGSGGGGSGGGGSSELTQDPAVSVALGQTVRITCQG

DSLRSYYASWYQQKPGQAPVLVIYGKNNRPSGIPDRFSGSSSGNTASLTITGAQAEDE

ADYYCNSRDSSGNHVVFGGGTKLTVLGAAA (EV3C3)

SEQ ID NO: 3

AMAEVQLVESGGGLIQPGGSLRLSCAASGFTVSSNYMSWVRQAPGKGLEWVSV

IYSGGSTYYADSVKGRFTISRDNSKNTLYLQMNSLRAEDTAVYYCARGYRPRFW

GQGTLVTVSRGGGGSGGGGSGGGGSSELTQDPAVSVALGQTVRITCQGDSLRSYYA

SWYQQKPGQAPVLVIYGKNNRPSGIPDRFSGSSSGNTASLTITGAQAEDEADYYCNS

RDSSGNHVVFGGGTKLTVLGAAA

-continued (EV3D1)

SEQ ID NO: 4

AMAEVQLLESGGGLVQPGGSLRLSCAASGFTFSSYAMSWVRQAPGKGLEWVSA

ISGSGGGSTYYADSVKGRFTISRDNSKNTLYLQMNSLRAEDTAVYYCARSISMNGV

GVRIQWGQGTLVTVSRGGGGSGGGGSGGGGSSELTQDPAVSVALGQTVRITCQGD

SLRSYYASWYQQKPGQAPVLVIYGKNNRPSGIPDRFSGSSSGNTASLTITGAQAEDEA

DYYCNSRDSSGNHVVFGGGTKLTVLGAAA (EW3D10, EW3D3)

SEQ ID NO: 5

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGRT

VGRNWGQGTLVTVSRGGGGSGGGGSGGGGSSELTQDPAVSVALGQTVRITCQGDS

LRSYYASWYQQKPGQAPVLVIYGKNNRPSGIPDRFSGSSSGNTASLTITGAQAEDEA

DYYCNSRDSSGNHVVFGGGTKLTVLGAAA (EW3E4)

SEQ ID NO: 6

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARDRR

NTQKTRYRTWGQGTLVTVSRGGGGSGGGGSGGGGSSELTQDPAVSVALGQTVRIT

CQGDSLRSYYASWYQQKPGQAPVLVIYGKNNRPSGIPDRFSGSSSGNTASLTITGAQ

AEDEADYYCNSRDSSGNHVVFGGGTKLTVLGAAA (EW3F5)

SEQ ID NO: 7

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARSGR

QARQGRFPKWGQGTLVTVSRGGGGSGGGGSGGGGSSELTQDPAVSVALGQTVRI

TCQGDSLRSYYASWYQQKPGQAPVLVIYGKNNRPSGIPDRFSGSSSGNTASLTITGAQ

AEDEADYYCNSRDSSGNHVVFGGGTKLTVLGAAA (EW3G6)

SEQ ID NO: 8

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGGT

TRIRKWGQGTLVTVSRGGGGSGGGGSGGGGSSELTQDPAVSVALGQTVRITCQGD

SLRSYYASWYQQKPGQAPVLVIYGKNNRPSGIPDRFSGSSSGNTASLTITGAQAEDEA

DYYCNSRDSSGNHVVFGGGTKLTVLGAAA

-continued (EW4A4)

SEQ ID NO: 9

AMAQVQLVQSGAEVKKPGASVKVSCKASGYTFTGYYMHWVRQAPGQGLEWM

GWINPNSGGTNYAQKFQGWVTMTRDTSISTAYMELSRLRSDDTAVYYCARGTK

LKMTKWGQGTLVTVSRGGGGSGGGGSGGGGSSELTQDPAVSVALGQTVRITCQG

DSLRSYYASWYQQKPGQAPVLVIYGKNNRPSGIPDRFSGSSSGNTASLTITGAQAEDE

ADYYCNSRDSSGNHVVFGGGTKLTVLGAAA (EW4A11)

SEQ ID NO: 10

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARERN

TIRRWGQGTLVTVSRGGGGSGGGGSGGGGSSELTQDPAVSVALGQTVRITCQGDS

LRSYYASWYQQKPGQAPVLVIYGKNNRPSGIPDRFSGSSSGNTASLTITGAQAEDEA

DYYCNSRDSSGNHVVFGGGTKLTVLGAAA (EW4B5)

SEQ ID NO: 11

AMAEVQLVESGGGLVQPGGSLRLSCAGSGFTFSSYAMHWVRQAPGKGLEWVS

AIGTGGGTYYADSVKGRFTISRDNAKNSLYLQMNSLRAEDTAVYYCARGRLHL

PRKWGQGTLVTVSRGGGGSGGGGSGGGGSSELTQDPAVSVALGQTVRITCQGDSL

RSYYASWYQQKPGQAPVLVIYGKNNRPSGIPDRFSGSSSGNTASLTITGAQAEDEAD

YYCNSRDSSGNHVVFGGGTKLTVLGAAA (EW4B7)

SEQ ID NO: 12

AMAQVQLVQSGAEVKKPGASVKVSCKASGYTFTGYYMHWVRQAPGQGLEWM

GWINPNSGGTNYAQKFQGWVTMTRDTSISTAYMELSRLRSDDTAVYYCARSSS

RHHRLHRWGQGTLVTVSRGGGGSGGGGSGGGGSSELTQDPAVSVALGQTVRITC

QGDSLRSYYASWYQQKPGQAPVLVIYGKNNRPSGIPDRFSGSSSGNTASLTITGAQA

EDEADYYCNSRDSSGNHVVFGGGTKLTVLGAAA (EW4B10)

SEQ ID NO: 13

AMAQVQLVQSGAEVKKPGASVKVSCKASGYTFTSYAMHWVRQAPGQRLEWM

GWINAGNGNTKYSQKFQGRVTITRDTSASTAYMELSSLRSEDTAVYYCARQRW

KPAVTPKLVWGQGTLVTVSRGGGGSGGGGSGGGGSSELTQDPAVSVALGQTVRIT

CQGDSLRSYYASWYQQKPGQAPVLVIYGKNNRPSGIPDRFSGSSSGNTASLTITGAQ

AEDEADYYCNSRDSSGNHVVFGGGTKLTVLGAAA

-continued (EW4C10)

SEQ ID NO: 14

AMAEVQLVESGGGLVQPGGSLRLSCAGSGFTFSSYAMHWVRQAPGKGLEWVS

AIGTGGGTYYADSVKGRFTISRDNAKNSLYLQMNSLRAEDTAVYYCARARMTG

HVRNVMIWGQGTLVTVSRGGGGSGGGGSGGGGSSELTQDPAVSVALGQTVRITCQ

GDSLRSYYASWYQQKPGQAPVLVIYGKNNRPSGIPDRFSGSSSGNTASLTITGAQAE

DEADYYCNSRDSSGNHVVFGGGTKLTVLGAAA (EW4D5)

SEQ ID NO: 15

AMAEVQLVESGGGLVQPGGSLRLSCAGSGFTFSSYAMHWVRQAPGKGLEWVS

AIGTGGGTYYADSVKGRFTISRDNAKNSLYLQMNSLRAEDTAVYYCARPVSHRK

WRVTVWGQGTLVTVSRGGGGSGGGGSGGGGSSELTQDPAVSVALGQTVRITCQG

DSLRSYYASWYQQKPGQAPVLVIYGKNNRPSGIPDRFSGSSSGNTASLTITGAQAEDE

ADYYCNSRDSSGNHVVFGGGTKLTVLGAAA (EW4E1)

SEQ ID NO: 16

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGRR

HKLIRWGQGTLVTVSRGGGGSGGGGSGGGGSSELTQDPAVSVALGQTVRITCQGD

SLRSYYASWYQQKPGQAPVLVIYGKNNRPSGIPDRFSGSSSGNTASLTITGAQAEDEA

DYYCNSRDSSGNHVVFGGGTKLTVLGAAA (EW4E9)

SEQ ID NO: 17

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARLRG

TKMFRHWGQGTLVTVSRGGGGSGGGGSGGGGSSELTQDPAVSVALGQTVRITCQ

GDSLRSYYASWYQQKPGQAPVLVIYGKNNRPSGIPDRFSGSSSGNTASLTITGAQAE

DEADYYCNSRDSSGNHVVFGGGTKLTVLGAAA (EW4E10)

SEQ ID NO: 18

AMAQVQLVQSGAEVKKPGATVKISCKVSGYTFTDYYMHWVQQAPGKGLEWM

GLVDPEDGETIYAEKFQGRVTITADTSTDTAYMELSSLRSEDTAVYYCARSRKTP

KPFMRKWGQGTLVTVSRGGGGSGGGGSGGGGSSELTQDPAVSVALGQTVRITCQ

GDSLRSYYASWYQQKPGQAPVLVIYGKNNRPSGIPDRFSGSSSGNTASLTITGAQAE

DEADYYCNSRDSSGNHVVFGGGTKLTVLGAAA

-continued (EW4G1)

SEQ ID NO: 19

AMAEVQLVESGGGLIQPGGSLRLSCAASGFTVSSNYMSWVRQAPGKGLEWVSV

IYSGGSTYYADSVKGRFTISRDNSKNTLYLQMNSLRAEDTAVYYCARGARLKR

WGQGTLVTVSRGGGGSGGGGSGGGGSSELTQDPAVSVALGQTVRITCQGDSLRSY

YASWYQQKPGQAPVLVIYGKNNRPSGIPDRFSGSSSGNTASLTITGAQAEDEADYYC

NSRDSSGNHVVFGGGTKLTVLGAAA (EW4G2)

SEQ ID NO: 20

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGK

VKLPNGQGTLVTVSRGGGGSGGGGSGGGGSSELTQDPAVSVALGQTVRITCQGD

SLRSYYASWYQQKPGQAPVLVIYGKNNRPSGIPDRFSGSSSGNTASLTITGAQAEDEA

DYYCNSRDSSGNHVVFGGGTKLTVLGAAA (EW4G10)

SEQ ID NO: 21

AMAEVQLVESGGGLVQPGGSLRLSCAGSGFTFSSYAMHWVRQAPGKGLEWVS

AIGTGGGTYYADSVKGRFTISRDNAKNSLYLQMNSLRAEDTAVYYCARGTKKL

GKWGQGTLVTVSRGGGGSGGGGSGGGGSSELTQDPAVSVALGQTVRITCQGDSLR

SYYASWYQQKPGQAPVLVIYGKNNRPSGIPDRFSGSSSGNTASLTITGAQAEDEADY

YCNSRDSSGNHVVFGGGTKLTVLGAAA (HS3A8, EW3H12)

SEQ ID NO: 22

AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGM

RPRLWGQGTLVTVSRGGGGSGGGGSGGGGSSELTQDPAVSVALGQTVRITCQGDS

LRSYYASWYQQKPGQAPVLVIYGKNNRPSGIPDRFSGSSSGNTASLTITGAQAEDEA

DYYCNSRDSSGNHVVFGGGTKLTVLGAAA (HS3B7)

SEQ ID NO: 23

AMAQVQLVQSGAEVKKPGATVKISCKVSGYTFTDYYMHWVQQAPGKGLEWM

GLVDPEDGETIYAEKFQGRVTITADTSTDTAYMELSSLRSEDTAVYYCARSRKT

RKPFMRKWGQGTLVTVSRGGGGSGGGGSGGGGSSELTQDPAVSVALGQTVRITC

QGDSLRSYYASWYQQKPGQAPVLVIYGKNNRPSGIPDRFSGSSSGNTASLTITGAQA

EDEADYYCNSRDSSGNHVVFGGGTKLTVLGAAA

-continued (HS3G8)
                                                                    SEQ ID NO: 24
AMAQVQLVQSGAEVKKPGASVKVSCKASGYTFTGYYMHWVRQAPGQGLEWM

GWINPNSGGTNYAQKFQGWVTMTRDTSISTAYMELSRLRSDDTAVYYCARYYH

YKVNWGQGTLVTVSRGGGGSGGGGSGGGGSSELTQDPAVSVALGQTVRITCQGDS

LRSYYASWYQQKPGQAPVLVIYGKNNRPSGIPDRFSGSSSGNTASLTITGAQAEDEA

DYYCNSRDSSGNHVVFGGGTKLTVLGAAA (HS4A5)
                                                                    SEQ ID NO: 25
AMAQVQLQESGPGLVKPSQTLSLTCTVSGGSISSGGYYWSWIRQHPGKGLEWI

GYIYYSGSTYYNPSLKSRVTISVDTSKNQFSLKLSSVTAADTAVYYCARWVTEPW

GQGTLVTVSRGGGGSGGGGSGGGGSSELTQDPAVSVALGQTVRITCQGDSLRSYYA

SWYQQKPGQAPVLVIYGKNNRPSGIPDRFSGSSSGNTASLTITGAQAEDEADYYCNS

RDSSGNHVVFGGGTKLTVLGAAA (HS4C3)
                                                                    SEQ ID NO: 26
AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGRR

LKDWGQGTLVTVSRGGGGSGGGGSGGGGSSELTQDPAVSVALGQTVRITCQGDSL

RSYYASWYQQKPGQAPVLVIYGKNNRPSGIPDRFSGSSSGNTASLTITGAQAEDEAD

YYCNSRDSSGNHVVFGGGTKLTVLGAAA (HS4D4)
                                                                    SEQ ID NO: 27
AMAEVQLVESGGGLVQPGGSLRLSCAASGFTFSSYEMNWVRQAPGKGLEWVS

YISSSGSTIYYADSVKGRFTISRDNAKNSLYLQMNSLRAEDTAVYYCARGMRPRL

WGQGTLVTVSRGGGGSGGGGSGGGGSSELTQDPAVSVALGQTVRITCQGDSLRSY

YASWYQQKPGQAPVLVIYGKNNRPSGIPDRFSGSSSGNTASLTITGAQAEDEADYYC

NSRDSSGNHVVFGGGTKLTVLGAAA (HS4D10)
                                                                    SEQ ID NO: 28
AMAEVQLVESGGGLIQPGGSLRLSCAASGFTVSSNYMSWVRQAPGKGLEWVSV

IYSGGSTYYADSVKGRFTISRDNSKNTLYLQMNSLRAEDTAVYYCARSLRMNGC

GAHQWGQGTLVTVSRGGGGSGGGGSGGGGSSELTQDPAVSVALGQTVRITCQGDS

LRSYYASWYQQKPGQAPVLVIYGKNNRPSGIPDRFSGSSSGNTASLTITGAQAEDEA

DYYCNSRDSSGNHVVFGGGTKLTVLGAAA (HS4E4)
                                                                    SEQ ID NO: 29
AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARHAP

LRNTRTNTWGQGTLVTVSRGGGGSGGGGSGGGGSSELTQDPAVSVALGQTVRITC

QGDSLRSYYASWYQQKPGQAPVLVIYGKNNRPSGIPDRFSGSSSGNTASLTITGAQA

EDEADYYCNSRDSSGNHVVFGGGTKLTVLGAAA (LKIV69)

SEQ ID NO: 30
AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARGSR

SSRWGQGTLVTVSRGGGGSGGGGSGGGGSSELTQDPAVSVALGQTVRITCQGDSL

RSYYASWYQQKPGQAPVLVIYGKNNRPSGIPDRFSGSSSGNTASLTITGAQAEDEAD

YYCNSRDSSGNHVVFGGGTKLTVLGAAA (MW3G3)

SEQ ID NO: 31
AMAEVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCARQKKRPR

FWGQGTLVTVSRGGGGSGGGGSGGGGSSELTQDPAVSVALGQTVRITCQGDSLRS

YYASWYQQKPGQAPVLVIYGKNNRPSGIPDRFSGSSSGNTASLTITGAQAEDEADYY

CNSRDSSGNHVVFGGGTKLTVLGAAA (NS4F5)

SEQ ID NO: 32
AMAEVQLVESGGGLVQPGGSLRLSCAASGFTFSSYWMHWVRQAPGKGLVWVS

RINSDGSSTTYADSVKGRFTISRDNAKNTLYLQMNSLRAEDTAVYYCARSGRKG

RMRWGQGTLVTVSRGGGGSGGGGSGGGGSSELTQDPAVSVALGQTVRITCQGDSL

RSYYASWYQQKPGQAPVLVIYGKNNRPSGIPDRFSGSSSGNTASLTITGAQAEDEAD

YYCNSRDSSGNHVVFGGGTKLTVLGAAA (RB4EA12)

SEQ ID NO: 33
AMAEVQLVESGGGVVRPGGSLRLSCAASGFTFDDYGMSWVRQAPGKGLEWVS

GINWNGGSTGYADSVKGRFTISRDNAKNSLYLQMNSLRAEDTAVYYCARRRYA

LDYWGQGTLVTVSRGGGGSGGGGSGGGGSSELTQDPAVSVALGQTVRITCQGDSL

RSYYASWYQQKPGQAPVLVIYGKNNRPSGIPDRFSGSSSGNTASLTITGAQAEDEAD

YYCNSRDSSGNHVVFGGGTKLTVLGAAA (AO4F12)

SEQ ID NO: 34
AMAQVQLVQSGAEVKKPGASVKVSCKASGYTFTSYYMHWVRQAPGQGLEWM

GIINPSGGSTSYAQKFQGRVTMTRDTSTSTVYMELSSLRSEDTAVYYCARAMTQ

-continued

KKPRKLSLWGQGTLVTVSRGGGGSGGGGSGGGGSSELTQDPAVSVALGQTVRITC

QGDSLRSYYASWYQQKPGQAPVLVIYGKNNRPSGIPDRFSGSSSGNTASLTITGAQA

EDEADYYCNSRDSSGNHVVFGGGTKLTVLGAAA (RB4EG12)

SEQ ID NO: 35
AMAQMQLVQSGAEVKKTGSSVKVSCKASGYTFTYRYLHWVRQAPGQALEWM

GWITPFNGNTNYAQKFQDRVTITRDRSMSTAYMELSSLRSEDTAMYYCARSGR

KYFRARDMNWGQGTLVTVSRGGGGSGGGGSGGGGSSELTQDPAVSVALGQTVRI

TCQGDSLRSYYASWYQQKPGQAPVLVIYGKNNRPSGIPDRFSGSSSGNTASLTITGAQ

AEDEADYYCNSRDSSGNHVVFGGGTKLTVLGAAA (AO4B05)

SEQ ID NO: 36
AMAEVQLVESGGGLVQPGGSLRLSCAASGFTFSSYWMHWVRQAPGKGLVWVS

RINSDGSSTTYADSVKGRFTISRDNAKNTLYLQMNSLRAEDTAVYYCARLKQQG

ISWGQGTLVTVSRGGGGSGGGGSGGGGSSELTQDPAVSVALGQTVRITCQGDSLRS

YYASWYQQKPGQAPVLVIYGKNNRPSGIPDRFSGSSSGNTASLTITGAQAEDEADYY

CNSRDSSGNHVVFGGGTKLTVLGAAA (MPB49)-control antibody, does not recognize HS motif

SEQ ID NO: 37
AMAEVQLVESGGGLVKPGGSLRLSCAASGFTFSNAWMSWVRQAPGKGLEWVG

RIKSKTDGGTTDYAAPVKGRFTISRDDSKNTLYLQMNSLKTEDTAVYYCARWR

NDRQWGQGTLVTVSRGGGGSGGGGSGGGGSSELTQDPAVSVALGQTVRITCQGDS

LRSYYASWYQQKPGQAPVLVIYGKNNRPSGIPDRFSGSSSGNTASLTITGAQAEDEA

DYYCNSRDSSGNHVVFGGGTKLTVLGAAA

Anti-CSmotifscFvs
(IO3D9)

SEQ ID NO: 38
QVQLVQSGAEVKKPGASVKVSCKASGYTFTSYYMHWVRQAPGQGLEWMGIIN

PSGGSTSYAQKFQGRVTMTRDTSTSTVYMELSSLRSEDTAVYYCARGIKHRHTQ

WGQGTLVTVSRGGGGSGGGGSGGGGSSELTQDPAVSVALGQTVRITCQGDSLRSY

YASWYQQKPGQAPVLVIYGKNNRPSGIPDRFSGSSSGNTASLTITGAQAEDEADYC

NSRDSSGNHVVFGGGTKLTVLGAAA (IO3H10)

SEQ ID NO: 39
QVQLVQSGAEVKKPGASVKVSCKASGYTFTSYYMHWVRQAPGQGLEWMGIIN

PSGGSTSYAQKFQGRVTMTRDTSTSTVYMELSSLRSEDTAVYYCARAKRLDWW

GQGTLVTVSRGGGGSGGGGSGGGGSSELTQDPAVSVALGQTVRITCQGDSLRSYYA

```
                         -continued
SWYQQKPGQAPVLVIYGKNNRPSGIPDRFSGSSSGNTASLTITGAQAEDEADYYCNS

RDSSGNHVVFGGGTKLTVLGAAA (IO3H12)
                                          SEQ ID NO: 40
QVQLVESGGGVVQPGRSLRLSCAASGFTFSSYAMHWVRQAPGKGLEWVAVISY

DGSNKYYADSVKGRFTISRDNSKNTLYLQMNSLRAEDTAVYYCARMKTRLDVW

GQGTLVTVSRGGGGSGGGGSGGGGSSELTQDPAVSVALGQTVRITCQGDSLRSYYA

SWYQQKPGQAPVLVIYGKNNRPSGIPDRFSGSSSGNTASLTITGAQAEDEADYYCNS

RDSSGNHVVFGGGTKLTVLGAAA (IO4C2)
                                          SEQ ID NO: 41
EVQLVESGGGLVQPGGSLRLSCAASGFTFSSYWMSWVRQAPGKGLEWVANIK

QDGSEKYYVDSVKGRFTISRDNAKNSLYLQMNSLRAEDTAVYYCARGKQRYSW

GQGTLVTVSRGGGGSGGGGSGGGGSSELTQDPAVSVALGQTVRITCQGDSLRSYYA

SWYQQKPGQAPVLVIYGKNNRPSGIPDRFSGSSSGNTASLTITGAQAEDEADYYCNS

RDSSGNHVVFGGGTKLTVLGAAA (GD3G7)
                                          SEQ ID NO: 42
EVQLVESGGGLVKPGGSLRLSCAASGFTFSNAWMSWVRQAPGKGLEWYGRIK

SKTDGGTTDYAAPVKGRFTISRDDSKNTLYLQMNSLKTEDTAVYYCARGRWTQ

MTWGQGTLVTVSRGGGGSGGGGSGGGGSSELTQDPAVSVALGQTVRITCQGDSLR

SYYASWYQQKPGQAPVLVIYGKNNRPSGIPDRFSGSSSGNTASLTITGAQAEDEADY

YCNSRDSSGNHVVFGGGTKLTVLGAAA
```

In some embodiments, the anti-GAG motif antibodies or antigen-binding fragments thereof disclosed herein comprise one, two, or three of the heavy and/or of the light chain CDRs of SEQ ID NOs:1-42. In some embodiments, the anti-GAG motif antibodies or antigen-binding fragments thereof disclosed herein comprise CDR1H, CDR2H, and CDR3H of any of SEQ ID NOs:1-42. In some embodiments, the anti-GAG motif antibodies or antigen-binding fragments thereof disclosed herein comprise CDR1L, CDR2L, and CDR3L of any of SEQ ID NOs:1-42. In some embodiments, the anti-GAG motif antibodies or antigen-binding fragments thereof disclosed herein comprise CDR1H, CDR2H, CDR3H, CDR1L, CDR2L, and CDR3L of any of SEQ ID NOs:1-42.

Based on the anti-GAG motif-antibodies or antigen-binding fragments thereof disclosed herein, it would be a routine matter for those skilled in the art to design and produce additional anti-GAG motif-antibodies or antigen-binding fragments thereof for use in the present methods by, e.g., designing and producing additional anti-GAG motif-antibodies that comprise the variable region sequences and/or CDRs of the anti-GAG motif-antibodies disclosed herein. Moreover, it would be a routine matter to design additional anti-GAG motif-antibodies that comprise variable region sequences or CDRs that have certain specified levels of identity in amino acid sequence to the variable region sequences or CDRs of the anti-GAG motif-antibodies disclosed herein.

In designing and producing additional anti-GAG motif-antibodies those skilled in the art may be guided by certain well known features of antibodies. The structure of typical naturally occurring antibodies is well known and includes two identical heavy chains and two identical light chains, with each light chain covalently linked to a heavy chain by an interchain disulfide bond. The two heavy chains are linked to one another by additional disulfide bonds. Individual heavy and light chains can fold into domains having similar sizes (e.g. 110-125 amino acids) and structures, but different functions. Light chains can comprise one variable domain (VL) and/or one constant domain (CL). Heavy chains can also comprise one variable domain (VH) and/or three or four constant domains (CH1, CH2, CH3 and CH4), depending on the class or isotype of antibody. In humans, the isotypes are IgA, IgD, IgE, IgG, and IgM, with IgA and IgG further subdivided into subclasses or subtypes (IgAQ1-2 and IgG1-4).

It has been found to be convenient to consider certain portions of antibody molecules individually. The portion of an antibody consisting of VL and VH domains is designated Fv (fragment variable) and constitutes the antigen-binding site. An antibody fragment containing a VL domain and a VH domain on one polypeptide chain is referred to as a single chain Fv (scFv) and generally contains the N terminus of one domain and the C terminus of the other domain joined by a flexible linker (see, e.g., U.S. Pat. No. 4,946,778 and International Patent Publication WO 88/09344. Accordingly, in some embodiments of the aspects described herein, the anti-GAG motif antibody fragment is an Fv fragment comprising or consisting essentially of the VL and VH domains of a single arm of an antibody. For certain embodiments disclosed herein, it may be advantageous to employ scFv fragments because scFv fragments lack some or all of the constant domains of whole antibodies. Therefore, they can overcome some of the disadvantages associated with the use of whole antibodies. For example, scFv fragments tend to be free of certain undesired interactions between heavy-chain constant regions and other biological molecules.

In certain embodiments, the anti-GAG motif antibodies or antigen-binding fragments thereof disclosed herein are multivalent single chain antibodies, where multiple single chain antibodies, each single chain having one VH and one VL domain covalently linked by a first peptide linker, are covalently linked by at least one or more second peptide linkers to form a multivalent single chain antibody. Each chain of a multivalent single chain antibody includes a variable light chain fragment and a variable heavy chain fragment, and is linked by the second peptide linker to at least one other chain. The second peptide linker is preferably composed of at least fifteen and fewer than one hundred amino acid residues.

In certain embodiments, the anti-GAG motif antibodies or antigen-binding fragments thereof disclosed herein are diabodies, where two single chain antibodies are combined to form a diabody. Diabodies have two chains and two binding sites, each specific for a GAG motif. Each chain of the diabody includes a VH domain connected to a VL domain. The domains are connected with linkers that are short enough to prevent pairing between domains on the same chain, thus driving the pairing between complementary domains on different chains to recreate the two antigen-binding sites.

In certain embodiments, anti-GAG motif antibodies or antigen-binding fragments thereof disclosed herein are triabodies, where three single chain antibodies are combined to form a triabody. In triabodies, the amino acid terminus of a VL or VH domain is directly fused to the carboxyl terminus of a VL or VH domain, i.e., without any linker sequence. The triabody has three Fv heads with the polypeptides arranged in a cyclic, head-to-tail fashion.

In certain embodiments, the anti-GAG motif antibody or antigen-binding fragment thereof is a Fab fragment, which comprises or consist essentially a variable (VL) and constant (CL) domain of the light chain and a variable domain (VH) and the first constant domain (CH1) of the heavy chain. In certain embodiments, the anti-GAG motif antibody or antigen-binding fragment thereof is a Fab' fragment, which refers to a Fab fragment having one or more cysteine residues at the C-terminus of the CH1 domain. In certain embodiments, the anti-GAG motif antibody or antigen-binding fragment thereof is a F(ab')2 fragment, which comprises a bivalent fragment comprising two Fab' fragments linked by a disulfide bridge at the hinge region.

In certain embodiments, the anti-GAG motif antibody or antigen-binding fragment thereof is an Fd fragment comprising or consisting essentially of VH and CH1 domains.

In certain embodiments, the anti-GAG motif antibody or antigen-binding fragment thereof is an Fd' fragment comprising VH and CH1 domains and one or more cysteine residues at the C-terminus of the CH1 domain.

In certain embodiments, the anti-GAG motif antibody or antigen-binding fragment thereof is a dAb fragment comprising or consisting essentially of a VH domain.

Linear antibodies refers to the antibodies as described in Zapata et al., Protein Engin., 8(10):1057-1062 (1995). Briefly, these antibodies comprise a pair of tandem Fd segments (VH-CH1-VH-CH1), which, together with complementary light chain polypeptides, form a pair of antigen binding regions. Linear antibodies can be bispecific or monospecific.

In certain embodiments, the anti-GAG motif antibody or antigen-binding fragment thereof is a linear antibody comprising a pair of tandem Fd segments (VH-CH1-VH-CH1) which, together with complementary light chain polypeptides, form a pair of antigen binding regions.

It is noted that the methods of the invention are not limited to antibodies or antigen binding fragments thereof. Also disclosed is the use other anti-GAG motif binding agents that selectively bind GAG motifs, as such aptamers. As used herein, "binding" to a GAG motif includes the selective interaction of the binding agent with the GAG motif Binding therefore includes, e.g., primary and secondary interactions including hydrogen bonds, ionic interactions, salt bridges, as well as hydrophilic and hydrophobic interactions. The terms "selective" and "selectivity" herein refer to the preferential binding of a binding agent (including, but not limited to an anti-GAG motif antibody or antigen binding fragment thereof) for a particular GAG motif, as opposed to binding to one or more other biological molecules.

Antibody Modifications

In some embodiments, the anti-GAG motif antibodies and antigen-binding fragments thereof disclosed herein are used in medium-throughput or high-throughout multiplex assays. As such, in some embodiments, the anti-GAG motif antibodies and antigen-binding fragments thereof disclosed herein may be covalently or non-covalently conjugated to a detectable moiety. Examples of detectable moieties provided herein include fluorescent moieties or labels, imaging agents, radioisotopic moieties, radiopaque moieties, and the like, e.g. detectable labels such as biotin, fluorophores, chromophores, spin resonance probes, or radiolabels. Exemplary fluorophores include fluorescent dyes and other luminescent molecules. A fluorophore may be environmentally sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei ($^{13}$C, $^{15}$N, $^{2}$H, 125I, 123I, 99Tc, 43K, 52Fe, 67Ga, 68Ga, 111In and the like). Other useful moieties are known in the art.

In certain embodiments, the anti-GAG motif antibodies and antigen-binding fragments thereof are covalently or non-covalently linked to a fluorescent protein or tag. Examples of fluorescent tags and proteins include, but are not limited to, (3-F)Tyr-EGFP, A44-KR, aacuGFP1, aacuGFP2, aceGFP, aceGFP-G222E-Y220L, aceGFP-h, AcGFP1, AdRed, AdRed-C148S, aeurGFP, afraGFP, alajGFP1, alajGFP2, alajGFP3, amCyan1, amFP486, amFP495, amFP506, amFP515, amilFP484, amilFP490, amilFP497, amilFP504, amilFP512, amilFP513, amilFP593, amilFP597, anm1GFP1, anm1GFP2, anm2CP, anobCFP1, anobCFP2, anobGFP, apulFP483, AQ14, AQ143, Aquamarine, asCP562, asFP499, AsRed2, asulCP, atenFP, avGFP, avGFP454, avGFP480, avGFP509, avGFP510, avGFP514, avGFP523, AzamiGreen, Azurite, BDFP1.6, bfloGFPal, bfloGFPcl, BFP, BFP.A5, BFP5, bsDronpa (On), ccalGFP1, ccalGFP3, ccalOFP1, ccalRFP1, ccalYFP1, cEGFP, cerFP505, Cerulean, CFP, cFP484, cfSGFP2, cgfmKate2, CGFP, cgfTagRFP, cgigGFP, cgreGFP, CheGFP1, CheGFP2, CheGFP4, Citrine, Citrine2, Clomeleon, Clover, cp-mKate, cpCitrine, cpT-Sapphire174-173, CyOFP1, CyPet, CyRFP1 (CyRFP1), d-RFP618, D10, d1EosFP (Green), d1EosFP (Red), d2EosFP (Green), d2EosFP (Red), deGFP1, deGFP2, deGFP3, deGFP4, dendFP (Green), dendFP (Red), Dendra (Green), Dendra (Red), Dendra2 (Green), Dendra2 (Red), Dendra2-M159A (Green), Dendra2-M159A (Orange), Dendra2-T69A (Green), Dendra2-T69A (Orange), dfGFP, dimer1, dimer2, dis2RFP, dis3GFP, dKeima, dKeima570, dLanYFP, DrCBD, Dreiklang (On), Dronpa (On), Dronpa-2 (On), Dronpa-3 (On), dsFP483, DspRl, DsRed, DsRed-Express, DsRed-Express2, DsRed-Max, DsRed.M1, DsRed.T3, DsRed.T4, DsRed2, DstCl, dTFPO.1, dTFPO.2, dTG, dTomato, dVFP, E2-Crimson, E2-Orange, E2-Red/Green, EaGFP, EBFP, EBFP1.2, EBFP1.5, EBFP2, ECFP, ECFPH148D, ECGFP, eechGFP1, eechGFP2, eechGFP3, eechRFP, efasCFP, efasGFP, eforCP, EGFP, eGFP203C, eGFP205C, Emerald, Enhanced Cyan-Emitting GFP, EosFP (Green), EosFP (Red), eqFP578, eqFP611, eqFP611V124T, eqFP650, eqFP670, EYFP, EYFP-Q69K, fabdGFP, ffDronpa (On), FoldingReporterGFP, FP586, FPrfl2.3, FR-1, FusionRed, FusionRed-M, G1, G2, G3, Gamillus (On), Gamillus0.1, Gamillus0.2, Gamillus0.3, Gamillus0.4, GCaMP2, gfasGFP, GFP(S65T), GFP-151pyTyrCu, GFP-Tyr151pyz, GFPmut2, GFPmut3, GFPxm16, GFPxm161, GFPxm162, GFPxm163, GFPxm18, GFPxm181uv, GFPxm18uv, GFPxm19, GFPxm191uv, GFPxm19uv, H9, HcRed, HcRed-Tandem, HcRed7, hcriGFP, hmGFP, HriCFP, HriGFP, iFP1.4, iFP2.0, iLov, iq-EBFP2, iq-mApple, iq-mCerulean3, iq-mEmerald, iq-mKate2, iq-mVenus, iRFP670, iRFP682, iRFP702, iRFP713, iRFP720, IrisFP (Green), IrisFP (Orange), IrisFP-M159A (Green), Jred, Kaede (Green), Kaede (Red), Katushka, Katushka-9-5, Katushka2S, KCY, KCY-G4219, KCY-G4219-38L, KCY-R1, KCY-R1-158A, KCY-R1-38H, KCY-R1-38L, KFP1 (On), KikGR1 (Green), KikGR1 (Red), KillerOrange, KillerRed, KO, Kohinoor (On), laesGFP, laGFP, LanFP1, LanFP2, lanRFP-AS831, LanYFP, laRFP, LSS-mKate1, LSS-mKate2, LSSmOrange, M355NA, mAmetrine, mApple, Maroon0.1, mAzamiGreen, mBanana, mBeRFP, mBlueberry1, mBlueberry2, mc1, mc2, mc3, mc4, mc5, mc6, McaG1, McaGlea, McaG2, mCardinal, mCarmine, mcavFP, mcavGFP, mcavRFP, mcCFP, mCerulean, mCerulean.B, mCerulean.B2, mCerulean.B24, mCerulean2, mCerulean2.D3, mCerulean2.N, mCerulean2.N(T65S), mCerulean3, mCherry, mCherry2, mCitrine, mClavGR2 (Green), mClavGR2 (Red), mClover3, mCyRFP1, mECFP, meffCFP, meffGFP, meffRFP, mEGFP, meleCFP, meleRFP, mEmerald, mEos2 (Green), mEos2 (Red), mEos2-A69T (Green), mEos2-A69T (Orange), mEos3.1 (Green), mEos3.1 (Red), mEos3.2 (Green), mEos3.2 (Red), mEos4a (Green), mEos4a (Red), mEos4b (Green), mEos4b (Red), mEosFP (Green), mEosFP (Red), mEosFP-F173S (Green), mEosFP-F173S (Red), mEosFP-M159A (Green), mEYFP, MfaGl, mGarnet, mGarnet2, mGeos-C(On), mGeos-E (On), mGeos-F (On), mGeos-L (On), mGeos-M (On), mGeos-S(On), mGinger1, mGinger2, mGrape1, mGrape2, mGrape3, mHoneydew, MiCy, mIFP, miniSOG, miniSOGQ103V, miniSOG2, miRFP, miRFP670, miRFP670nano, miRFP670vl, miRFP703, miRFP709, miRFP720, mIrisFP (Green), mIrisFP (Red), mK-GO (Early), mK-GO (Late), mKalamal, mKate, mKateM41GS158C, mKateS158A, mKateS158C, mKate2, mKeima, mKelly1, mKelly2, mKG, mKikGR (Green), mKikGR (Red), mKillerOrange, mKO, mKO2, mKOx, mLumin, mMaple (Green), mMaple (Red), mMaple2 (Green), mMaple2 (Red), mMaple3 (Green), mMaple3 (Red), mMaroonl, mmGFP, mMiCy, mmilCFP, mNectarine, mNeonGreen, mNeptune, mNeptune2, mNeptune2.5, mNeptune681, mNeptune684, Montiporasp. #20-9115, mOrange, mOrange2, moxBFP, moxCerulean3, moxDendra2 (Green), moxDendra2 (Red), moxGFP, moxMaple3 (Green), moxMaple3 (Red), moxNeonGreen, moxVenus, mPapaya, mPapaya0.7, mPlum, mPlum-E16P, mRaspberry, mRed7, mRed7Q1, mRed7Q1S1, mRed7Q1S1BM, mRFP1, mRFP1-Q66C, mRFP1-Q66S, mRFP1-Q66T, mRFP1.1, mRFP1.2, mRojoA, mRojoB, mRouge, mRtms5, mRuby, mRuby2, mRuby3, mScarlet, mScarlet-H, mScarlet-I, mStable, mStrawberry, mT-Sapphire, mTagBFP2, mTangerine, mTFP0.3, mTFP0.7 (On), mTFP1, mTFP1-Y67W, mTurquoise, mTurquoise2, muGFP, mUkG, mVenus, mVenus-Q69M, mVFP, mVFP1, mWasabi, Neptune, NijiFP (Green), NijiFP (Orange), NowGFP, obeCFP, obeGFP, obeYFP, OFP, OFPxm, oxBFP, oxCerulean, oxGFP, oxVenus, P11, P4, P4-1, P4-3E, P9, PA-GFP (On), Padron (On), Padron(star) (On), Padron0.9 (On), PAmCherry1 (On), PAmCherry2 (On), PAmCherry3 (On), PAmKate (On), PATagRFP (On), PATagRFP1297 (On), PATagRFP1314 (On), pcDronpa (Green), pcDronpa (Red), pcDronpa2 (Green), pcDronpa2 (Red), PdaC1, pdaelGFP, phiYFP, phiYFPv, pHluorin,ecliptic, pHluorin,ecliptic (acidic), pHluorin,ratiometric (acidic), pHluorin,ratiometric (alkaline), pHluorin2 (acidic), pHluorin2 (alkaline), pHuji, PlamGFP, pmeaGFP1, pmeaGFP2, pmimGFP1, pmimGFP2, Pp2FbFP, Pp2FbFPL30M, ppluGFP1, ppluGFP2, pporGFP, pporRFP, PS-CFP (Cyan), PS-CFP (Green), PS-CFP2 (Cyan), PS-CFP2 (Green), psamCFP, PSmOrange (Far-red), PSmOrange (Orange), PSmOrange2 (Far-red), PSmOrange2 (Orange), ptilGFP, R3-2+PCB, RCaMP, RDSmCherry0.1, RDSmCherry0.2, RDSmCherry0.5, RDSmCherryl, rfloGFP, rfloRFP, RFP611, RFP618, RFP630, RFP637, RFP639, roGFP1, roGFP1-R1, roGFP1-R8, roGFP2, rrenGFP, RRvT, rsCherry (On), rsCherryRev (On), rsCherryRevl.4 (On), rsEGFP (On), rsEGFP2 (On), rsFastLime (On), rsFolder (Green), rsFolder2 (Green), rsFusionRed1 (On), rsFusionRed2 (On), rsFusionRed3 (On), rsTagRFP (ON), Sandercyanin, Sapphire, sarcGFP, SBFP1, SBFP2, SCFP1, SCFP2, SCFP3A, SCFP3B, scubGFP1, scubGFP2, scubRFP, secBFP2, SEYFP, sgl1, sgl2, sg25, sg42, sg50, SGFP1, SGFP2, SGFP2(206A), SGFP2(E222Q), SGFP2(T65G), SHardonnay, shBFP, shBFP-N158S/L173I, ShG24, Sirius, SiriusGFP, Skylan-NS (On), Skylan-S(On), smURFP, SNIFP, SOPP, SOPP2, SOPP3, SPOON (on), stylGFP, SuperfolderGFP, SuperfoldermTurquoise2, SuperfoldermTurquoise2ox, SuperNovaGreen, SuperNovaRed, SYFP2, T-Sapphire, TagBFP, TagCFP, TagGFP, TagGFP2, TagRFP, TagRFP-T, TagRFP657, TagRFP675, TagYFP, td-RFP611, td-RFP639, tdimer2(12), tdKatushka2, TDsmURFP, tdTomato, tKeima, Topaz, TurboGFP, TurboGFP-V197L, TurboRFP, Turquoise-GL, Ultramarine, UnaG, usGFP, Venus, VFP, vsfGFP-0, vsfGFP-9, WiC, W2, W7, WasCFP, Wi-Phy, YPet, zFP538, zoan2RFP, ZsGreen, ZsYellowl, aGFP, 10B, 22G, 5B, 6C, Ala, aacuCP, acanFP, ahyaCP, amilCP, amilCP580, amilCP586, amilCP604, apulCP584, BFPsol, Blue102, CFP4, cgigCP, CheGFP3, Clover1.5, cpasCP, Cyl1.5, dClavGR1.6, dClover2, dClover2A206K, dhorGFP, dhorRFP, dPapaya0.1, Dronpa-C62S, DsRed-Timer, echFP, echiFP, EYFP-F46L, fcFP, fcomFP, Fpaagar, Fpag_frag, Fpcondchrom, FPmann, FPmcavgr7.7, Gamillus0.5, gdjiCP, gfasCP, GFPhal, gtenCP, hcriCP, hfriFP, KikG, LEA, mcFP497, mcFP503, mcFP506, mCherry1.5, mClavGR1, mClavGR1.1, mClavGR1.8, mCloverl.5, mcRFP, meffCP, mEos2-NA, meruFP, mKate2.5, mOFP.T.12, mOFP.T.8, montFP, moxEos3.2, mPA-GFP, mPapaya0.3, mPapaya0.6, mRFP1.3, mRFP1.4, mRFP1.5, mTFP0.4, mTFP0.5, mTFP0.6, mTFP0.8, mTFP0.9, mTFP1-Y67H, mTurquoise-146G, mTurquoise-146S, mTurquoise-DR, mTurquoise-GL, mTurquoise-GV, mTurquoise-RA, mTurquoise2-G, NpR3784g, PDM1-4, psupFP, Q80R, rfloGFP2, RpBphP1, RpBphP2, RpBphP6, rrGFP, RSGFP1, RSGFP2, RSGFP3, RSGFP4, RSGFP6, RSGFP7, Rtms5, scleFP1, scleFP2, spisCP, stylCP, sympFP, TeAPCa, tPapaya0.01, Trp-lessGFP, vsGFP, Xpa, yEGFP, YFP3, zGFP, and zRFP.

The anti-GAG motif antibodies and antigen-binding fragments thereof disclosed herein may also be fluorescently labeled using a fluorescent dye, including, but not limited to, (E)-Stilbene, (Z)-Stilbene, 1-Chloro-9,10-bis(phenylethy-nyl)anthracene, 2-Chloro-9,10-bis(phenylethynyl)anthra-cene, 2-Chloro-9,10-diphenylanthracene, 5,12-Bis(phenyl-ethynyl)naphthacene, 7-Aminoactinomycin D, 8-Anilinonaphthalene-1-sulfonic acid, 9,10-Bis(phenylethy-nyl)anthracene, Abberior® dyes (including CAGE 500, CAGE 532, CAGE 552, CAGE 590, CAGE 635, FLIP 565, STAR 440SXP, STAR 470SXP, STAR 488, STAR 520SXP, STAR 580, STAR 600, STAR 635, STAR 635P, STAR RED), Alexa Fluor® (AF) dyes (including 350, 405, 430, 488, 514, 532, 546, 555, 568, 594, 610-X, 633, 647, 660, 680, 700, 750, 790), Atto dyes (including Atto® 390, Atto® 425, Atto® 430 LS, Atto® 465, Atto® 488, Atto® 490 LS, Atto® 495, Atto® 514, Atto® 520, Atto® 532, Atto® 540Q, Atto® 542, Atto® 550, Atto® 565, Atto® 580Q, Atto® 590, Atto® 594, Atto® 610, Atto® 612Q, Atto® 620, Atto® 633, Atto® 647, Atto® 647-N, Atto® 655, Atto® 665, Atto® 680, Atto® 700, Atto® 725, Atto® 740, Atto® MB2, Atto® Oxal2, Atto® Rhol01, Atto® Rhol1, Atto® Rhol2, Atto® Rhol3, Atto® Rhol4, Atto® Rho3B, Atto® Rho6G, Atto® Thiol2), Auramine-rhodamine stain, Benzanthrone, BHQ-1, BHQ-2, BHQ-3, Bimane, Bisbenzimide, BODIPY, Car-boxy-rhodamine 6G, 5-isomer, Carboxy-X-rhodamine (ROX), 5-isomer, Carboxy-X-rhodamine (ROX), 6-isomer, Chromeo™ 488, Chromeo™ 494, Chromeo™ 546, Chro-meo™ 642, Coumarin, Cyanine 3, Cyanine 3.5, Cyanine 3.5 NHS, Cyanine 5, Cyanine 5 NHS, Cyanine 5.5 Amidite, Cyanine 5.5 NHS, Cyanine 7 NHS, DAPI, Dark quencher, Diphenylhexatriene, Dy® 350, Dy® 350 XL, Dy® 360 XL, Dy® 370 XL, Dy® 375 XL, Dy® 380 XL, Dy® 395 XL, Dy® 405, Dy® 415, Dy® 430, Dy® 431, Dy® 478, Dy® 480 XL, Dy® 481 XL, Dy® 485 XL, Dy® 490, Dy® 495, Dy® 505, Dy® 505-X, Dy® 510 XL, Dy® 511 XL, Dy® 520 XL, Dy® 521 XL, Dy® 530, Dy® 547, Dy® 547P1, Dy® 548, Dy® 549P1, Dy® 550, Dy® 554, Dy® 555, Dy® 556, Dy® 560, Dy® 590, Dy® 591, Dy® 594, Dy® 601 XL, Dy® 605, Dy® 610, Dy® 615, Dy® 630, Dy® 631, Dy® 632, Dy® 633, Dy® 634, Dy® 635, Dy® 636, Dy® 647, Dy® 647P1, Dy® 648, Dy® 648P1, Dy® 649, Dy® 649P1, Dy® 650, Dy® 651, Dy® 652, Dy® 654, Dy® 675, Dy® 676, Dy® 677, Dy® 678, Dy® 679P1, Dy® 680, Dy® 681, Dy® 682, Dy® 700, Dy® 701, Dy® 703, Dy® 704, Dy® 730, Dy® 731, Dy® 732, Dy® 734, Dy® 749P1, Dy® 750, Dy® 751, Dy® 752, Dy® 754, Dy® 776, Dy® 777, Dy® 778, Dy® 780, Dy® 781, Dy® 782 (infrared!), Dy® 800, Dy® 831, Dy®Q 1, Dy®Q 2, Dy®Q 3, Dy®Q 4, Dy®Q 660, Dy®Q 661, DyLight Fluor, EDANS, Epicocconone, Eterneon™ 350/430, Eterneon™ 350/455, Eterneon™ 384/480, Eterneon™ 393/523, Eterneon™ 394/507, Eterneon™ 480/635, Eterneon™ Far Red 680 Azide, Eterneon™ Green 515 Azide, Eterneon™ Orange 570 Azide, Eterneon™ Orange 580 Azide, Eterneon™ Red 600 Azide, Eterneon™ Red 630 Azide, Eterneon™ Red 645 Azide, Eterneon™ Yellow 530 Azide, Eterneon™ Yellow 550 Azide, Eter-neon™ Yellow 555 Azide, FAM, 5-isomer, FAM, 6-isomer, FlAsH-EDT2, FluoProbes, Fluorescein-5-EX, , Fluorescein Isothiocyanate (FITC), Fluorescence image-guided surgery, Fluoro-Jade stain, Fura-2, Fura-2-acetoxymethyl ester, HEX, Hoechst stain, IAEDANS, IBApy 493/503, IBApy FL, Iminocoumarin, Indo-1, JOE, 6-isomer, Laurdan, Luci-fer yellow, Luciferin, Methylene Blue (on request), NBD-TMA, Optical brightener, Oyster® 488, Oyster® 550, Oys-ter® 555, Oyster® 647, Oyster® 650, Oyster® 680, Perylene, Phycobilin, Phycoerythrobilin, Pyranine, Pyrene, Reichardt's dye, Rhodamine 110X, RiboGreen, Rubrene, Squaraine dye, Sulforhodamine 101, TAMRA, 6-isomer, TET, Tetraphenyl butadiene, Tetrasodium tris(batho-phenanthroline disulfonate)ruthenium(II), Titan yellow, TSQ, Umbelliferone, and Violanthrone. Fluorescent dyes can be chemically linked to proteins, including antibodies and antigen-binding fragments thereof, through various mechanisms. For instance, amine-reactive organic fluoro-phores include acylating reagents that form carboxamides, sulfonamides or thioureas upon reaction with amines. Amine-reactive organic fluorophores include, but are not limited to isothiocyanates, active esters and carboxylic acids, or sulfonyl chlorides. Thiol-reactive fluorescent dyes such as iodoacetamides or maleimides primarily target cys-teine residues.

Detectable moieties or purification tags can also be con-jugated to the anti-GAG motif antibodies or antigen-binding fragments thereof disclosed herein using Sortase A, which allows post-translational modifications of proteins at the N- and/or C-terminus. Sortase A from *S. aureus* recognizes an exposed peptide motif LPXTG, which serves as the acceptor for small fluorescent probes that have a primary amino-group and a tri-glycine motif [35, 38]. Upon cleavage of the LPXTG motif, Sortase forms a thioester intermediate with the engineered molecule. This intermediate is then resolved by nucleophilic attack by the (Gly)n containing molecule to form a fusion between the two molecules with an interven-ing LPXT(Gly)n motif. N and C-termini of proteins can be selectively labeled by using Sortases of different substrate specificity. For example, Sortase A from *Streptococcus pyo-genes*, recognizes and cleaves the LPXTA motif and accepts Ala-based nucleophiles. This SrtA also recognizes and cleaves the LPXTG motif with reduced efficiency. However, *S. aureus*. Sortase A does not recognize LPXTA substrates and thus are orthogonal to the LPXTA sequence.

While the use of immunotags has the benefit of signal amplification through a secondary antibody, the fusion of antibodies or fragments thereof with fluorescing protein and the SORTase A-based approaches are advantageous because the antibodies or fragments thereof are stoichiometrically labeled and thus the signal is directly proportional to the amount of bound scFv.

In some embodiments, the anti-GAG motif antibodies or antigen-binding fragments thereof disclosed herein may be conjugated to affinity tags for detection and/or purification. Examples of affinity tags include, but are not limited to, Albumin-binding protein (ABP), Alkaline Phosphatase (AP), AU1 epitope, AU5 epitope, Bacteriophage T7 epitope (T7-tag), Bacteriophage V5 epitope (V5-tag), Biotin-carboxy carrier protein (BCCP), Bluetongue virus tag (B-tag), Calmodulin binding peptide (CBP), Chloramphenicol Acetyl Transferase (CAT), Cellulose binding domain (CBP), Chitin binding domain (CBD), Choline-binding domain (CBD), Dihydrofolate reductase (DHFR), E2 epitope, FLAG epitope, Galactose-binding protein (GBP), Green fluorescent protein (GFP), Glu-Glu (EE-tag), Glutathione S-transferase (GST), Human influenza hemagglutinin (HA), HaloTag®, Histidine affinity tag (HAT), Horseradish Peroxidase (HRP), HSV epitope, Ketosteroid isomerase (KSI), KT3 epitope, LacZ, Luciferase, Maltose-binding protein (MBP), Myc epitope, NusA, PDZ domain, PDZ ligand, Polyarginine (Arg-tag), Polyaspartate (Asp-tag), Polycysteine (Cys-tag), Polyhistidine (His-tag), Polyphenylalanine (Phe-tag), Profinity eXact, Protein C, Si-tag, S-tag, Streptavadin-binding peptide (SBP), Staphylococcal protein A (Protein A), Staphylococcal protein G (Protein G), Strep-tag, Streptavadin, Small Ubiquitin-like Modifier (SUMO), Tandem Affinity Purification (TAP), T7 epitope, Thioredoxin (Trx), TrpE, Ubiquitin, Universal, and VSV-G.

Other Conjugates of Antibodies or Antigen Binding Fragments Thereof

In some embodiments, the anti-GAG motif antibodies or antigen binding fragments thereof disclosed herein are conjugated to a polymer to increase stability and/or half-life of the antibody or antigen binding fragment thereof. In one embodiment, the anti-GAG motif antibody or antigen binding fragment thereof is conjugated to a polyalkylene glycol moiety, for example, a PEG moiety and preferably a PEG-maleimide moiety. Preferred pegylation moieties (or related polymers) can be, for example, polyethylene glycol ("PEG"), polypropylene glycol ("PPG"), polyoxyethylated glycerol ("POG") and other polyoxyethylated polyols, poly-vinyl alcohol ("PVA") and other polyalkylene oxides, poly-oxyethylated sorbitol, or polyoxyethylated glucose. The polymer can be a homopolymer, a random or block copolymer, a terpolymer based on the monomers listed above, straight chain or branched, substituted or unsubstituted as long as it has at least one active sulfone moiety. The polymeric portion can be of any length or molecular weight but these characteristics can affect the biological properties. Polymer average molecular weights particularly useful for decreasing clearance rates in pharmaceutical applications are in the range of 2,000 to 35,000 Daltons. In addition, if two groups are linked to the polymer, one at each end, the length of the polymer can impact upon the effective distance, and other spatial relationships, between the two groups. Thus, one skilled in the art can vary the length of the polymer to optimize or confer the desired biological activity. PEG is useful in biological applications for several reasons. PEG typically is clear, colorless, odorless, soluble in water, stable to heat, inert to many chemical agents, does not hydrolyze, and is nontoxic. Pegylation can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. In addition, pegylation can increase the solubility of a biologically active molecule.

In some embodiments, the anti-GAG motif antibodies or antigen binding fragments thereof disclosed herein are attached to a salvage receptor binding epitope to increase the half-life of the anti-GAG motif antibodies or antigen binding fragments thereof. The term "salvage receptor binding epitope" may refer to an epitope of the Fc region of an IgG molecule (e.g., IgG1, IgG2, IgG3, or IgG4) that is responsible for increasing the in vivo serum half-life of the IgG molecule (e.g., Ghetie et al., 18 Ann. Rev. Immunol. 739 (2000). Antibodies with substitutions in an Fc region thereof and increased serum half-lives are also described in WO 00/42072, WO 02/060919; Shields et al., 276 J. Biol. Chem. 6591 (2001); Hinton, 279 J. Biol. Chem. 6213-6216 (2004). For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. In another embodiment, the serum half-life can also be increased, for example, by attaching other polypeptide sequences. For example, antibodies or antigen-binding fragments thereof useful in the methods of the invention can be attached to serum albumin or a portion of serum albumin. See also, Dennis et al., 277 J. Biol. Chem. 35035 (2002), for additional serum albumin binding peptide sequences.

Kits

In some embodiments, provided are kits comprising one or more anti-GAG motif antibodies or antigen binding fragments thereof disclosed herein.

In some embodiments, the kit comprises one or more anti-GAG motif antibodies or antigen binding fragments thereof that are conjugated to a functional moiety that allows for the detection or purification of the one or more anti-GAG motif antibodies or antigen binding fragments thereof disclosed herein.

In some embodiments, the kit comprises one or more anti-GAG motif antibodies or antigen binding fragments thereof conjugated to a therapeutic or stabilizing moiety.

In some embodiments, the one or more anti-GAG motif antibodies or antigen binding fragments thereof may be present in the kit in a single composition. In other embodiments, the one or more anti-GAG motif antibodies or antigen binding fragments thereof may be present in separate compositions.

The kit may comprise additional therapeutic or non-therapeutic compositions. In certain embodiments, the kit comprise instructions in a tangible medium.

Uses of Anti-GAG Motif Antibodies or Antigen Binding Fragments Thereof

In some embodiments, the anti-GAG motif antibodies or antigen binding fragments thereof are used for the identification, purification, or modulation of a cell or tissue based on a cellular glycotype.

In some embodiments, the anti-GAG motif antibodies or antigen binding fragments thereof are provided in a partially or substantially purified form. In some embodiments, the anti-GAG motif antibodies or antigen binding fragments thereof are provided as supernatants of cells secreting the anti-GAG motif antibodies or antigen binding fragments thereof.

In some embodiments, the anti-GAG motif antibodies or antigen binding fragments thereof are provided in form of cells expressing the anti-GAG motif antibodies or antigen binding fragments thereof. In some embodiment, the anti-GAG motif antibodies or antigen binding fragments thereof are fused to a transmembrane domain. In some embodiments, the cells expressing the anti-GAG motif antibodies or antigen binding fragments thereof are HEK293 cells or T cells.

In some embodiments, the anti-GAG motif antibodies or antigen binding fragments thereof are provided in form of a chimeric antigen receptor, such as an artificial T cell receptor.

Purification, and Isolation Methods

In one aspect, provided is a method of purifying or isolating cells, the method comprising contacting a mixture of cells comprising one or more target cells with one or more anti-GAG motif antibodies or antigen binding fragments thereof, wherein the anti-GAG motif antibodies or antigen binding fragments thereof bind to the one or more target cells.

The methods disclosed herein are also useful for the isolation of tissues. As such, also provided is a method of purifying or isolating tissues, the method comprising contacting a mixture of tissues comprising one or more target tissues with one or more anti-GAG motif antibodies or antigen binding fragments thereof, wherein the anti-GAG motif antibodies or antigen binding fragments thereof bind to the one or more target tissues. The term "purification" or "isolating" refers to any process or method by which a specific compound and/or complex may be removed from a mixture or composition.

In some embodiments, the anti-GAG motif antibodies or antigen binding fragments thereof used for the purification of a cell or tissue are further conjugated to moiety that aids in purification. Non-limiting examples of such purification moieties include affinity tags (including, but not limited to, peptides and proteins) or magnetic moieties.

In some embodiments, the one or more target cells that are bound to the one or more anti-GAG motif antibodies or antigen binding fragments thereof are separated from cells that are not bound to the one or more anti-GAG motif antibodies or antigen binding fragments thereof by flow cytometry. In some embodiments, the flow cytometry is fluorescence-activated flow cytometry.

In some embodiments, the method comprises contacting the one or more target cells with one or more anti-GAG motif antibodies or antigen binding fragments thereof comprising an affinity tag. In some embodiments, the method comprises (a) contacting the one or more target cells with one or more anti-GAG motif antibodies or antigen binding fragments thereof comprising an affinity tag;

(b) contacting the one or more target cells bound to the one or more anti-GAG motif antibodies or antigen binding fragments thereof comprising the affinity tag with a medium that has a higher affinity for the affinity tag than the remainder of the mixture or composition; and (c) isolating the one or more target cells bound to the one or more anti-GAG motif antibodies or antigen fragments thereof carrying the affinity tag.

In some embodiments, the anti-GAG motif antibodies or antigen binding fragments thereof used for the purification of a cell or tissue is further conjugated to a magnetic moiety, allowing for magnetic separation of the one or more cells bound to the one or more anti-GAG motif antibodies or antigen fragments thereof.

Cell separating techniques utilizing antibodies or antigen binding fragments are known in the art and can be adapted by a person skilled in the person for the use in the methods disclosed herein.

In some embodiments, the anti-GAG motif antibodies or antigen binding fragments thereof are used to differentiate between and isolate cell populations that cannot be separated using other surface markers, such as the CD system. For instance, hematopoietic cell populations stringently isolated based on the same cell surface CD markers display considerable heterogeneity, e.g. distinct transcriptional programs and definable cellular subsets.

Diagnostic Methods

The anti-GAG motif antibodies and antigen binding fragments herein may be used to discriminate between healthy and diseased cells. As such, in one aspect, provided is a method for revealing a disease or disorder, the method comprising contacting one or more cells with one or more anti-GAG motif antibody or antigen binding fragment thereof.

In some embodiments, the presence of one or more GAG motifs is indicative of the disease or disorder. In one embodiment, provided is a method of detecting a disease or disorder, the method comprising:

(a) contacting one or more cells with one or more anti-GAG motif antibodies or antigen binding fragments thereof, (b) measuring binding of the one or more anti-GAG motif antibodies or antigen binding fragments thereof to the one or more cells; and (c) detecting the disease or disorder if binding of the one or more anti-GAG motif antibodies or antigen binding fragments thereof to the one or more cells was detected.

In some embodiments, the absence of one or more GAG motifs is indicative of the disease or disorder. In one embodiment, provided is a method of detecting a disease or disorder, the method comprising:

(a) contacting one or more cells with one or more anti-GAG motif antibodies or antigen binding fragments thereof, (b) measuring binding of the one or more anti-GAG motif antibodies or antigen binding fragments thereof to the one or more cells; and (c) detecting the disease or disorder if binding of the one or more anti-GAG motif antibodies or antigen binding fragments thereof to the one or more cells was not detected.

In some embodiments, the one or more cells contacted with the one or more anti-GAG motif antibodies or antigen binding fragments thereof are provided in a sample. In some embodiments, the sample is derived from a human, primate, hamster, rabbit, rodent, cow, pig, sheep, horse, goat, dog, guinea pig, ferret, or cat. In some embodiments, the sample is a blood, serum, plasma, urine, feces, tissue biopsy sample.

In some embodiments, the methods disclosed herein are suitable for prognosing a disease or disorder. In some embodiments, the methods disclosed herein are suitable for monitoring progression of a disease. In some embodiments, the methods disclosed herein are suitable for determining the efficacy of treatment.

In some embodiments, the method of detecting a disease or disorder comprises determining the glycotype of a control. The "glycotype of a control" can refer to the glycotype of a cell derived from one or more individuals that do not have the disease or disorder to be detected. The control glycotype may be determined on an individual-by-individual basis, or on an aggregate basis such as an average. In some embodiments, the control glycotype is determined for the same individual whose condition is being monitored, but is obtained at a different time. In certain embodiments, the control glycoype can refer to a glycotype determined for the same patient at an earlier time, e.g., weeks, months, or years earlier. In some embodiment, the control glycotype is determined for a patient before the patient receives any treatment for a specific disease.

In some embodiments, the cells or tissues detected by the anti-GAG motif antibodies or antigen binding fragments thereof are cancer cells. In some embodiments, the cancer is basal cell carcinoma, biliary tract cancer; bladder cancer;

bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g; small-cell lung cancer, non-small cell lung cancer, adenocarcinoma of the lung, and squamous carci-noma of the lung); lymphoma including Hodgkin's and non-Hodgkin's lymphoma; melanoma; myeloma; neuro-blastoma; oral cavity cancer (e.g., lip, tongue, mouth, and pharynx); ovarian cancer; pancreatic cancer; prostate can-cer; retinoblastoma; rhabdomyosarcoma; rectal cancer; can-cer of the respiratory system; salivary gland carcinoma; sarcoma; skin cancer; squamous cell cancer; stomach can-cer; testicular cancer; thyroid cancer; uterine or endometrial cancer; cancer of the urinary system; vulval cancer; as well as other carcinomas and sarcomas; as well as B-cell lym-phoma (including low grade/follicular non-Hodgkin's lym-phoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In some embodiments, the methods disclosed herein are used to identify and/or isolate leukemic stem/progenitor and bulk cell populations.

It is noted that the methods disclosed herein can be used to diagnose any disease associated with a modified cellular glycotype as compared to the non-disease state. As such, diseases that can be diagnoses using the methods disclosed herein include, but are not limited to, metabolic diseases, infectious diseases, auto-immune diseases.

Therapeutic Methods

In one aspect, provided is a method of targeting a thera-peutic agent to a target cell or a target tissue based on the glycotype of the target cell or target tissue. As such, pro-vided herein are anti-GAG motif antibodies or antigen binding fragments thereof that are covalently or noncova-lently conjugated to a therapeutic moiety and methods of using such anti-GAG motif antibodies or antigen binding fragments thereof.

In some embodiments, provided is a method of treating and/or preventing a disease, the method comprising admin-istering to the subject in need thereof an effective amount of one or more anti-GAG motif antibodies or antigen binding fragments thereof that are conjugated to a therapeutic moi-ety, wherein the one or more anti-GAG motif antibodies or antigen binding fragments thereof bind to one or more GAG motifs on the surface of the target cell or target tissue.

To "treat" or to use for "therapy" refers to administering of a therapeutic agent to a subject already diagnosed as having or suffering from a disease or disorder with the goal of improving the subject's condition. The object of the treatment is to prevent or slow down (lessen) an undesired physiological condition, disorder or disease, or to obtain beneficial or desired clinical results. Beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment. "Prevent" refers to prophylactic treatment of a subject who is not yet ill, but who is susceptible to, or otherwise at risk for, developing a disease or disorder.

Different formats of the anti-GAG motif antibodies may be used for the methods of treatment disclosed herein, including, but not limited to, whole IgG or scFv formats. The antigen binding portions of the anti-GAG motif antibodies and fragments disclosed herein may also be formatted in to a chimeric antigen receptor and may be used in CAR T-cell therapy.

Examples of therapeutic moieties which are useful in the methods and antibodies and antigen-binding fragments thereof contemplated by the invention include, for example, anti-inflammatory agents, anti-cancer agents, anti-neurode-generative agents, anti-infective agents, or generally a thera-peutic. The functional moiety may also have one or more of the above-mentioned functions.

Exemplary therapeutic moieties include radionuclides with high-energy ionizing radiation that are capable of causing multiple strand breaks in nuclear DNA, and there-fore suitable for inducing cell death (e.g., of a cancer). Exemplary high-energy radionuclides include: $^{90}$Y, $^{125}$I, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re. These isotopes typically produce high-energy $\alpha$- or $\beta$-particles which have a short path length. Such radionuclides kill cells to which they are in close proximity, for example neoplastic cells to which the conju-gate has attached or has entered. They have little or no effect on non-localized cells and are essentially non-immunogenic.

Exemplary therapeutic moieties also include cytotoxic agents such as cytostatics (e.g. alkylating agents, DNA synthesis inhibitors, DNA-intercalators or cross-linkers, or DNA-RNA transcription regulators), enzyme inhibitors, gene regulators, cytotoxic nucleosides, tubulin binding agents, hormones and hormone antagonists, anti-angiogen-esis agents, and the like.

Exemplary therapeutic moieties also include alkylating agents such as the anthracycline family of drugs (e.g., adriamycin, carminomycin, cyclosporin-A, chloroquine, methopterin, mithramycin, porfiromycin, streptonigrin, anthracenediones, and aziridines). In another embodiment, the chemotherapeutic moiety is a cytostatic agent such as a DNA synthesis inhibitor. Examples of DNA synthesis inhibitors include, but are not limited to, methotrexate and dichloromethotrexate, 3-amino-1,2,4-benzotriazine 1,4-di-oxide, aminopterin, cytosine $\beta$-D-arabinofuranoside, 5-fluoro-5'-deoxyuridine, 5-fluorouracil, ganciclovir, hydroxyurea, actinomycin-D, and mitomycin C. Exemplary DNA-intercalators or cross-linkers include, but are not lim-ited to, bleomycin, carboplatin, carmustine, chlorambucil, cyclophosphamide, cis-diammineplatinum(II) dichloride (cisplatin), melphalan, mitoxantrone, and oxaliplatin.

Exemplary therapeutic moieties also include transcription regulators such as actinomycin D, daunorubicin, doxorubi-cin, homoharringtonine, and idarubicin. Other exemplary cytostatic agents that are compatible with the present invention include ansamycin benzoquinones, quinonoid derivatives (e.g. quinolones, genistein, bactacyclin), busulfan, ifosfamide, mechlorethamine, triaziquone, diaziquone, carbazilquinone, indoloquinone E09, diaziridinyl-benzoquinone methyl DZQ, triethylenephosphoramide, and nitrosourea compounds (e.g. carmustine, lomustine, semustine).

Exemplary therapeutic moieties also include cytotoxic nucleosides such as, for example, adenosine arabinoside, cytarabine, cytosine arabinoside, 5-fluorouracil, fludarabine, floxuridine, ftorafur, and 6-mercaptopurine; tubulin binding agents such as taxoids (e.g. paclitaxel, docetaxel, taxane), nocodazole, rhizoxin, dolastatins (e.g. Dolastatin-10, -11, or -15), colchicine and colchicinoids (e.g. ZD6126), combretastatins (e.g. Combretastatin A-4, AVE-6032), and vinca alkaloids (e.g. vinblastine, vincristine, vindesine, and vinorelbine (navelbine)); anti-angiogenesis compounds such as Angiostatin K1-3, DL-α-difluoromethyl-ornithine, endostatin, fumagillin, genistein, minocycline, staurosporine, and (1)-thalidomide.

Exemplary therapeutic moieties also include hormones and hormone antagonists, such as corticosteroids (e.g. prednisone), progestins (e.g. hydroxyprogesterone or medroprogesterone), estrogens, (e.g. diethylstilbestrol), antiestrogens (e.g. tamoxifen), androgens (e.g. testosterone), aromatase inhibitors (e.g. aminogluthetimide), 17-(allylamino)-17-demethoxygeldanamycin, 4-amino-1,8-naphthalimide, apigenin, brefeldin A, cimetidine, dichloromethylene-diphosphonic acid, leuprolide (leuprorelin), luteinizing hormone-releasing hormone, pifithrin-α, rapamycin, sex hormone-binding globulin, and thapsigargin.

Exemplary therapeutic moieties also include enzyme inhibitors such as, S(+)-camptothecin, curcumin, (−)-deguelin, 5,6-dichlorobenz-imidazole 1-β-D-ribofuranoside, etoposide, formestane, fostriecin, hispidin, 2-imino-1-imidazolidineacetic acid (cyclocreatine), mevinolin, trichostatin A, tyrphostin AG 34, and tyrphostin AG 879.

Exemplary therapeutic moieties also include gene regulators such as 5-aza-2'-deoxycytidine, 5-azacytidine, cholecalciferol (vitamin D3), 4-hydroxytamoxifen, melatonin, mifepristone, raloxifene, trans-retinal (vitamin A aldehydes), retinoic acid, vitamin A acid, 9-cis-retinoic acid, 13-cis-retinoic acid, retinol (vitamin A), tamoxifen, and troglitazone.

Exemplary therapeutic moieties also include cytotoxic agents such as, for example, the pteridine family of drugs, diynenes, and the podophyllotoxins. Particularly useful members of those classes include, for example, methopterin, podophyllotoxin, or podophyllotoxin derivatives such as etoposide or etoposide phosphate, leurosidine, vindesine, leurosine and the like.

Still other cytotoxins that are compatible with the teachings herein include auristatins (e.g. auristatin E and monomethylauristan E), calicheamicin, gramicidin D, maytansanoids (e.g. maytansine), neocarzinostatin, topotecan, taxanes, cytochalasin B, ethidium bromide, emetine, tenoposide, colchicin, dihydroxy anthracindione, mitoxantrone, procaine, tetracaine, lidocaine, propranolol, puromycin, and analogs or homologs thereof.

Exemplary therapeutic moieties also include immunomodulatory agents. In some embodiments, the immunomodulatory agent enhances the immune response and may, for example, be used in the treatment of cancer. In another embodiment, the immunomodulatory agent decrease the immune response and/or blocks immunostimulatory interactions and may, for example, be used for the treatment of auto-immune or inflammatory diseases.

In some embodiments, the anti-GAG motif antibodies or antigen binding fragments thereof disclosed herein are provided in form of a bispecific antibody. In one embodiment, the second binding site of the bispecific antibody is derived from an immunomodulatory antibody and antigen binding fragment thereof.

In one embodiments, the therapeutic moiety is an immune cell engager, including but not limited to a T cell, NK cell, and/or macrophage engager. In one embodiment, the therapeutic moiety is bi-specific T-cell engagers (BiTEs), which forms a bridge between a cytotoxic T cell and a tumor cell. In some embodiments, the therapeutic moiety is a cytokine, a chemokine, an interleukin, or an immunomodulatory imide drug.

In one embodiment, the therapeutic moiety is a checkpoint inhibitor. Checkpoint proteins interact with specific ligands that send a signal into the T cell and switch off or inhibit T cell function. By expressing high levels of checkpoint proteins on their surface, cancer cells can control the function of T cells that enter the tumor microenvironment, thus suppressing the anticancer immune response. The immune checkpoint protein Programmed Death-1 (PD-1) is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1 (Freeman et al., 2000; Latchman et al., 2001). Inhibition of the PD-1/PD-L1 interaction can promote potent antitumor activity. Examples of PD-1 inhibitors include, but are not limited to, Pembrolizumab (MK-3475), Nivolumab (MDX-1106), Cemiplimab-rwlc (REGN2810), Pidilizumab (CT-011), Spartalizumab (PDR001), tislelizumab (BGB-A317), PF-06801591, AK105, BCD-100, BI 754091, JS001, LZM009, MEDIO680, MGA012, Sym021, TSR-042. Examples of PD-L1 inhibitors include, but are not limited to, Atezolizumab (MPDL3280A), Durvalumab (MEDI4736), Avelumab (MSB0010718C), BGB-A333, CK-301, CS1001, FAZ053, KN035, MDX-1105, MSB2311, SHR-1316.

In some embodiments, the anti-GAG motif antibodies or antigen binding fragments thereof are fused to or expressed on the surface of an immune cell, including, but not limited to a T cells NK cell, macrophage, or another immune effector cell. In some embodiments, the anti-GAG motif antibodies or antigen binding fragments thereof are provided in form of a chimeric antigen receptor, such as an artificial T cell receptor, which is expressed on a T cell.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

It is to be understood that this invention is not limited to the particular molecules, compositions, methodologies, or protocols described, as these may vary. Any methods and materials similar or equivalent to those described herein can be used in the practice or testing of embodiments of the present invention. It is further to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes those possibilities).

All other referenced patents and applications are incorporated herein by reference in their entirety. Furthermore, where a definition or use of a term in a reference, which is incorporated by reference herein is inconsistent or contrary to the definition of that term provided herein, the definition of that term provided herein applies and the definition of that term in the reference does not apply.

To facilitate a better understanding of the present invention, the following examples of specific embodiments are given. The following examples should not be read to limit or define the entire scope of the invention.

EXAMPLES

Example 1: Glycotype-Based Discrimination of Different Cell Types Using Cell-Cell Interaction Assays or Purified Anti-GAG Motif Antibody Fragments First, it was determined whether anti-GAG motif antibodies or antigen binding fragments expressed on the surface of reporter cells can be used to discriminate between different cell types based on the cell's glycotype. The expression of anti-GAG motif antibodies on the surface of reporter cells circumvents the cost of large-scale expression and purification of anti-GAG motif antibodies or antigen binding fragments, as the anti-GAG motif antibodies or antigen binding fragments are made by and presented on the surface of transfected reporter cells.

Figure 2A:
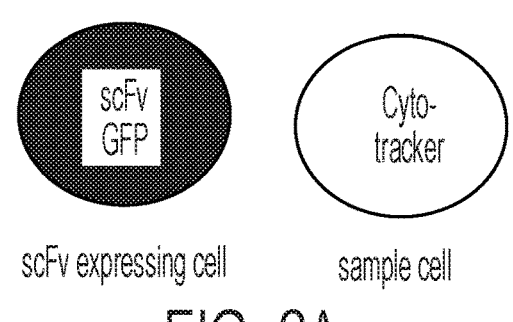
FIG. 2A Anti-HS motif scFvs were fused to a transmembrane domain, which is turn fused to a green fluorescent protein. The fusion proteins were then expressed on the surface of HEK cells ("reporter cells"). The reporter cells were mixed with suspension adapted HEK or CHO cells ("sample cells"), respectively, which were fluorescently labeled with cyto-tracker dye. Binding (double positive events) were detected by flow cytometry.

A library of cDNA clones was synthesized encoding 36 anti-HS motif scFvs. The scFcs were engineered to contain both a secretion signal at the N-terminus and a transmembrane domain fused to a fluorescent protein tag (e.g., GFP, YFP, RFP) at the C-terminus. The scFvs were then transgenically expressed in living animals or tissues to visualize HS. For this, the scFv cDNA was cloned into a mammalian expression vector that allows expression of the scFv on the surface of reporter cells as transmembrane proteins. These fluorescently labeled scFvs were then used to detect glycan-scFv interaction in cell-cell interactions assays. Cells transiently expressing an anti-HS motif-scFv/GFP fusion were mixed with cyto-tracker labeled fluorescent sample cells and the interaction between the two cells populations quantified using flow cytometry (see FIG. 2A).

Figure 2B:
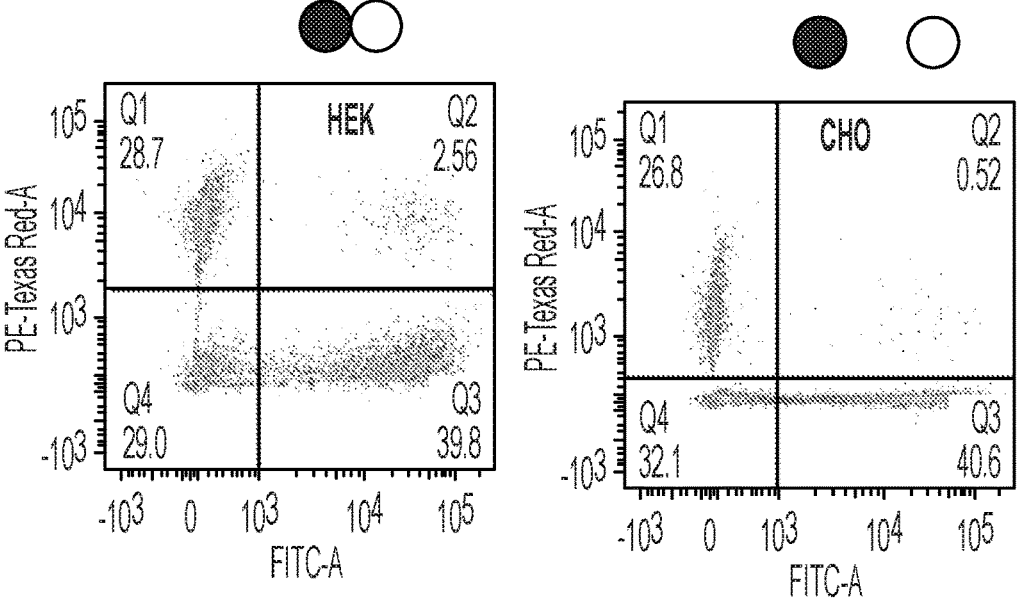
FIG. 2B Representative experimental data from flow cytometry with reporter cells expressing anti-HS motif scFvs HS4C3.
Figure 2C:
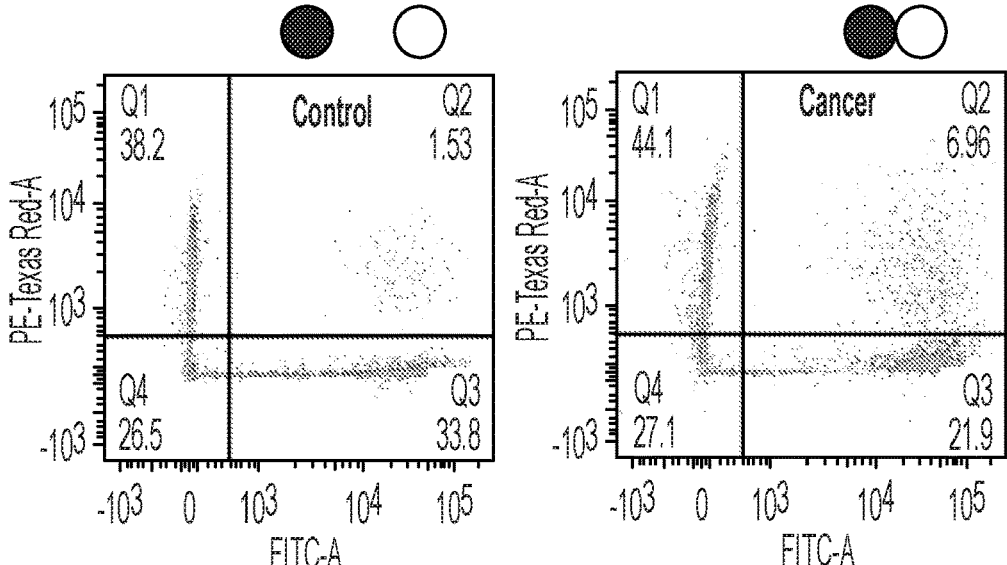
FIG. 2C. Adherent MIA PaCa-2 cancer cells ("Cancer") or immortalized primary pancreatic duct control cells ("Control") were interrogated by reporter cells expressing scFv LKIV69.

This cell-cell interaction assay was used to successfully glycotype two common laboratory cell lines: Suspension adapted human embryonic kidney cells (HEK 293) and Chinese hamster ovary cells (CHO). FIG. 2B shows representative flow cytometry data for HEK and CHO cells probed with reporter cells expressing anti-HS motif scFv HS4C3 on their surface. The reporter cells bind to HEK 293, but not to CHO cells.

scFv expressed on cells could further be used to differentiate cancer cells (adherent MIA PaCa-2 from control cells (immortalized primary pancreatic duct cells). FIG. 2C shows representative flow cytometry data for cancer and control cells probed with reporter cells expressing anti-HS motif scFv LKIV69 on their surface.

These results demonstrate that anti-GAG motif antibodies or antigen binding fragments expressed on the surface of reporter cells, as well as purified anti-GAG motif antibodies or antigen binding fragments can be used to discriminate between different cell types based on the cell's glycotype.

Example 2: Identification of Cellular Glycotypes

Figures 3A, 3B:
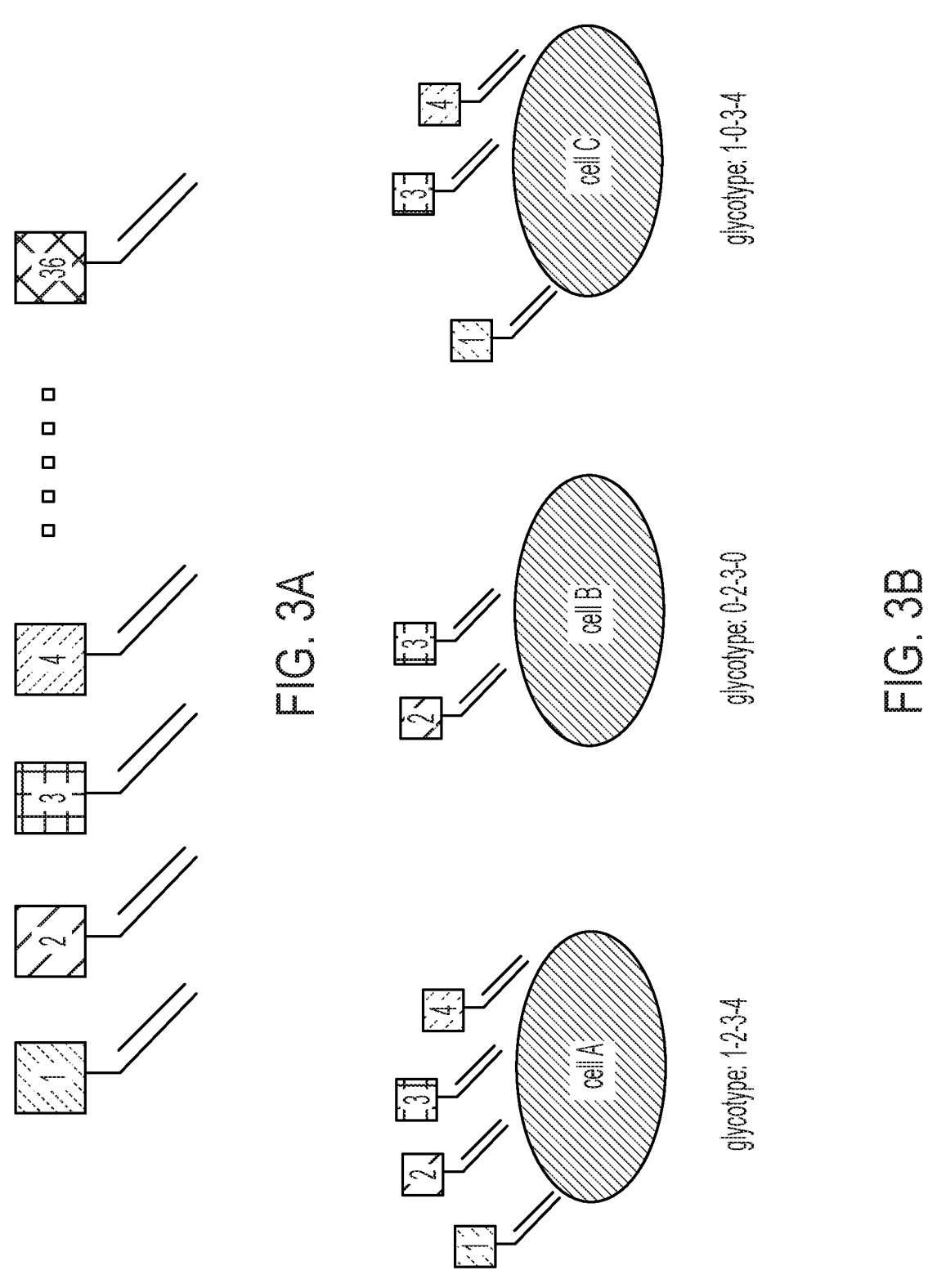
FIG. 3A illustrates a suite of anti-GAG motif antibodies or antigen binding fragments thereof.
FIG. 3B illustrates differential binding of a suite of anti-GAG motif antibodies or antigen binding fragments thereof to different cell types.

By measuring the binding of different anti-GAG motif antibodies or fragments thereof to a cell, a unique cellular glycotype can be defined. Such binding can be determined both qualitatively and quantitatively. Rather than analyzing the HS and/or CS structure of a given cell of interest, the HS/CS complement of a cell is defined by which anti-GAG motif antibodies or fragments thereof can bind to a cell, essentially creating a unique bar code for each cell. This concept is illustrated in FIG. 3A and FIG. 3B.

Figure 3C:
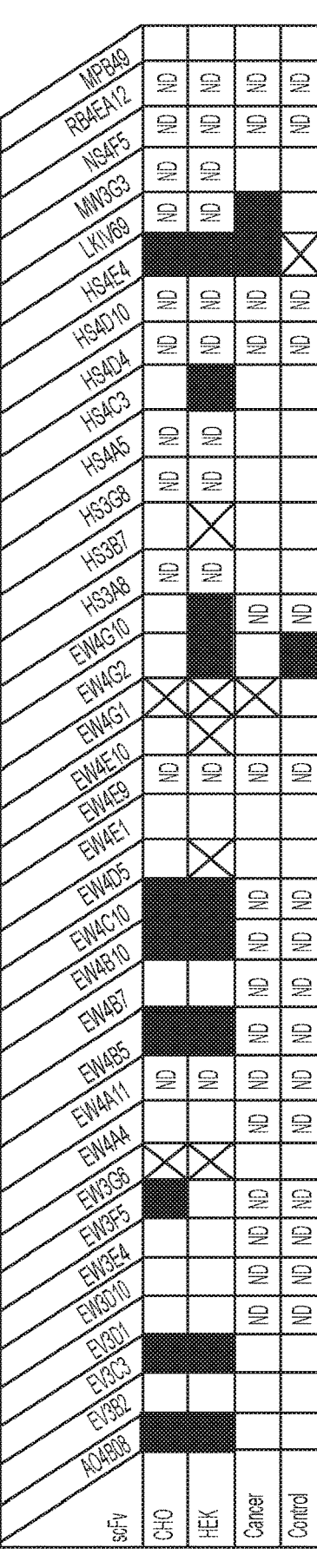
FIG. 3C shows the "glycotype" of four homogeneous cell populations as determined by using the cell-cell interaction assay with reporter and sample cells used in FIG. 2. Black square indicates binding. Crossed square=intermediate binding, white square=no binding. ND, not determined.

Using the experimental setup and cell populations described in Example 1, cellular glycotypes were determined for CHO cells, HEK cells, MIA PaCa-2 cells, and control cells (see FIG. 3C). For example, in regards to CHO vs HEK cells, it is noted that using only a subset of 23 of the 36 scFvs, including the MPB49 (which does not recognize any glycosaminoglycan) as a negative control, nine qualitative differences between both cell lines were identified.

This demonstrates the discriminatory power and utility of scFv-based glycotyping approach.

Example 3: Anti-GAG Motif Antibodies and Antigen Binding Fragments Thereof are Suitable for Multiplexing To provide a suite of anti-GAG motif antibodies suitable for high-throughput analysis of different cell types, a library of cDNA clones was synthesized encoding 36 anti-HS motif and 5 CS motif antibodies in scFv format. The scFvs were cloned into different mammalian expression vectors that allow expression of the scFvs as secreted forms, affinity tagged forms, and/or as Fc-fusions.

By using different immuno- and fluorescent tagging approaches, anti-GAG motif antibodies or antigen binding fragments thereof can be rendered amenable to multiplexing. For instance, the addition of an immunotag such as 6×HIS, FLAG, V5, VSVg, and Myc epitopes allows not only capture of labeled cells, but also signal amplification through a secondary antibody. scFvs can also be engineered to include a C-terminal signal that will allow for the enzymatic addition of fluorescent conjugates via the bacterial enzyme Sortase A. This method allows enzymatic labeling of the scFv with a single fluorescent or affinity molecule or of choice, providing great flexibility for multiplexing and customization purposes. Of note, the generation of anti-GAG motif antibody fusions with fluorescent proteins or the application of a Sortase A-based fluorescent labeling approach allows stoichiometrical labelling of anti-GAG motif antibodies or antigen binding fragments thereof and generating a signal that is directly proportional to the amount of bound anti-GAG motif antibody or antigen binding fragment thereof.

Secreted scFvs carrying affinity tags were produced in bacteria, or transgenically expressed in *C. elegans* as scFvs fused to fluorescent proteins including GFP, superfolder GFP, or tagRFP. scFvs containing a Sortase A substrate sequence were successfully fluorescently labeled using GGC::FITC, a tri-peptide conjugated to FITC, illustrating the flexibility of a Sortase A based labeling approach.

Example 4: Glycotype-Based Discrimination of Cancer Cells Using Isolated Anti-GAG Motif Antibody Fragments To assess whether purified anti-GAG motif antibodies or antigen binding fragments thereof could be used to differentiate between different cancer cell lines, a cell-based screening FACS assay was established that allows rapid quantification of fluorescent cells in a multi-well format. Using this platform, the differential binding of purified, His-tagged, anti-HS-motif antibodies in scFv format to a panel of five different hematopoietic cancer cell lines was determined: Murine erythroleukemia (cell line MEL), human erythroleukemia (cell line HEL), human acute monocytic leukemia (AML, cell lines MOLM-14 and THP-1), and human chronic myelogenous leukemia (CML, cell line K-562). Two non-cancerous cell lines, which do not express HSPG, are shown as controls: Murine myeloblast (cell line 32D) and murine pro-B (cell line BAF3-EpoR). The signal was detected using an anti-His, phycoerythrin (PE)-labeled secondary antibody.

Figure 4:
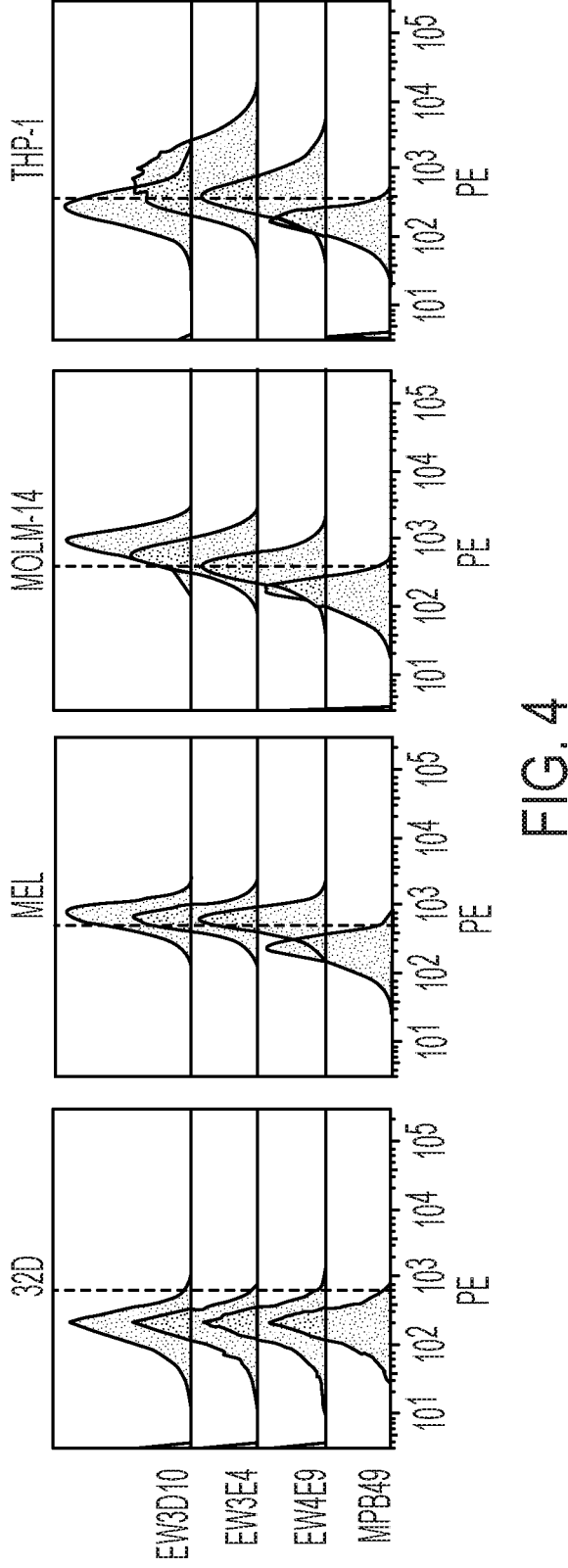
FIG. 4 shows the binding profile of 5 hematopoietic cell lines (as indicated: HEL, MEL, MOLM-14, THP-1, K-562) using purified, His-tagged scFvs. Signal was detected using a secondary anti-HIS-PE (Phycoerythrin) antibody. Cell lines 32D and BAF3-EpoR, which do not express HS proteoglycans were used as controls. scFv MPB49, which does not bind to HS, served as a control.
Figure 4:
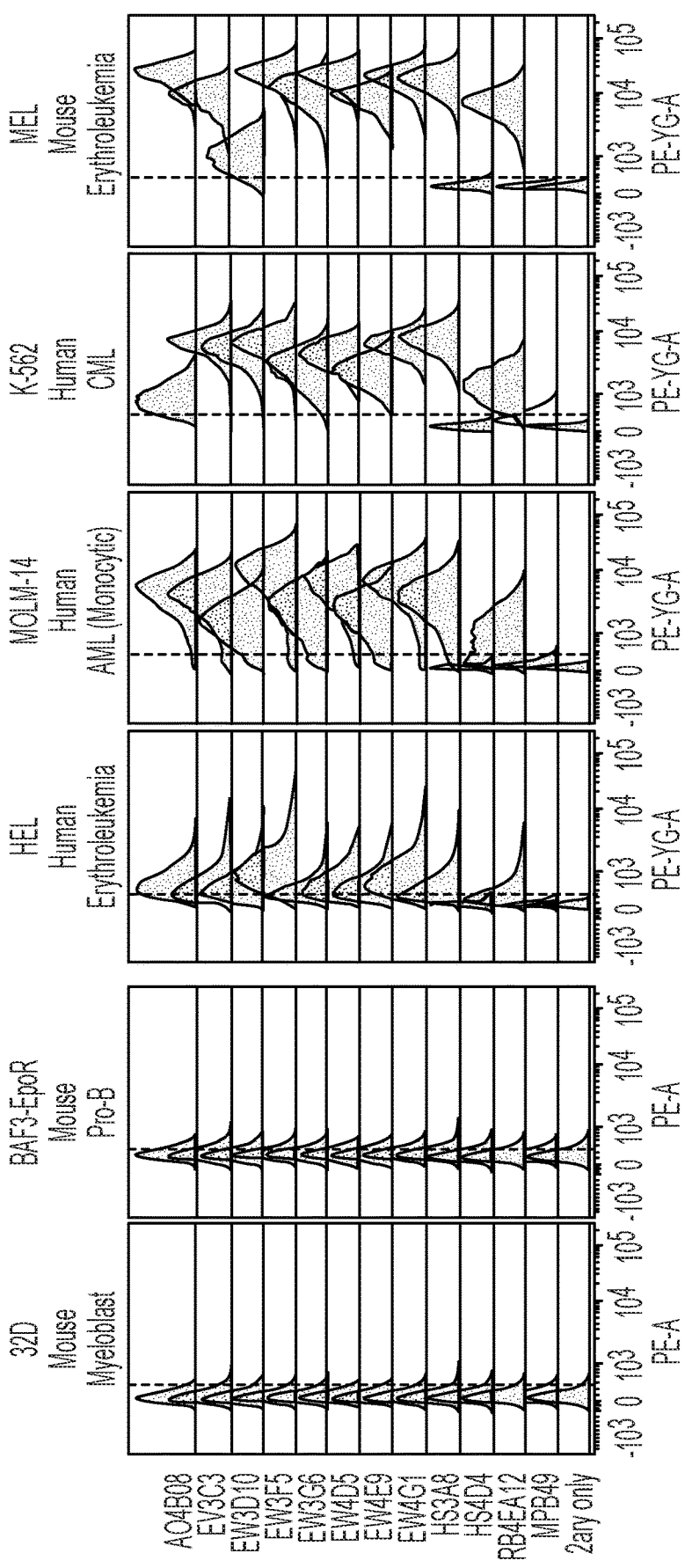

As shown in FIG. 4, each cell line shows a distinct antibody binding profile. scFv MPB49, which shows no HS binding activity, served as a negative control.

No scFv binding was observed for MEL or MOLM-14 cells treated with Heparinase, which digests heparan sulfate (but not chondroitin sulfate). Treatment of cells with chondroitinase ABC, which digests chondroitin sulfate (but not heparan sulfate), did not affect scFv binding to the cells, demonstrating that the binding of the scFvs in the FACS cell sorting experiments indeed rely on binding to heparan sulfate and not on some other, unknown potential epitope.

In summary, these data illustrate that anti-GAG motif antibodies and antigen binding fragments thereof are powerful tools to detect and discriminate between clinically relevant pathogenic and healthy cell types, both from human as well as murine origin.

Figure 5A:
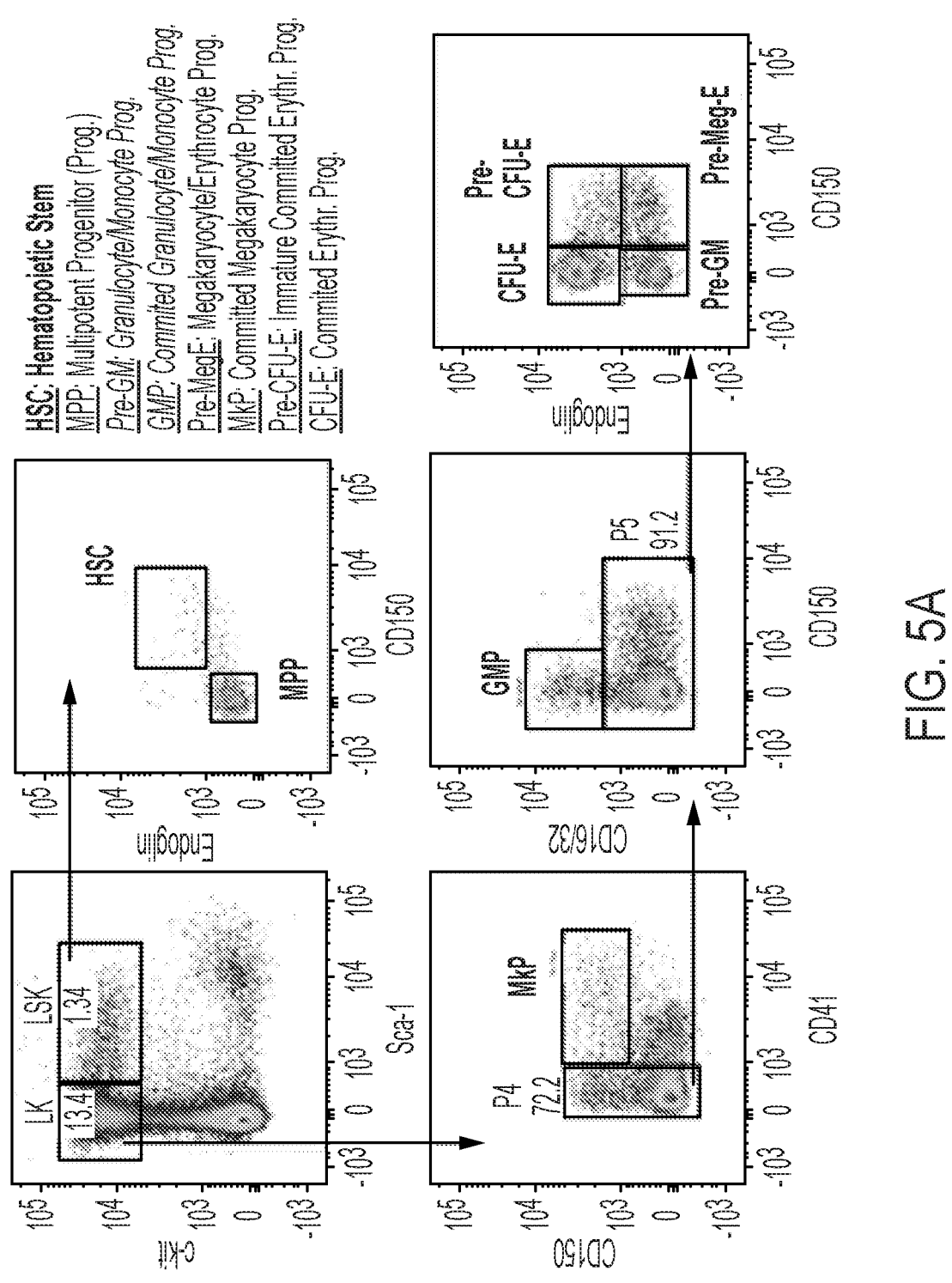
FIG. 5A shows the gating schema for the isolation of hematopoietic bone marrow stem and progenitor cell (HSPC) populations.
Figure 5B:
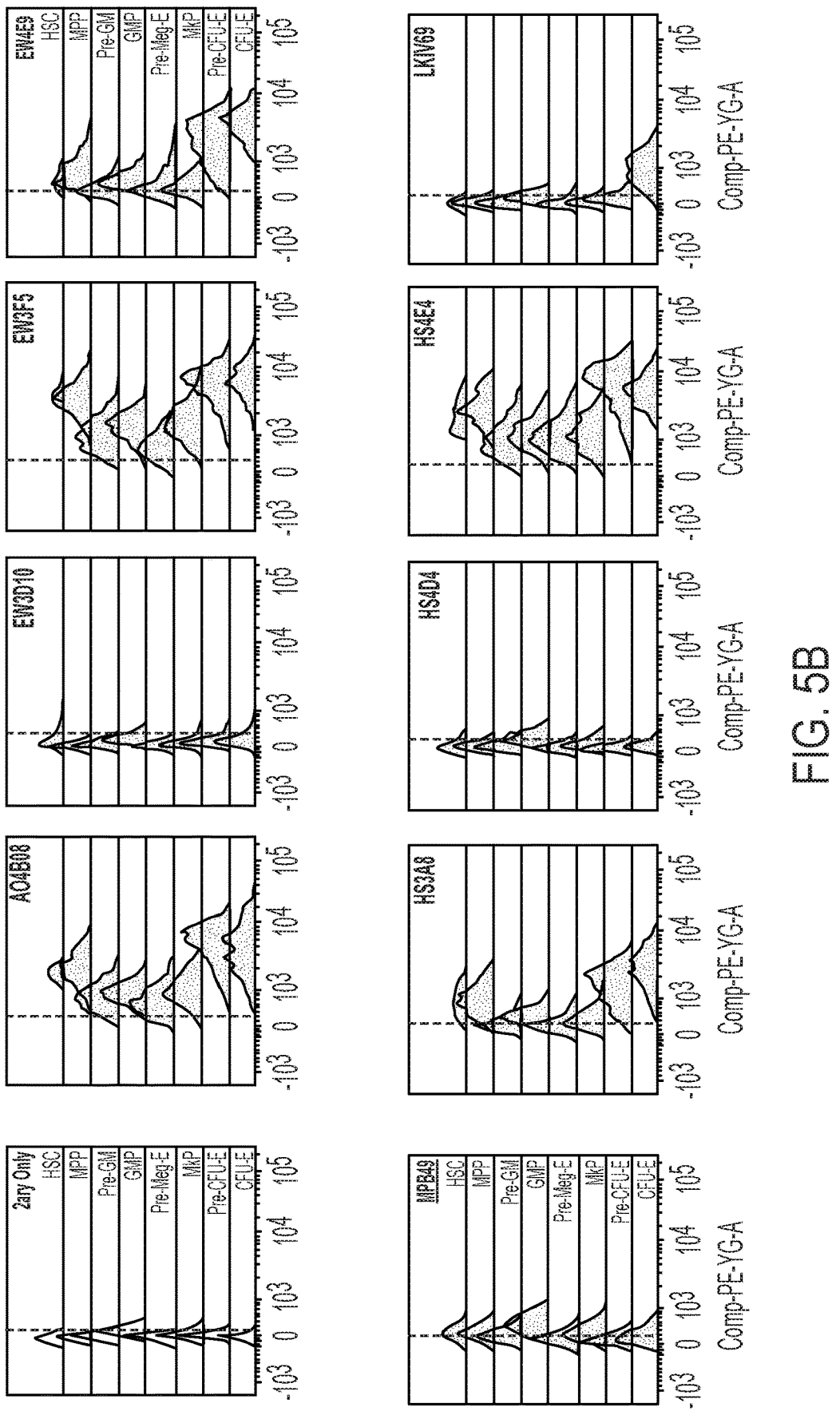
FIG. 5B shows HS profiling of various HSPC populations using different purified, His-tagged anti-HS motif antibodies in scFv format. MPB49 served as a negative control. Signal was detected using a secondary anti-His-PE antibody. HSC=hematopoietic stem cells. MPP=multipotent progenitor cells. Pre-GM: Granulocyte/monocyte progenitor cells. GMP=Committed granulocyte/monocyte progenitor cells. Pre-MegE=Megakaryocyte/Erythrocyte progenitor cells. MkP=Committed megakaryocyte progenitor cells. Pre-CFU-E=Immature committed erythrocyte progenitor cells. CFU-E=Committed erythrocyte progenitor cells.

Example 5: Discrimination of Murine Primary Hematopoietic Stem and Progenitor Cells Based on their Glycotype Using Isolated Anti-GAG Motif Antibody Fragments Next, purified, His-tagged, anti-HS motif antibodies in scFv format were used to determine the anti-HS motif antibody binding profiles for a well-characterized gating scheme of murine primary hematopoietic stem and progenitor cells of different lineage commitments. As shown in FIG. 5, these cell populations show significant differences in anti-HS motif antibody binding.

These data indicate that even with a limited set of anti-HS motif antibodies, binding patterns could be identified that differ both quantitatively and qualitatively among the different cell types that could not be discriminated using existing proteinaceous cell surface makers (e.g. CD system).

Example 6: Sorting of Cell Populations Based on their Glycotype

Figure 6:
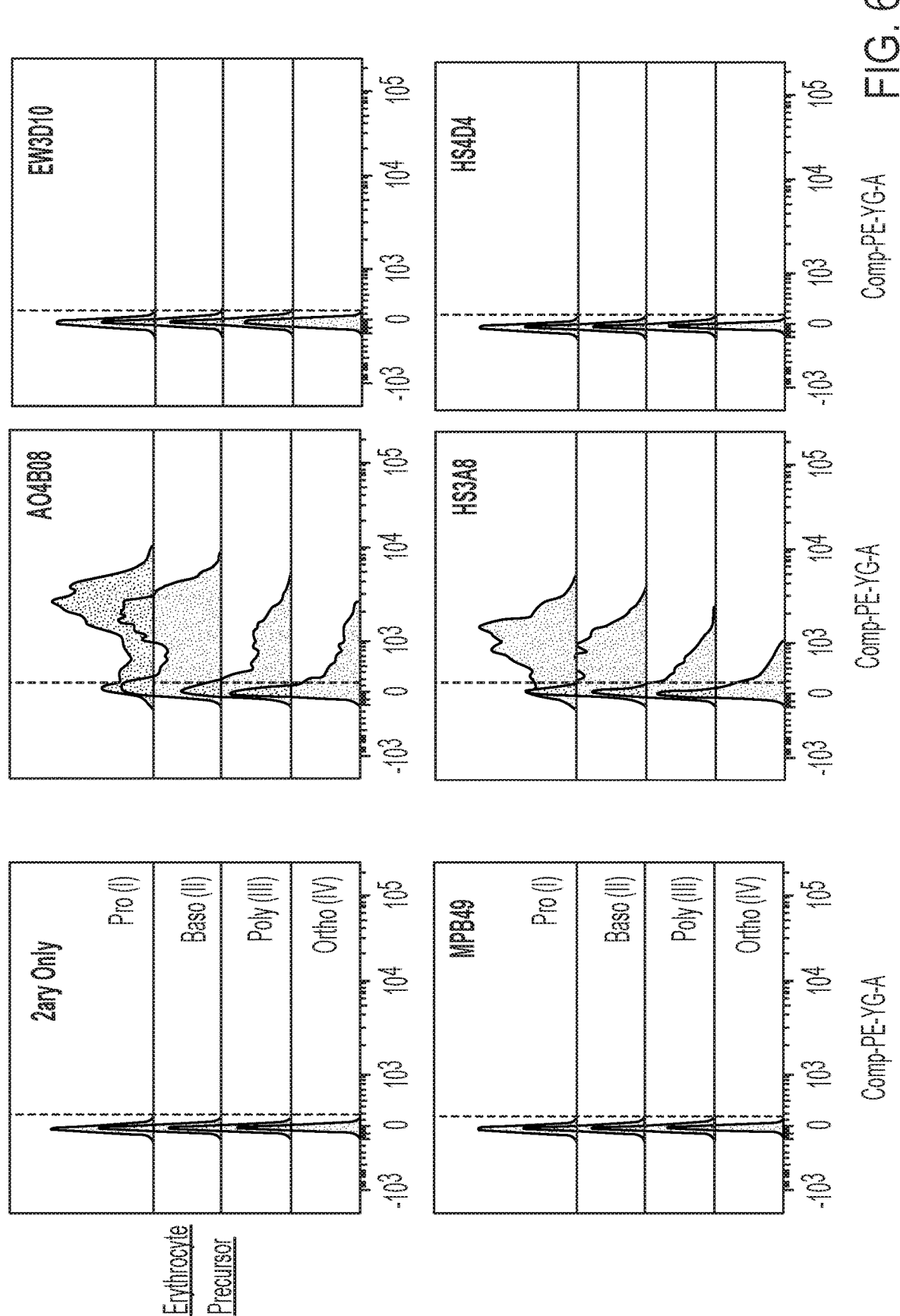
FIG. 6 shows differential HS profiling of erythrocytes and megakaryotes by anti-HS motif antibodies. HS profiling was performed using purified, His-tagged anti-HS motif antibodies in scFv format. Signal was detected using a secondary anti-His-PE antibody.
Figure 6:
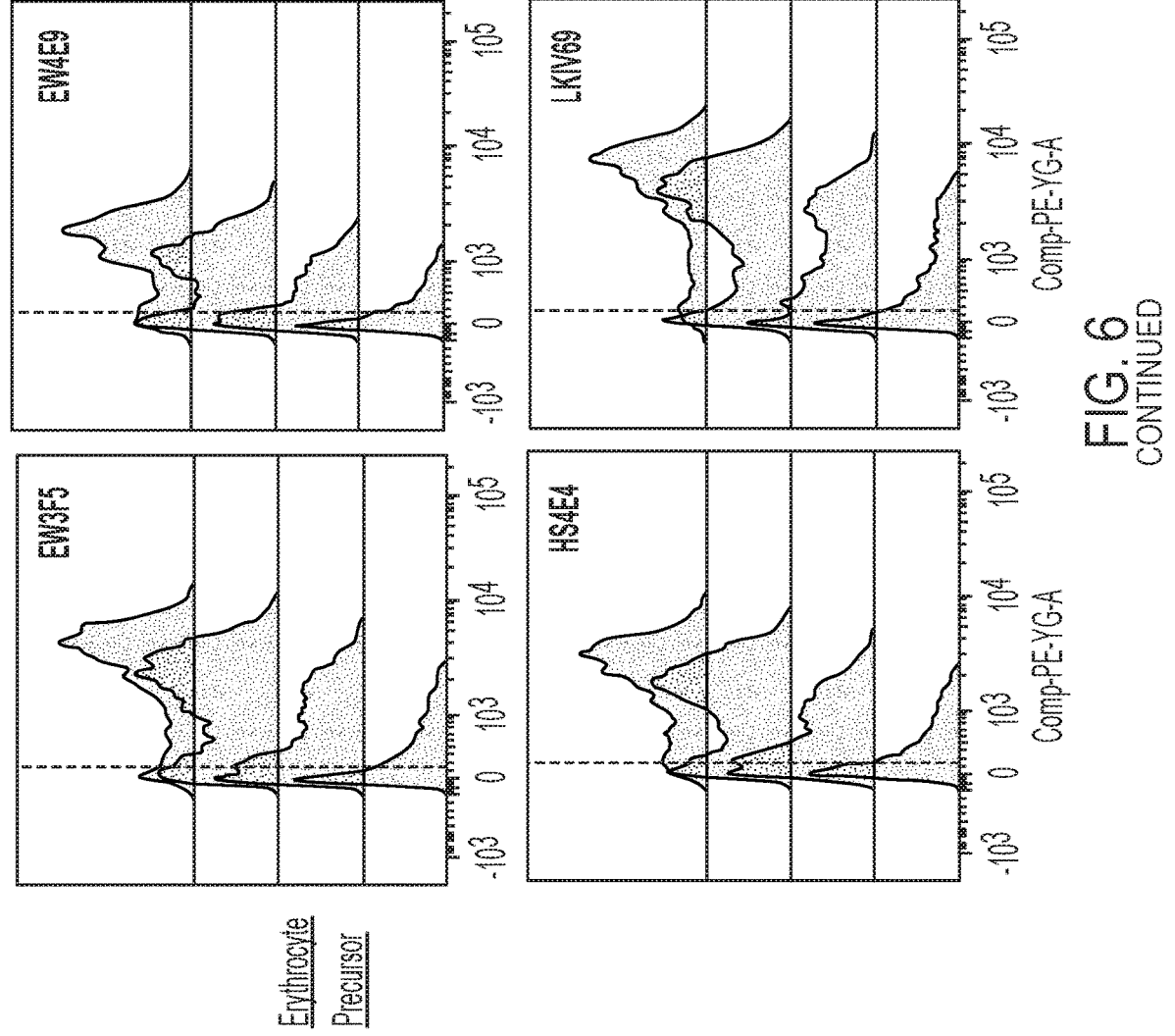
Figure 6:
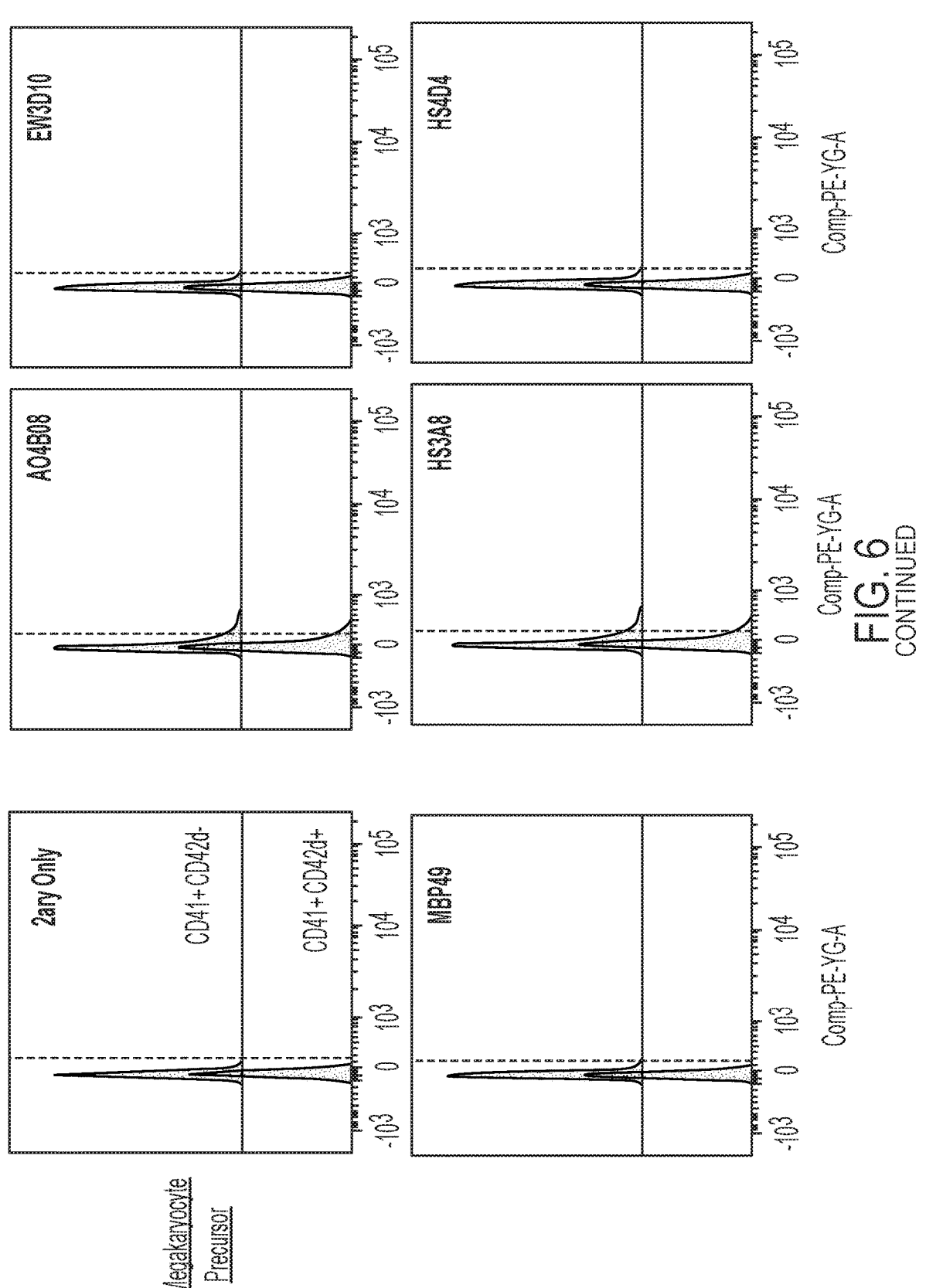
Figure 6:
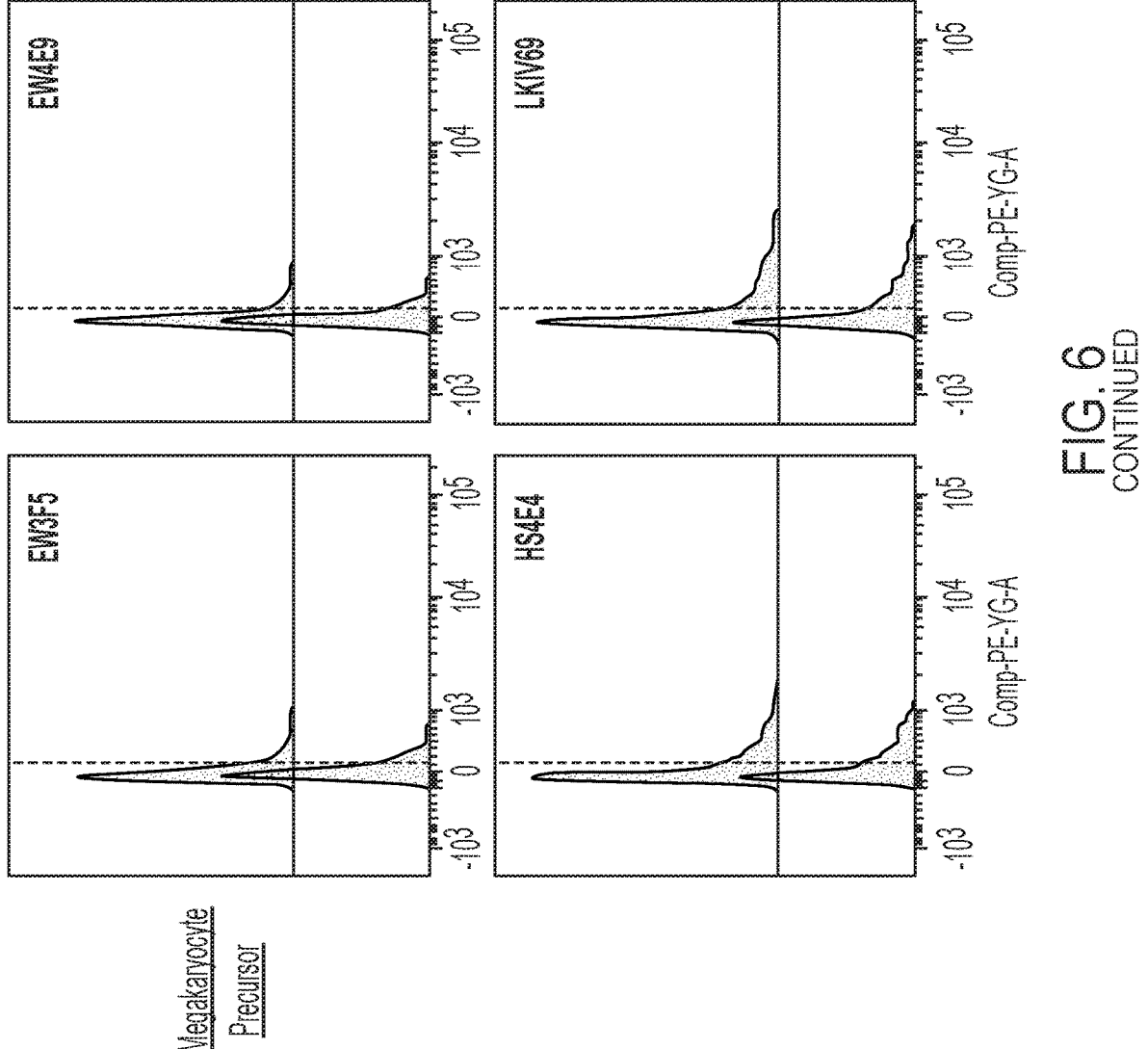

To demonstrate that anti-GAG motif antibodies and antigen binding fragments thereof can be used to sort cell populations and assign functional characteristics to these populations, murine megakaryocyte precursors were isolated based on their anti-HS motif antibody binding profile. As shown in FIG. 6, megakaryocytes and erythrocytes and their precursors display differential binding to purified, His-tagged anti-HS motif scFvs.

Figure 7A:
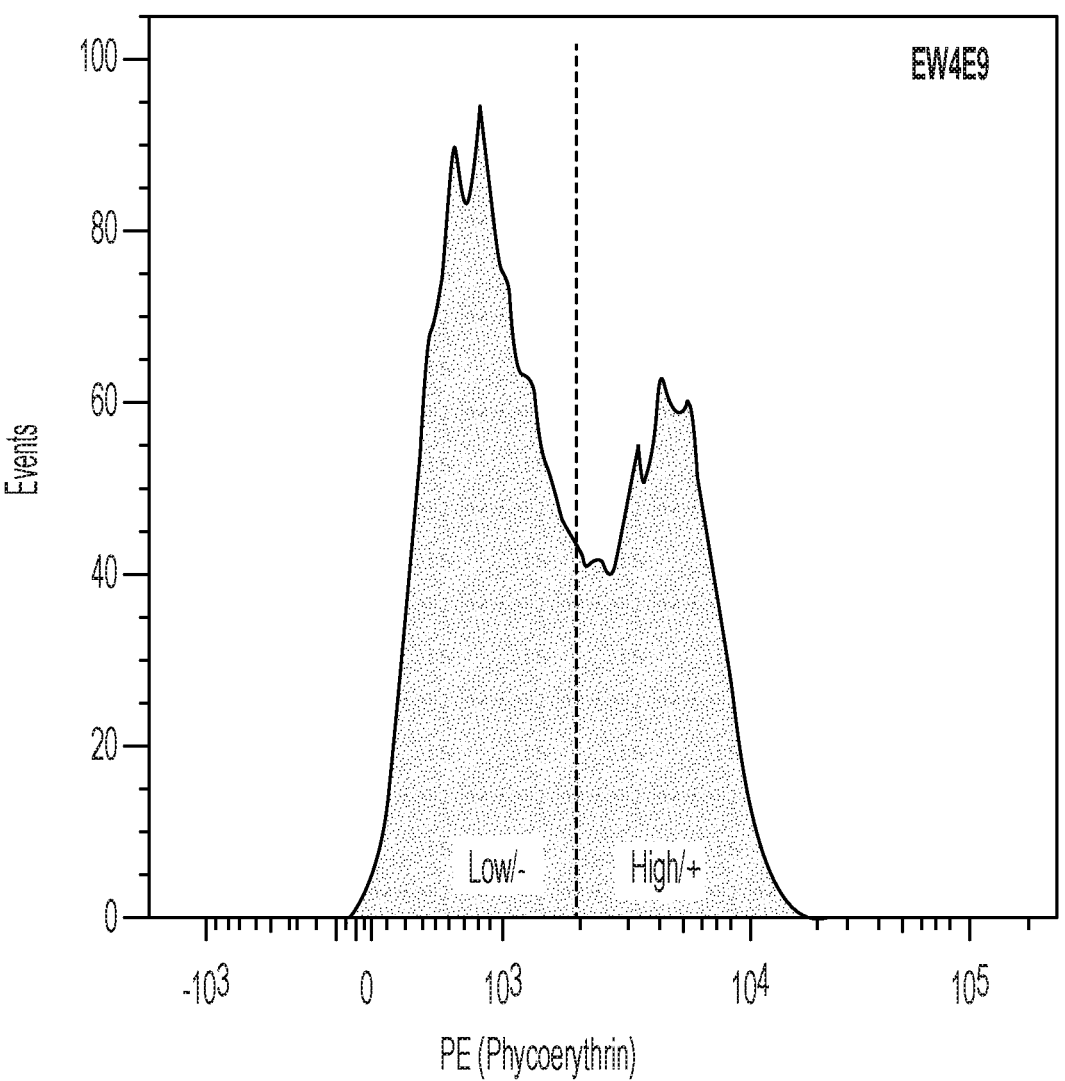
FIG. 7A shows sorting of total c-kit$^+$ bone marrow cells using the HS-specific scFv EW4E9.

Total c-kit+ bone marrow cells were sorted by FACS using anti-HS scFvs EW5F5, HS3A8, and EW4E9, which bind to erythrocyte precursors, but not to megakaryocyte precursors (see FIG. 6 and FIG. 7A). Megakaryocyte colonies were detected using MegaCult™-C, a collagen-based culture system for colony-forming unit (CFU) assays of megakaryocyte progenitors (STEMCELL Technologies) following the manufacturer's instructions.

Figure 7B:
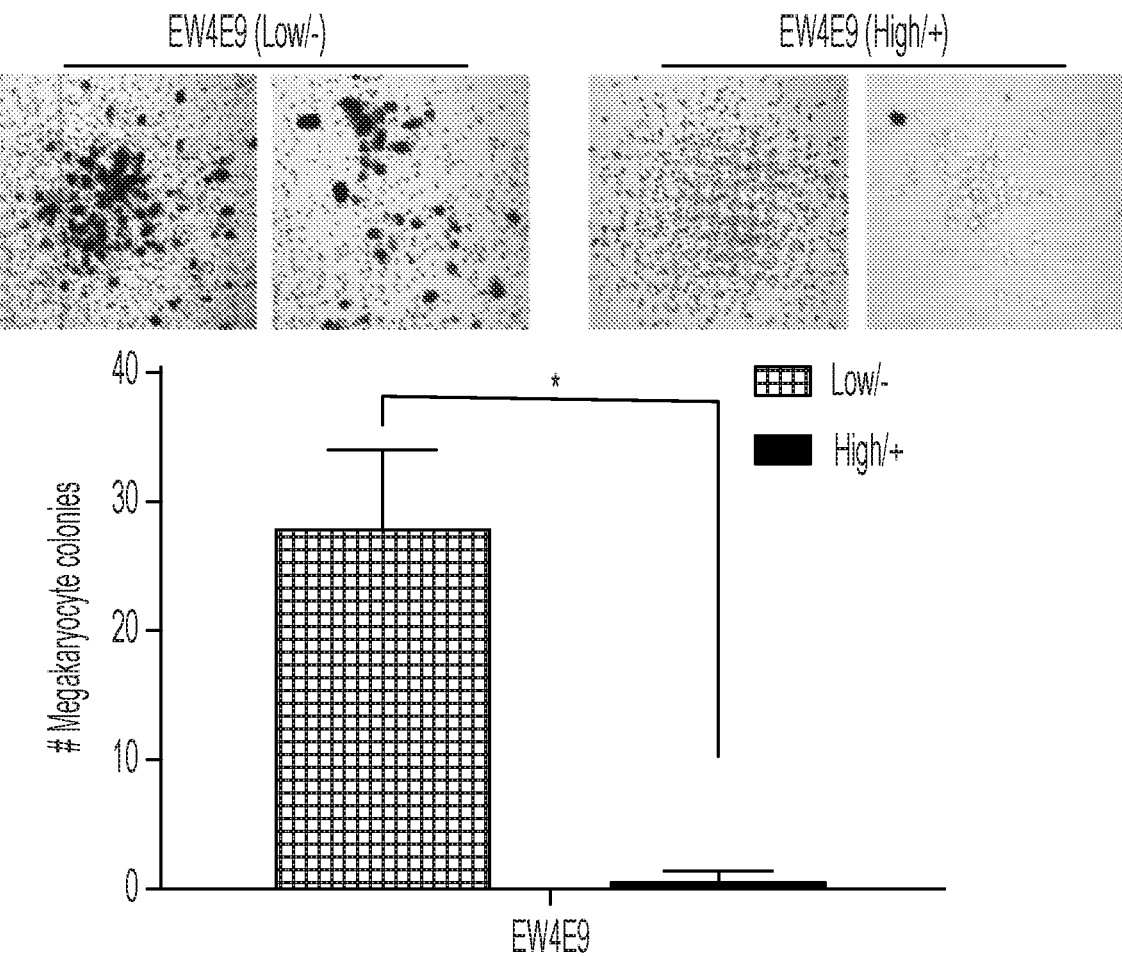
FIG. 7B shows the results of a megakaryocyte forming assay for the two cell populations shown in FIG. 7A. Statistical significance is indicated (*=0.02).

Representative results are shown for scFv EW4E9. Acetylcholinesterase-positive megakaryocyte-forming colonies (FIG. 7B, left, upper panel) reside exclusively in cells negative/low for EW4E9 (quantified in (FIG. 7B, lower panel), whereas cells with high EW4E9 binding form no colonies (FIG. 7B, right, upper panel).

These experiments demonstrate that the anti-GAG motif antibodies and antigen binding fragments can be used to effectively differentiate between blood cell types of different provenance, even for cells that could not previously be further differentiated using the CD system. The data also underscores the utility of the anti-GAG motif antibodies and antigen binding fragments for the isolation of populations of live cells for further phenotypic and functional studies.

Figures 8A, 8B:
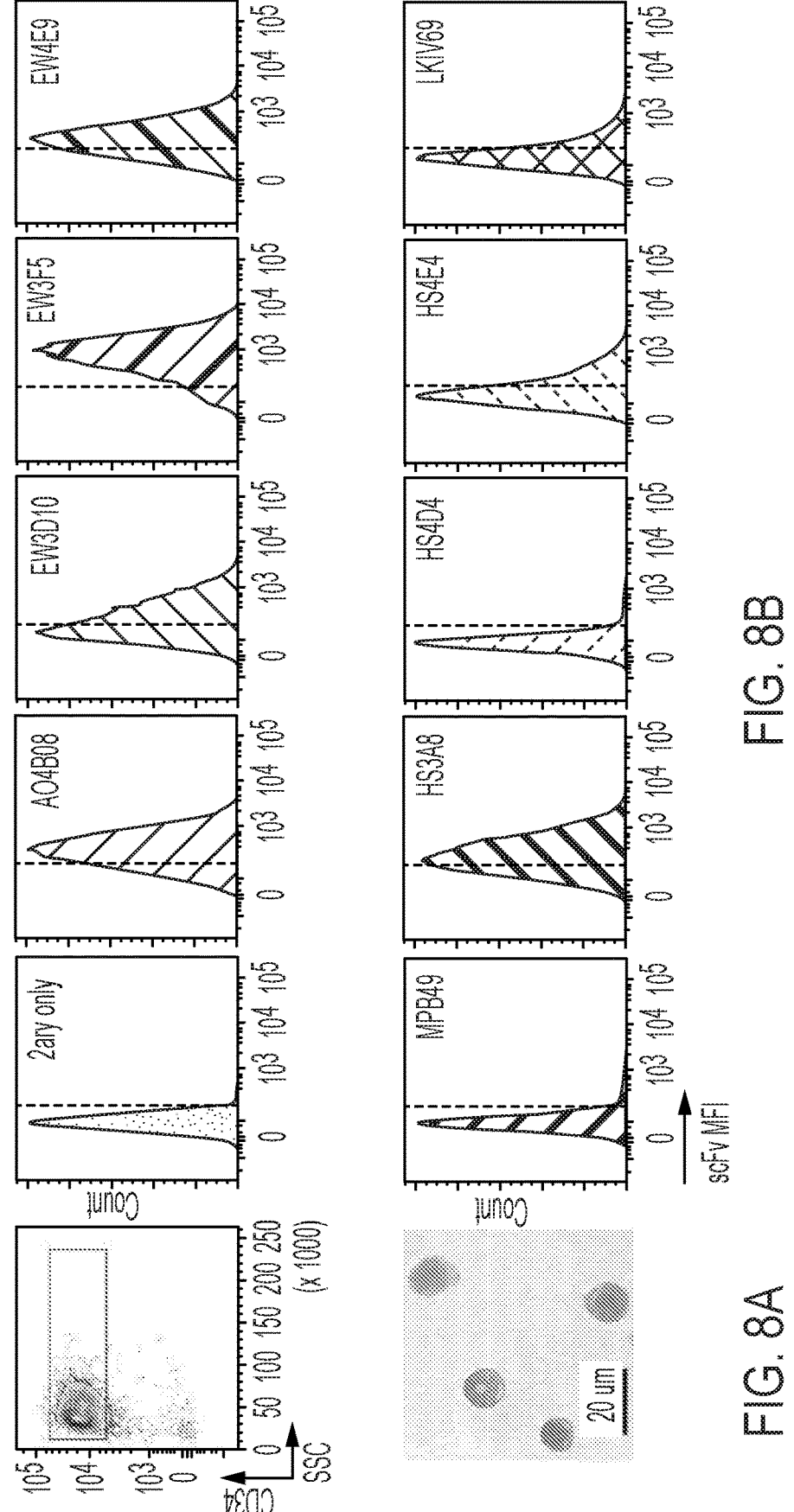
FIG. 8B shows histograms of HS scFv binding to human CD34$^+$ cells.
Figure 9:
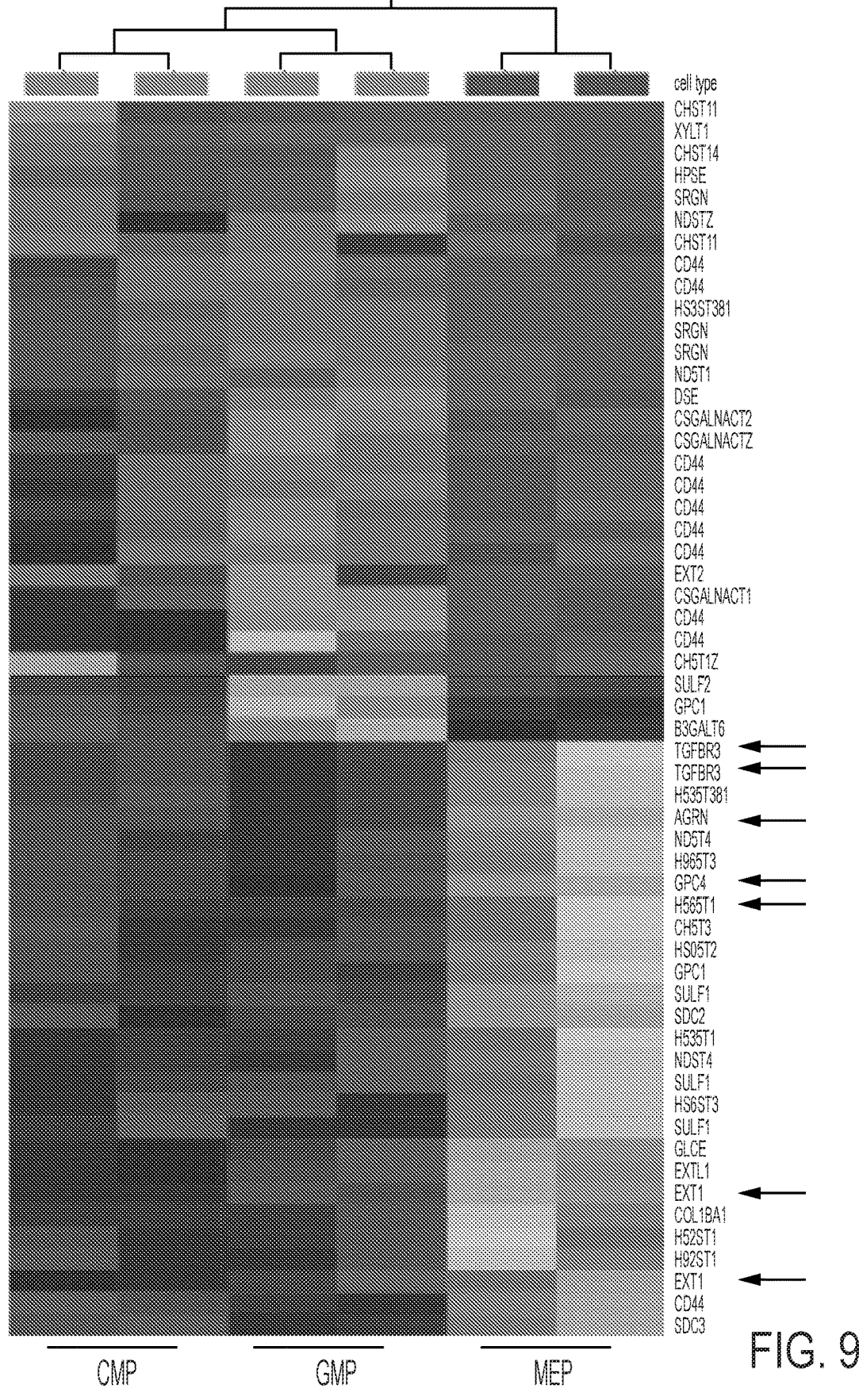
FIG. 9 illustrates that HS-related genes are significantly differentially expressed within human common myeloid progenitor cell (CMP), granulocyte-monocyte progenitor (GMP), and megakaryocyte-erythrocyte progenitors (MEP) populations from GSE19599 (gene expression profiling of normal hematopoietic cell subpopulations; Andersson et al. *BMCMed Genomics* 2010 Mar. 8; 3:6).

Example 7: Anti-GAG Motif Antibody Fragments can be Used to Identify Conserved HS Modification Patterning in Mice and Humans with Regards to Megakaryocyte and Erythroid Lineage Commitment Next, the utility of using anti-GAG motif antibodies and antigen binding fragments to interrogate HS modification patterns within human progenitors and their subsequent differentiation into megakaryocyte and erythroid lineages was demonstrated. Glycotyping of human CD34$^+$HSPCs showed binding of the HS scFv panel was very similar to the binding previously observed in mouse HSPCs (FIGS. 5 and 8 and Examples 5 and 6). Additionally, analysis of publicly available gene expression data from sorted human progenitors revealed the same HS gene targets that were identified in mice as enriched within megakaryocyte-erythrocyte progenitors (MEPs) compared to multipotent common myeloid progenitor cell (CMP) and granulocyte-monocyte progenitor (GMP) populations (FIG. 9), showing a conserved HS modification patterning in mice and humans with regards to megakaryocyte and erythroid lineage commitment. To further corroborate this finding, in vitro megakaryocytic or erythroid differentiation experiments with human CD34$^+$ cells were performed. A temporal and dynamic patterning of HS scFv binding during human erythroid commitment was observed. Also observed were low, minimally changing levels of HS scFv binding during megakaryocyte differentiation that resembled the prior observations in the murine system (data not shown).

Figure 10A:
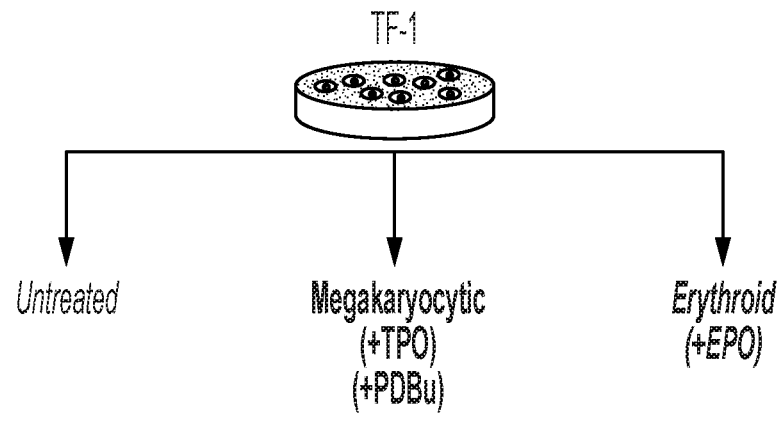
FIG. 10A provides a schematic of TF-1 differentiation into erythroid and megakaryocytic cells.
Figure 10B:
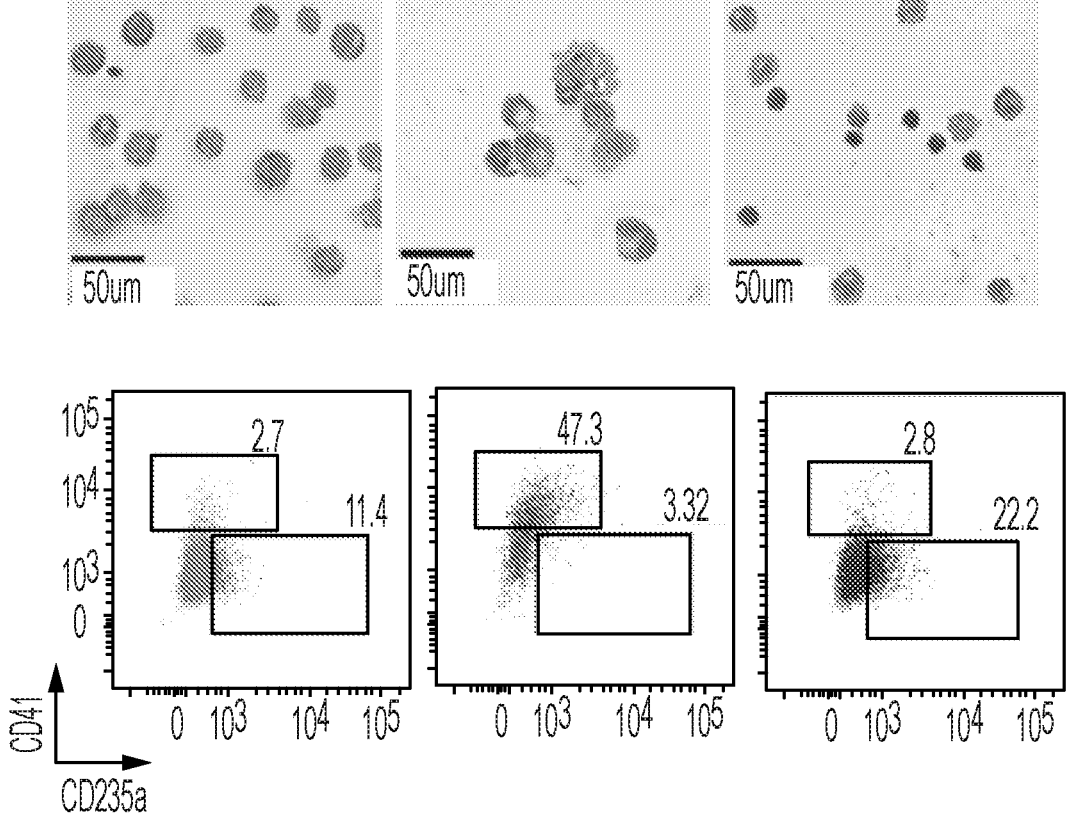
FIG. 10B illustrates the morphological (upper panels) and immunophenotypic (lower panels) validation of erythroid and megakaryocyte differentiation of TF-1 cells.
Figure 10C:
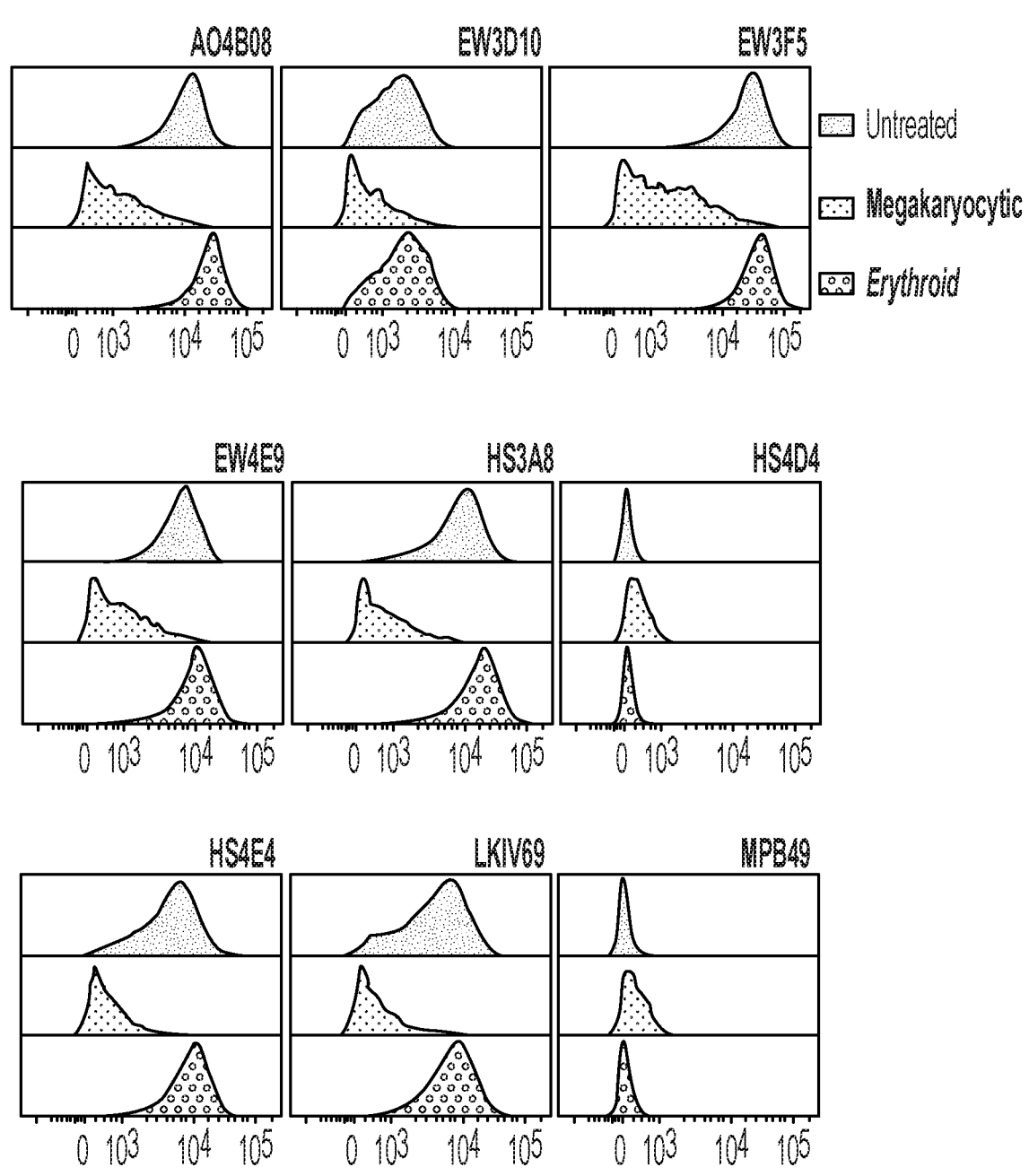
FIG. 10C shows representative histograms of HS scFv binding of TF-1 cells in parental (grey), megakaryocyte (green) and erythroid (red) differentiation conditions. (n=3).

Finally, a longitudinal differentiation assay utilizing the bi-potent (erythroid/megakaryocytic) TF-1 cell line revealed diminished HS scFv binding during megakaryocyte differentiation as well as elevated binding upon erythroid commitment (FIG. 10).

Taken together, these data demonstrate conserved HS modification patterning within hematopoietic progenitors and specifically during megakaryocyte and erythroid differentiation in humans and mice.

Prophetic Example 1: Determination of Cellular Glycotypes

To further validate that anti-GAG motif antibodies and antigen binding fragments thereof can be used to glycotype hematopoietic cell lineages, a panel of 18 hematopoietic cell lines are screened, including cell types of the different major lineages (T lymphoid, B lymphoid, myeloid, monocytic, megakaryocytic, erythroid). 3 lines each are included for every major lineage, and cell lines of both sexes are included (T cell lines: JURKAT, LOUCY, MOLT-16; B cell lines: OCI-Ly1, REH, SU-DHL-16; myeloid cell lines: HL60, 32D, Kasumi-1; monocytic cell lines: MONO-MAC-6, MOLM14, THP-1; megakaryocytic cell lines: CMK, M-07e, MEG-01; erythroid cell lines: MEL, HEL, TF-1). These cell lines are used to establish multiplexing applications of selected HS-specific scFvs that uniquely label certain cell lines.

Additionally, several hematopoietic cell lines have the ability to differentiate upon treatment with differentiating agents and cytokines e.g. 32D (model for granulocyte differentiation), K-562 (megakaryocyte and erythroid differentiation). After glycotyping the parental cells of these lines using anti-GAG motif antibodies or antigen binding fragments thereof, the HS landscape of these cells are characterized as they differentiate down their respective lineages.

Establishing a panel of fully-characterized hematopoietic cell lines using anti-GAG motif antibodies or antigen binding fragments thereof provides insight into the HS profile of hematopoietic cells in the setting of differentiation, and furthermore, attributes unique HS profiles to phenotypically distinct hematopoietic lineages and maturation stages.

Prophetic Example 2: Comparison of Glycotype with Established Cellular Classification Systems To compare the cellular glycotype as determined using anti-GAG motif antibodies or antigen binding fragments thereof with a validated cellular classification system, primary hematopoietic cells are glycotyped systematically and their glycotypes compared to existing CD markers.

Specifically, bone marrow cells from wild-type C57BL/6 mice (both sexes will be included) are used in combination with bona fide CD surface markers. The individual scFvs are screened against hematopoietic cell populations delineated by well-established and functionally validated CD marker-based gating schemas using flow cytometry. Leveraging the CD marker system, the HS-specific scFv binding of highly enriched stem and progenitor populations, as well as their terminally differentiated counterparts (including CD 3 —T cells, B220 —B cells, Gr-1 —granulocytes, CD11b/Mac-1 —monocytes, Ter 19 —erythrocytes, CD41/61 —megakaryocytes, etc.) are queried. The glycotype approach allows to further sub-distinguish primary cells within a given CD marker gated population. The isolated subpopulations are characterized functionally using in vitro colony-forming assays in semisolid methylcellulose-based media as well as in vivo transplantation assays of isolated populations with different scFv binding profiles into congenic recipient mice.

The invention claimed is:

1. A method of separating a target cell from a population of cells based on the target cell's glycosaminoglycan (GAG) glycotype, the method comprising:

(a) contacting a mixture comprising the target cell and the population of cells with three or more anti-GAG motif antibodies or antigen-binding fragments thereof that bind to three or more GAG motifs on the surface of the target cell; and (b) separating the target cell from the population of cells, wherein:

the target cell has a GAG glycotype that is different from the GAG glycotype for the population of cells;

each of the anti-GAG motif antibodies or antigen-binding fragments thereof comprises a heavy variable chain comprising a CDR1H, CDR2H, and CDR3H;

each of the anti-GAG motif antibodies or antigen-binding fragments thereof comprises a light variable chain comprising a CDR1L, CDR2L, and CDR3L; and the three or more anti-GAG motif antibodies or antigen-binding fragments thereof are selected from the group consisting of:

(i) an anti-GAG antibody or antigen-binding fragment thereof comprising a CDR1H comprising SYAMS (SEQ ID NO:85), a CDR2H comprising AISGSGG-STYYADSVKG (SEQ ID NO:86), a CDR3H comprising SLRMNGWRAHQ (SEQ ID NO:43), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(ii) an anti-GAG antibody or antigen-binding fragment thereof comprising a CDR1H comprising SYAMS (SEQ ID NO:85), a CDR2H comprising AISGSGG-STYYADSVKG (SEQ ID NO:86), a CDR3H comprising SISMNGVGVRIQ (SEQ ID NO:46), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(iii) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising SGRQARQGRFPK (SEQ ID NO:49), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(iv) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising LRGTKMFRH (SEQ ID NO:59), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(v) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GKVKLPN (SEQ ID NO:62), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(vi) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GMRPRL (SEQ ID NO:64), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(vii) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GRRLKD (SEQ ID NO:68), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(viii) an anti-GAG antibody or antigen-binding fragment thereof comprising a CDR1H comprising SYEMN (SEQ ID NO:92), a CDR2H comprising YISSSG-STIYYADSVKG (SEQ ID NO:93), a CDR3H comprising GMRPRL (SEQ ID NO:64), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(ix) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising HAPLRNTRTNT (SEQ ID NO:71), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(x) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GSRSSR (SEQ ID NO:72), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89); and (xi) an anti-GAG antibody or antigen-binding fragment thereof comprising a CDR1H comprising DYGMS (SEQ ID NO:94), a CDR2H comprising GINWNGG-STGYADSVKG (SEQ ID NO:95), a CDR3H comprising RRYALDY (SEQ ID NO:75), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xii) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GKMKLNR (SEQ ID NO:44), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xiii) an anti-GAG antibody or antigen-binding fragment thereof comprising a CDR1H comprising SNYMS (SEQ ID NO:108), a CDR2H comprising VIYSGG-STYYADSVKG (SEQ ID NO:109), a CDR3H comprising GYRPRF (SEQ ID NO:45), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xiv) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GRTVGRN (SEQ ID NO:47), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89), (xv) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising DRRNTQKTRYRT (SEQ ID NO:48), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xvi) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GGTTRIRK (SEQ ID NO:50), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xvii) an anti-GAG antibody or antigen-binding fragment thereof comprising a CDR1H comprising GYYMH (SEQ ID NO:119), a CDR2H comprising WINPNSGGTNYAQKFQG (SEQ ID NO:110), a CDR3H comprising GTKLKMTK (SEQ ID NO:51), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xviii) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising ERNTIRR (SEQ ID NO:52), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89), (xix) an anti-GAG antibody or antigen-binding fragment thereof comprising a CDR1H comprising SYAMH (SEQ ID NO:115), a CDR2H comprising AIGTGGGTYYADSVKG (SEQ ID NO:111), a CDR3H comprising GRLHLPRK (SEQ ID NO:53), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xx) an anti-GAG antibody or antigen-binding fragment thereof comprising a CDR1H comprising GYYMH (SEQ ID NO: 119), a CDR2H comprising WINPNSGGTNYAQKFQ (SEQ ID NO:113), a CDR3H comprising SSSRHHRLHR (SEQ ID NO:54), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxi) an anti-GAG antibody or antigen-binding fragment thereof comprising a CDR1H comprising SYAMH (SEQ ID NO:115), a CDR2H comprising WINAGNG-NTKYSQKFQG (SEQ ID NO:114), a CDR3H comprising QRWKPAVTPKLV (SEQ ID NO:44), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxii) an anti-GAG antibody or antigen-binding fragment thereof comprising a CDR1H comprising SYAMH (SEQ ID NO:115), a CDR2H comprising AIGTGGGTYYADSVKG (SEQ ID NO:111), a CDR3H comprising ARMTGHVRNVMI (SEQ ID NO:56), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxiii) an anti-GAG antibody or antigen-binding fragment thereof comprising a CDR1H comprising SYAMH (SEQ ID NO:115), a CDR2H comprising AIGTGGGTYYADSVKG (SEQ ID NO:111), a CDR3H comprising PVSHRKWRVTV (SEQ ID NO:57), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxiv) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GRRHKLIR (SEQ ID NO:58), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxv) an anti-GAG antibody or antigen-binding fragment thereof comprising a CDR1H comprising DYYMH (SEQ ID NO: 118), a CDR2H comprising LVDPEDGETIYAEKFQG (SEQ ID NO: 112), a CDR3H comprising SRKTPKPFMRK (SEQ ID NO:60), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxvi) an anti-GAG antibody or antigen-binding fragment thereof comprising a CDR1H comprising SNYMS (SEQ ID NO:108), a CDR2H comprising VIYSGG-STYYADSVKG (SEQ ID NO:109), a CDR3H comprising GARLKR (SEQ ID NO:61), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxvii) an anti-GAG antibody or antigen-binding fragment thereof comprising a CDR1H comprising SYAMH (SEQ ID NO:115), a CDR2H comprising AIGTGGGTYYADSVKG (SEQ ID NO:111), a CDR3H comprising GTKKLGK (SEQ ID NO:63), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxviii) an anti-GAG antibody or antigen-binding fragment thereof comprising a CDR1H comprising DYYMH (SEQ ID NO:118), a CDR2H comprising LVDPEDGETIYAEKFQG (SEQ ID NO:112), a CDR3H comprising SRKTRKPFMRK (SEQ ID NO:65), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:892;

(xxix) an anti-GAG antibody or antigen-binding fragment thereof comprising a CDR1H comprising GYYMH (SEQ ID NO:119), a CDR2H comprising WINPNSGGTNYAQKFQG (SEQ ID NO:110), a CDR3H comprising YYHYKVN (SEQ ID NO:66), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxx) an anti-GAG antibody or antigen-binding fragment thereof comprising a CDR1H comprising SGGYYWS (SEQ ID NO:120), a CDR2H comprising YIYYSG-STYYNPSLKS (SEQ ID NO:116), a CDR3H comprising WVTEP (SEQ ID NO:67), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxxi) an anti-GAG antibody or antigen-binding fragment thereof comprising a CDR1H comprising SNYMS (SEQ ID NO:108), a CDR2H comprising VIYSGG-STYYADSVKG (SEQ ID NO:109), a CDR3H comprising SLRMNGCGAHQ (SEQ ID NO:70), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxxii) an anti-GAG antibody or antigen-binding fragment thereof comprising a CDR1H comprising SYAMS (SEQ ID NO:85), a CDR2H comprising AIS-GSGGSTYYADSVKG (SEQ ID NO:86), a CDR3H comprising QKKRPRF (SEQ ID NO:73), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89), (xxxiii) an anti-GAG antibody or antigen-binding fragment thereof comprising a CDR1H comprising SYWMH (SEQ ID NO:117), a CDR2H comprising RINSDGSSTTYADSVKG (SEQ ID NO:124), a CDR3H comprising SGRKGRMR (SEQ ID NO:74), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxxiv) an anti-GAG antibody or antigen-binding fragment thereof comprising a CDR1H comprising SYYMH (SEQ ID NO:121), a CDR2H comprising IINPSGGTSYAQKFQG (SEQ ID NO:122), a CDR3H comprising AMTQKKPRKLSL (SEQ ID NO:77), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(xxxv) an anti-GAG antibody or antigen-binding fragment thereof comprising a CDR1H comprising YRYLH (SEQ ID NO:125), a CDR2H comprising WITPFNGNTNYAQKFQD (SEQ ID NO:123), a CDR3H comprising SGRKYFRARDMN (SEQ ID NO:78), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89); and (xxxvi) an anti-GAG antibody or antigen-binding fragment thereof comprising a CDR1H comprising SYWMH (SEQ ID NO:117), a CDR2H comprising RINSDGSSTTYADSVKG (SEQ ID NO:124), a CDR3H comprising LKQQGIS (SEQ ID NO:76), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89).

2. The method according to claim 1, wherein at least one of the one-three or more anti-GAG motif antibodies or antigen-binding fragments thereof comprises an affinity tag.

3. The method according to claim 2, the method further comprising a step of contacting the target cell bound to the one three or more anti-GAG motif antibodies or antigen binding fragments thereof with a medium that has a higher affinity for the affinity tag than the population of cells.

4. The method according to claim 1, wherein at least one of the three or more anti-GAG motif antibodies or antigen-binding fragments thereof is conjugated to a detectable moiety, an affinity tag, a magnetic moiety, or a combination thereof.

5. The method according to claim 4, wherein the detectable moiety is fluorescent.

6. The method according to claim 1, wherein at least one of the ene three or more anti-GAG motif antibodies or antigen-binding fragments thereof is conjugated to a Sortase motif.

7. The method of claim 1, wherein the three or more anti-GAG motif antibodies or antigen-binding fragments thereof are selected from the group consisting of:

(i) an anti-GAG antibody or antigen-binding fragment thereof comprising a CDR1H comprising SYAMS (SEQ ID NO:85), a CDR2H comprising AISGSGG-STYYADSVKG (SEQ ID NO:86), a CDR3H comprising SLRMNGWRAHQ (SEQ ID NO:43), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(ii) an anti-GAG antibody or antigen-binding fragment thereof comprising a CDR1H comprising SYAMS (SEQ ID NO:85), a CDR2H comprising AISGSGG-STYYADSVKG (SEQ ID NO:86), a CDR3H comprising SISMNGVGVRIQ (SEQ ID NO:46), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(iii) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising SGRQARQGRFPK (SEQ ID NO:49), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(iv) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising LRGTKMFRH (SEQ ID NO:59), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(v) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GKVKLPN (SEQ ID NO:62), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(vi) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GMRPRL (SEQ ID NO:64), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(vii) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GRRLKD (SEQ ID NO:68), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(viii) an anti-GAG antibody or antigen-binding fragment thereof comprising a CDR1H comprising SYEMN (SEQ ID NO:92), a CDR2H comprising YISSSG-STIYYADSVKG (SEQ ID NO:93), a CDR3H comprising GMRPRL (SEQ ID NO:64), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(ix) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising HAPLRNTRTNT (SEQ ID NO:71), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89);

(x) an anti-GAG antibody or antigen-binding fragment thereof comprising a CDR1H comprising NAWMS (SEQ ID NO:90), a CDR2H comprising RIK-SKTDGGTTDYAAPVKG (SEQ ID NO:91), a CDR3H comprising GSRSSR (SEQ ID NO:72), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89); and (xi) an anti-GAG antibody or antigen-binding fragment thereof comprising a CDR1H comprising DYGMS (SEQ ID NO:94), a CDR2H comprising GINWNGG-STGYADSVKG (SEQ ID NO:95), a CDR3H comprising RRYALDY (SEQ ID NO:75), a CDR1L comprising QGDSLRSYYAS (SEQ ID NO:87), a CDR2L comprising GKNNRPS (SEQ ID NO:88), and a CDR3L comprising NSRDSSGNHVV (SEQ ID NO:89).

8. The method of claim 7, wherein the three or more anti-GAG motif antibodies or antigen-binding fragments thereof are selected from the group consisting of:

(i) an anti-GAG motif antibody or antigen-binding fragment thereof comprising a heavy variable chain comprising SEQ ID NO:96 and a light variable chain comprising SEQ ID NO:97;

(ii) an anti-GAG motif antibody or antigen-binding fragment thereof comprising a heavy variable chain comprising SEQ ID NO:98 and a light variable chain comprising SEQ ID NO:97;

(iii) an anti-GAG motif antibody or antigen-binding fragment thereof comprising a heavy variable chain comprising SEQ ID NO:99 and a light variable chain comprising SEQ ID NO:97;

(iv) an anti-GAG motif antibody or antigen-binding fragment thereof comprising a heavy variable chain comprising SEQ ID NO:100 and a light variable chain comprising SEQ ID NO:97;

(v) an anti-GAG motif antibody or antigen-binding fragment thereof comprising a heavy variable chain comprising SEQ ID NO:101 and a light variable chain comprising SEQ ID NO:97;

(vi) an anti-GAG motif antibody or antigen-binding fragment thereof comprising a heavy variable chain comprising SEQ ID NO:102 and a light variable chain comprising SEQ ID NO:97;

(vii) an anti-GAG motif antibody or antigen-binding fragment thereof comprising a heavy variable chain comprising SEQ ID NO:103 and a light variable chain comprising SEQ ID NO:97;

(viii) an anti-GAG motif antibody or antigen-binding fragment thereof comprising a heavy variable chain comprising SEQ ID NO:104 and a light variable chain comprising SEQ ID NO:97;

(ix) an anti-GAG motif antibody or antigen-binding fragment thereof comprising a heavy variable chain comprising SEQ ID NO:105 and a light variable chain comprising SEQ ID NO:97;

(x) an anti-GAG motif antibody or antigen-binding fragment thereof comprising a heavy variable chain comprising SEQ ID NO:106 and a light variable chain comprising SEQ ID NO:97; and (xi) an anti-GAG motif antibody or antigen-binding fragment thereof comprising a heavy variable chain comprising SEQ ID NO:107 and a light variable chain comprising SEQ ID NO:97.

9. The method of claim 7, wherein the three or more anti-GAG motif antibodies or antigen-binding fragments thereof are single chain fragments variable (scFv).

10. The method of claim 8, wherein the three or more anti-GAG motif antibodies or antigen-binding fragments thereof comprise a sequence selected from the group consisting of SEQ ID NOs:1, 4, 7, 17, 20, 22, 26, 27, 29, 30, or 33.

* * * * *

```
                        SEQUENCE LISTING

<160> NUMBER OF SEQ ID NOS: 125

<210> SEQ ID NO 1
<211> LENGTH: 249
<212> TYPE: PRT
<213> ORGANISM: Artificial Sequence
<220> FEATURE:
<223> OTHER INFORMATION: synthetic peptide

<400> SEQUENCE: 1

Ala Met Ala Glu Val Gln Leu Leu Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Ala Ile Ser Gly Ser Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Ser Leu Arg Met Asn Gly Trp Arg Ala His Gln
            100                 105                 110
```

-continued

```
Trp Gly Gln Gly Thr Leu Val Thr Val Ser Arg Gly Gly Gly Ser
        115                 120                 125

Gly Gly Gly Gly Ser Gly Gly Gly Ser Ser Glu Leu Thr Gln Asp
    130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
                180                 185                 190

Gly Ile Pro Asp Arg Phe Ser Gly Ser Ser Ser Gly Asn Thr Ala Ser
                195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Asn His Val Val Phe Gly Gly Gly Thr
225                 230                 235                 240

Lys Leu Thr Val Leu Gly Ala Ala Ala
                245
```

```
<210> SEQ ID NO 2
<211> LENGTH: 247
<212> TYPE: PRT
<213> ORGANISM: Artificial Sequence
<220> FEATURE:
<223> OTHER INFORMATION: synthetic peptide

<400> SEQUENCE: 2
```

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Gly Lys Met Lys Leu Asn Arg Trp Gly
                100                 105                 110

Gln Gly Thr Leu Val Thr Val Ser Arg Gly Gly Gly Ser Gly Gly
            115                 120                 125

Gly Gly Ser Gly Gly Gly Gly Ser Ser Glu Leu Thr Gln Asp Pro Ala
    130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
                180                 185                 190

Pro Asp Arg Phe Ser Gly Ser Ser Ser Gly Asn Thr Ala Ser Leu Thr
                195                 200                 205

Ile Thr Gly Ala Gln Ala Glu Asp Glu Ala Asp Tyr Tyr Cys Asn Ser
    210                 215                 220
```

```
Arg Asp Ser Ser Gly Asn His Val Val Phe Gly Gly Gly Thr Lys Leu
225             230             235             240

Thr Val Leu Gly Ala Ala Ala
            245

<210> SEQ ID NO 3
<211> LENGTH: 243
<212> TYPE: PRT
<213> ORGANISM: Artificial Sequence
<220> FEATURE:
<223> OTHER INFORMATION: synthetic peptide

<400> SEQUENCE: 3

Ala Met Ala Glu Val Gln Leu Val Glu Ser Gly Gly Gly Leu Ile Gln
1               5               10              15

Pro Gly Gly Ser Leu Arg Leu Ser Cys Ala Ala Ser Gly Phe Thr Val
            20              25              30

Ser Ser Asn Tyr Met Ser Trp Val Arg Gln Ala Pro Gly Lys Gly Leu
        35              40              45

Glu Trp Val Ser Val Ile Tyr Ser Gly Gly Ser Thr Tyr Tyr Ala Asp
    50              55              60

Ser Val Lys Gly Arg Phe Thr Ile Ser Arg Asp Asn Ser Lys Asn Thr
65              70              75              80

Leu Tyr Leu Gln Met Asn Ser Leu Arg Ala Glu Asp Thr Ala Val Tyr
                85              90              95

Tyr Cys Ala Arg Gly Tyr Arg Pro Arg Phe Trp Gly Gln Gly Thr Leu
            100             105             110

Val Thr Val Ser Arg Gly Gly Gly Ser Gly Gly Gly Gly Ser Gly
            115             120             125

Gly Gly Gly Ser Ser Glu Leu Thr Gln Asp Pro Ala Val Ser Val Ala
        130             135             140

Leu Gly Gln Thr Val Arg Ile Thr Cys Gln Gly Asp Ser Leu Arg Ser
145             150             155             160

Tyr Tyr Ala Ser Trp Tyr Gln Gln Lys Pro Gly Gln Ala Pro Val Leu
                165             170             175

Val Ile Tyr Gly Lys Asn Asn Arg Pro Ser Gly Ile Pro Asp Arg Phe
            180             185             190

Ser Gly Ser Ser Ser Gly Asn Thr Ala Ser Leu Thr Ile Thr Gly Ala
            195             200             205

Gln Ala Glu Asp Glu Ala Asp Tyr Tyr Cys Asn Ser Arg Asp Ser Ser
        210             215             220

Gly Asn His Val Val Phe Gly Gly Gly Thr Lys Leu Thr Val Leu Gly
225             230             235             240

Ala Ala Ala

<210> SEQ ID NO 4
<211> LENGTH: 250
<212> TYPE: PRT
<213> ORGANISM: Artificial Sequence
<220> FEATURE:
<223> OTHER INFORMATION: synthetic peptide

<400> SEQUENCE: 4

Ala Met Ala Glu Val Gln Leu Leu Glu Ser Gly Gly Gly Leu Val Gln
1               5               10              15

Pro Gly Gly Ser Leu Arg Leu Ser Cys Ala Ala Ser Gly Phe Thr Phe
            20              25              30
```

-continued

```
Ser Ser Tyr Ala Met Ser Trp Val Arg Gln Ala Pro Gly Lys Gly Leu
        35              40              45

Glu Trp Val Ser Ala Ile Ser Gly Ser Gly Gly Ser Thr Tyr Tyr Ala
    50              55              60

Asp Ser Val Lys Gly Arg Phe Thr Ile Ser Arg Asp Asn Ser Lys Asn
65              70              75              80

Thr Leu Tyr Leu Gln Met Asn Ser Leu Arg Ala Glu Asp Thr Ala Val
            85              90              95

Tyr Tyr Cys Ala Arg Ser Ile Ser Met Asn Gly Val Gly Val Arg Ile
        100             105             110

Gln Trp Gly Gln Gly Thr Leu Val Thr Val Ser Arg Gly Gly Gly Gly
        115             120             125

Ser Gly Gly Gly Gly Ser Gly Gly Gly Ser Ser Glu Leu Thr Gln
    130             135             140

Asp Pro Ala Val Ser Val Ala Leu Gly Gln Thr Val Arg Ile Thr Cys
145             150             155             160

Gln Gly Asp Ser Leu Arg Ser Tyr Tyr Ala Ser Trp Tyr Gln Gln Lys
            165             170             175

Pro Gly Gln Ala Pro Val Leu Val Ile Tyr Gly Lys Asn Asn Arg Pro
        180             185             190

Ser Gly Ile Pro Asp Arg Phe Ser Gly Ser Ser Ser Gly Asn Thr Ala
        195             200             205

Ser Leu Thr Ile Thr Gly Ala Gln Ala Glu Asp Glu Ala Asp Tyr Tyr
    210             215             220

Cys Asn Ser Arg Asp Ser Ser Gly Asn His Val Val Phe Gly Gly Gly
225             230             235             240

Thr Lys Leu Thr Val Leu Gly Ala Ala Ala
            245             250
```

```
<210> SEQ ID NO 5
<211> LENGTH: 247
<212> TYPE: PRT
<213> ORGANISM: Artificial Sequence
<220> FEATURE:
<223> OTHER INFORMATION: synthetic peptide

<400> SEQUENCE: 5
```

```
Ala Met Ala Glu Val Gln Leu Val Glu Ser Gly Gly Gly Leu Val Lys
1               5               10              15

Pro Gly Gly Ser Leu Arg Leu Ser Cys Ala Ala Ser Gly Phe Thr Phe
            20              25              30

Ser Asn Ala Trp Met Ser Trp Val Arg Gln Ala Pro Gly Lys Gly Leu
        35              40              45

Glu Trp Val Gly Arg Ile Lys Ser Lys Thr Asp Gly Gly Thr Thr Asp
    50              55              60

Tyr Ala Ala Pro Val Lys Gly Arg Phe Thr Ile Ser Arg Asp Asp Ser
65              70              75              80

Lys Asn Thr Leu Tyr Leu Gln Met Asn Ser Leu Lys Thr Glu Asp Thr
            85              90              95

Ala Val Tyr Tyr Cys Ala Arg Gly Arg Thr Val Gly Arg Asn Trp Gly
        100             105             110

Gln Gly Thr Leu Val Thr Val Ser Arg Gly Gly Gly Ser Gly Gly
        115             120             125

Gly Gly Ser Gly Gly Gly Gly Ser Ser Glu Leu Thr Gln Asp Pro Ala
    130             135             140
```

-continued

```
Val Ser Val Ala Leu Gly Gln Thr Val Arg Ile Thr Cys Gln Gly Asp
145             150                 155                 160

Ser Leu Arg Ser Tyr Tyr Ala Ser Trp Tyr Gln Gln Lys Pro Gly Gln
                165             170             175

Ala Pro Val Leu Val Ile Tyr Gly Lys Asn Asn Arg Pro Ser Gly Ile
            180             185             190

Pro Asp Arg Phe Ser Gly Ser Ser Ser Gly Asn Thr Ala Ser Leu Thr
        195             200             205

Ile Thr Gly Ala Gln Ala Glu Asp Glu Ala Asp Tyr Tyr Cys Asn Ser
        210             215             220

Arg Asp Ser Ser Gly Asn His Val Val Phe Gly Gly Gly Thr Lys Leu
225             230             235             240

Thr Val Leu Gly Ala Ala Ala
                245

<210> SEQ ID NO 6
<211> LENGTH: 252
<212> TYPE: PRT
<213> ORGANISM: Artificial Sequence
<220> FEATURE:
<223> OTHER INFORMATION: synthetic peptide

<400> SEQUENCE: 6

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
                20              25              30

Ser Asn Ala Trp Met Ser Trp Val Arg Gln Ala Pro Gly Lys Gly Leu
            35              40              45

Glu Trp Val Gly Arg Ile Lys Ser Lys Thr Asp Gly Gly Thr Thr Asp
    50              55              60

Tyr Ala Ala Pro Val Lys Gly Arg Phe Thr Ile Ser Arg Asp Asp Ser
65              70              75              80

Lys Asn Thr Leu Tyr Leu Gln Met Asn Ser Leu Lys Thr Glu Asp Thr
            85              90              95

Ala Val Tyr Tyr Cys Ala Arg Asp Arg Arg Asn Thr Gln Lys Thr Arg
            100             105             110

Tyr Arg Thr Trp Gly Gln Gly Thr Leu Val Thr Val Ser Arg Gly Gly
        115             120             125

Gly Gly Ser Gly Gly Gly Gly Ser Gly Gly Gly Gly Ser Ser Glu Leu
        130             135             140

Thr Gln Asp Pro Ala Val Ser Val Ala Leu Gly Gln Thr Val Arg Ile
145             150             155             160

Thr Cys Gln Gly Asp Ser Leu Arg Ser Tyr Tyr Ala Ser Trp Tyr Gln
                165             170             175

Gln Lys Pro Gly Gln Ala Pro Val Leu Val Ile Tyr Gly Lys Asn Asn
                180             185             190

Arg Pro Ser Gly Ile Pro Asp Arg Phe Ser Gly Ser Ser Ser Gly Asn
            195             200             205

Thr Ala Ser Leu Thr Ile Thr Gly Ala Gln Ala Glu Asp Glu Ala Asp
        210             215             220

Tyr Tyr Cys Asn Ser Arg Asp Ser Ser Gly Asn His Val Val Phe Gly
225             230             235             240

Gly Gly Thr Lys Leu Thr Val Leu Gly Ala Ala Ala
            245             250
```

-continued

```
<210> SEQ ID NO 7
<211> LENGTH: 252
<212> TYPE: PRT
<213> ORGANISM: Artificial Sequence
<220> FEATURE:
<223> OTHER INFORMATION: synthetic peptide

<400> SEQUENCE: 7

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Ser Gly Arg Gln Ala Arg Gln Gly Arg
            100                 105                 110

Phe Pro Lys Trp Gly Gln Gly Thr Leu Val Thr Val Ser Arg Gly Gly
            115                 120                 125

Gly Gly Ser Gly Gly Gly Gly Ser Gly Gly Gly Gly Ser Ser Glu Leu
        130                 135                 140

Thr Gln Asp Pro Ala Val Ser Val Ala Leu Gly Gln Thr Val Arg Ile
145                 150                 155                 160

Thr Cys Gln Gly Asp Ser Leu Arg Ser Tyr Tyr Ala Ser Trp Tyr Gln
                165                 170                 175

Gln Lys Pro Gly Gln Ala Pro Val Leu Val Ile Tyr Gly Lys Asn Asn
            180                 185                 190

Arg Pro Ser Gly Ile Pro Asp Arg Phe Ser Gly Ser Ser Ser Gly Asn
            195                 200                 205

Thr Ala Ser Leu Thr Ile Thr Gly Ala Gln Ala Glu Asp Glu Ala Asp
        210                 215                 220

Tyr Tyr Cys Asn Ser Arg Asp Ser Ser Gly Asn His Val Val Phe Gly
225                 230                 235                 240

Gly Gly Thr Lys Leu Thr Val Leu Gly Ala Ala Ala
                245                 250

<210> SEQ ID NO 8
<211> LENGTH: 248
<212> TYPE: PRT
<213> ORGANISM: Artificial Sequence
<220> FEATURE:
<223> OTHER INFORMATION: synthetic peptide

<400> SEQUENCE: 8

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60
```

```
Tyr Ala Ala Pro Val Lys Gly Arg Phe Thr Ile Ser Arg Asp Asp Ser
65              70              75              80

Lys Asn Thr Leu Tyr Leu Gln Met Asn Ser Leu Lys Thr Glu Asp Thr
                85              90              95

Ala Val Tyr Tyr Cys Ala Arg Gly Gly Thr Thr Arg Ile Arg Lys Trp
            100             105             110

Gly Gln Gly Thr Leu Val Thr Val Ser Arg Gly Gly Gly Gly Ser Gly
        115             120             125

Gly Gly Gly Ser Gly Gly Gly Ser Ser Glu Leu Thr Gln Asp Pro
    130             135             140

Ala Val Ser Val Ala Leu Gly Gln Thr Val Arg Ile Thr Cys Gln Gly
145             150             155             160

Asp Ser Leu Arg Ser Tyr Tyr Ala Ser Trp Tyr Gln Gln Lys Pro Gly
            165             170             175

Gln Ala Pro Val Leu Val Ile Tyr Gly Lys Asn Asn Arg Pro Ser Gly
        180             185             190

Ile Pro Asp Arg Phe Ser Gly Ser Ser Ser Gly Asn Thr Ala Ser Leu
        195             200             205

Thr Ile Thr Gly Ala Gln Ala Glu Asp Glu Ala Asp Tyr Tyr Cys Asn
    210             215             220

Ser Arg Asp Ser Ser Gly Asn His Val Val Phe Gly Gly Gly Thr Lys
225             230             235             240

Leu Thr Val Leu Gly Ala Ala Ala
            245
```

```
<210> SEQ ID NO 9
<211> LENGTH: 246
<212> TYPE: PRT
<213> ORGANISM: Artificial Sequence
<220> FEATURE:
<223> OTHER INFORMATION: synthetic peptide

<400> SEQUENCE: 9
```

```
Ala Met Ala Gln Val Gln Leu Val Gln Ser Gly Ala Glu Val Lys Lys
1               5               10              15

Pro Gly Ala Ser Val Lys Val Ser Cys Lys Ala Ser Gly Tyr Thr Phe
            20              25              30

Thr Gly Tyr Tyr Met His Trp Val Arg Gln Ala Pro Gly Gln Gly Leu
        35              40              45

Glu Trp Met Gly Trp Ile Asn Pro Asn Ser Gly Gly Thr Asn Tyr Ala
    50              55              60

Gln Lys Phe Gln Gly Trp Val Thr Met Thr Arg Asp Thr Ser Ile Ser
65              70              75              80

Thr Ala Tyr Met Glu Leu Ser Arg Leu Arg Ser Asp Asp Thr Ala Val
            85              90              95

Tyr Tyr Cys Ala Arg Gly Thr Lys Leu Lys Met Thr Lys Trp Gly Gln
            100             105             110

Gly Thr Leu Val Thr Val Ser Arg Gly Gly Gly Gly Ser Gly Gly Gly
        115             120             125

Gly Ser Gly Gly Gly Gly Ser Ser Glu Leu Thr Gln Asp Pro Ala Val
        130             135             140

Ser Val Ala Leu Gly Gln Thr Val Arg Ile Thr Cys Gln Gly Asp Ser
145             150             155             160

Leu Arg Ser Tyr Tyr Ala Ser Trp Tyr Gln Gln Lys Pro Gly Gln Ala
            165             170             175
```

-continued

```
Pro Val Leu Val Ile Tyr Gly Lys Asn Asn Arg Pro Ser Gly Ile Pro
            180                 185             190

Asp Arg Phe Ser Gly Ser Ser Ser Gly Asn Thr Ala Ser Leu Thr Ile
            195                 200             205

Thr Gly Ala Gln Ala Glu Asp Glu Ala Asp Tyr Tyr Cys Asn Ser Arg
            210                 215             220

Asp Ser Ser Gly Asn His Val Val Phe Gly Gly Gly Thr Lys Leu Thr
225                 230             235             240

Val Leu Gly Ala Ala Ala
            245
```

```
<210> SEQ ID NO 10
<211> LENGTH: 247
<212> TYPE: PRT
<213> ORGANISM: Artificial Sequence
<220> FEATURE:
<223> OTHER INFORMATION: synthetic peptide

<400> SEQUENCE: 10
```

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
            35                  40                  45

Glu Trp Val Gly Arg Ile Lys Ser Lys Thr Asp Gly Gly Thr Thr Asp
            50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Glu Arg Asn Thr Ile Arg Arg Trp Gly
            100                 105                 110

Gln Gly Thr Leu Val Thr Val Ser Arg Gly Gly Gly Ser Gly Gly
            115                 120                 125

Gly Gly Ser Gly Gly Gly Gly Ser Ser Glu Leu Thr Gln Asp Pro Ala
            130                 135                 140

Val Ser Val Ala Leu Gly Gln Thr Val Arg Ile Thr Cys Gln Gly Asp
145                 150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Ser Gly Asn Thr Ala Ser Leu Thr
            195                 200                 205

Ile Thr Gly Ala Gln Ala Glu Asp Glu Ala Asp Tyr Tyr Cys Asn Ser
            210                 215                 220

Arg Asp Ser Ser Gly Asn His Val Val Phe Gly Gly Gly Thr Lys Leu
225                 230                 235                 240

Thr Val Leu Gly Ala Ala Ala
                245
```

```
<210> SEQ ID NO 11
<211> LENGTH: 245
<212> TYPE: PRT
<213> ORGANISM: Artificial Sequence
```

<220> FEATURE:
<223> OTHER INFORMATION: synthetic peptide

<400> SEQUENCE: 11

Ala Met Ala Glu Val Gln Leu Val Glu Ser Gly Gly Gly Leu Val Gln
1               5                   10                  15

Pro Gly Gly Ser Leu Arg Leu Ser Cys Ala Gly Ser Gly Phe Thr Phe
            20                  25                  30

Ser Ser Tyr Ala Met His Trp Val Arg Gln Ala Pro Gly Lys Gly Leu
        35                  40                  45

Glu Trp Val Ser Ala Ile Gly Thr Gly Gly Gly Thr Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Arg Leu His Leu Pro Arg Lys Trp Gly Gln Gly
            100                 105                 110

Thr Leu Val Thr Val Ser Arg Gly Gly Gly Gly Ser Gly Gly Gly Gly
            115                 120                 125

Ser Gly Gly Gly Gly Ser Ser Glu Leu Thr Gln Asp Pro Ala Val Ser
        130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
                180                 185                 190

Arg Phe Ser Gly Ser Ser Ser Gly Asn Thr Ala Ser Leu Thr Ile Thr
            195                 200                 205

Gly Ala Gln Ala Glu Asp Glu Ala Asp Tyr Tyr Cys Asn Ser Arg Asp
    210                 215                 220

Ser Ser Gly Asn His Val Val Phe Gly Gly Gly Thr Lys Leu Thr Val
225                 230                 235                 240

Leu Gly Ala Ala Ala
            245

<210> SEQ ID NO 12
<211> LENGTH: 248
<212> TYPE: PRT
<213> ORGANISM: Artificial Sequence
<220> FEATURE:
<223> OTHER INFORMATION: synthetic peptide

<400> SEQUENCE: 12

Ala Met Ala Gln Val Gln Leu Val Gln Ser Gly Ala Glu Val Lys Lys
1               5                   10                  15

Pro Gly Ala Ser Val Lys Val Ser Cys Lys Ala Ser Gly Tyr Thr Phe
            20                  25                  30

Thr Gly Tyr Tyr Met His Trp Val Arg Gln Ala Pro Gly Gln Gly Leu
        35                  40                  45

Glu Trp Met Gly Trp Ile Asn Pro Asn Ser Gly Gly Thr Asn Tyr Ala
    50                  55                  60

Gln Lys Phe Gln Gly Trp Val Thr Met Thr Arg Asp Thr Ser Ile Ser
65                  70                  75                  80

Thr Ala Tyr Met Glu Leu Ser Arg Leu Arg Ser Asp Asp Thr Ala Val

-continued

```
                    85              90              95

Tyr Tyr Cys Ala Arg Ser Ser Ser Arg His His Arg Leu His Arg Trp
                100             105             110

Gly Gln Gly Thr Leu Val Thr Val Ser Arg Gly Gly Gly Ser Gly
            115             120             125

Gly Gly Gly Ser Gly Gly Gly Gly Ser Ser Glu Leu Thr Gln Asp Pro
        130             135             140

Ala Val Ser Val Ala Leu Gly Gln Thr Val Arg Ile Thr Cys Gln Gly
145             150             155             160

Asp Ser Leu Arg Ser Tyr Tyr Ala Ser Trp Tyr Gln Gln Lys Pro Gly
                165             170             175

Gln Ala Pro Val Leu Val Ile Tyr Gly Lys Asn Asn Arg Pro Ser Gly
            180             185             190

Ile Pro Asp Arg Phe Ser Gly Ser Ser Ser Gly Asn Thr Ala Ser Leu
            195             200             205

Thr Ile Thr Gly Ala Gln Ala Glu Asp Glu Ala Asp Tyr Tyr Cys Asn
        210             215             220

Ser Arg Asp Ser Ser Gly Asn His Val Val Phe Gly Gly Gly Thr Lys
225             230             235             240

Leu Thr Val Leu Gly Ala Ala Ala
                245

<210> SEQ ID NO 13
<211> LENGTH: 250
<212> TYPE: PRT
<213> ORGANISM: Artificial Sequence
<220> FEATURE:
<223> OTHER INFORMATION: synthetic peptide

<400> SEQUENCE: 13

Ala Met Ala Gln Val Gln Leu Val Gln Ser Gly Ala Glu Val Lys Lys
1               5               10              15

Pro Gly Ala Ser Val Lys Val Ser Cys Lys Ala Ser Gly Tyr Thr Phe
            20              25              30

Thr Ser Tyr Ala Met His Trp Val Arg Gln Ala Pro Gly Gln Arg Leu
        35              40              45

Glu Trp Met Gly Trp Ile Asn Ala Gly Asn Gly Asn Thr Lys Tyr Ser
    50              55              60

Gln Lys Phe Gln Gly Arg Val Thr Ile Thr Arg Asp Thr Ser Ala Ser
65              70              75              80

Thr Ala Tyr Met Glu Leu Ser Ser Leu Arg Ser Glu Asp Thr Ala Val
                85              90              95

Tyr Tyr Cys Ala Arg Gln Arg Trp Lys Pro Ala Val Thr Pro Lys Leu
                100             105             110

Val Trp Gly Gln Gly Thr Leu Val Thr Val Ser Arg Gly Gly Gly Gly
            115             120             125

Ser Gly Gly Gly Gly Ser Gly Gly Gly Gly Ser Ser Glu Leu Thr Gln
        130             135             140

Asp Pro Ala Val Ser Val Ala Leu Gly Gln Thr Val Arg Ile Thr Cys
145             150             155             160

Gln Gly Asp Ser Leu Arg Ser Tyr Tyr Ala Ser Trp Tyr Gln Gln Lys
                165             170             175

Pro Gly Gln Ala Pro Val Leu Val Ile Tyr Gly Lys Asn Asn Arg Pro
            180             185             190

Ser Gly Ile Pro Asp Arg Phe Ser Gly Ser Ser Ser Gly Asn Thr Ala
```

```
            195                 200                 205

Ser Leu Thr Ile Thr Gly Ala Gln Ala Glu Asp Glu Ala Asp Tyr Tyr
    210                 215                 220

Cys Asn Ser Arg Asp Ser Ser Gly Asn His Val Val Phe Gly Gly Gly
225                 230                 235                 240

Thr Lys Leu Thr Val Leu Gly Ala Ala Ala
                245                 250
```

<210> SEQ ID NO 14
<211> LENGTH: 249
<212> TYPE: PRT
<213> ORGANISM: Artificial Sequence
<220> FEATURE:
<223> OTHER INFORMATION: synthetic peptide

<400> SEQUENCE: 14

```
Ala Met Ala Glu Val Gln Leu Val Glu Ser Gly Gly Gly Leu Val Gln
1               5                   10                  15

Pro Gly Gly Ser Leu Arg Leu Ser Cys Ala Gly Ser Gly Phe Thr Phe
                20                  25                  30

Ser Ser Tyr Ala Met His Trp Val Arg Gln Ala Pro Gly Lys Gly Leu
            35                  40                  45

Glu Trp Val Ser Ala Ile Gly Thr Gly Gly Gly Thr Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Ala Arg Met Thr Gly His Val Arg Asn Val Met Ile
            100                 105                 110

Trp Gly Gln Gly Thr Leu Val Thr Val Ser Arg Gly Gly Gly Gly Ser
        115                 120                 125

Gly Gly Gly Gly Ser Gly Gly Gly Gly Ser Ser Glu Leu Thr Gln Asp
        130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
                180                 185                 190

Gly Ile Pro Asp Arg Phe Ser Gly Ser Ser Ser Gly Asn Thr Ala Ser
        195                 200                 205

Leu Thr Ile Thr Gly Ala Gln Ala Glu Asp Glu Ala Asp Tyr Tyr Cys
    210                 215                 220

Asn Ser Arg Asp Ser Ser Gly Asn His Val Val Phe Gly Gly Gly Thr
225                 230                 235                 240

Lys Leu Thr Val Leu Gly Ala Ala Ala
                245
```

<210> SEQ ID NO 15
<211> LENGTH: 248
<212> TYPE: PRT
<213> ORGANISM: Artificial Sequence
<220> FEATURE:
<223> OTHER INFORMATION: synthetic peptide

<400> SEQUENCE: 15

-continued

```
Ala Met Ala Glu Val Gln Leu Val Glu Ser Gly Gly Gly Leu Val Gln
1               5                   10                  15

Pro Gly Gly Ser Leu Arg Leu Ser Cys Ala Gly Ser Gly Phe Thr Phe
            20                  25                  30

Ser Ser Tyr Ala Met His Trp Val Arg Gln Ala Pro Gly Lys Gly Leu
        35                  40                  45

Glu Trp Val Ser Ala Ile Gly Thr Gly Gly Gly Thr Tyr Tyr Ala Asp
    50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Pro Val Ser His Arg Lys Trp Arg Val Thr Val Trp
            100                 105                 110

Gly Gln Gly Thr Leu Val Thr Val Ser Arg Gly Gly Gly Gly Ser Gly
        115                 120                 125

Gly Gly Gly Ser Gly Gly Gly Gly Ser Ser Glu Leu Thr Gln Asp Pro
        130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
            165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Asn Thr Ala Ser Leu
            195                 200                 205

Thr Ile Thr Gly Ala Gln Ala Glu Asp Glu Ala Asp Tyr Tyr Cys Asn
        210                 215                 220

Ser Arg Asp Ser Ser Gly Asn His Val Val Phe Gly Gly Gly Thr Lys
225                 230                 235                 240

Leu Thr Val Leu Gly Ala Ala Ala
                245
```

```
<210> SEQ ID NO 16
<211> LENGTH: 248
<212> TYPE: PRT
<213> ORGANISM: Artificial Sequence
<220> FEATURE:
<223> OTHER INFORMATION: synthetic peptide

<400> SEQUENCE: 16
```

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Gly Arg Arg His Lys Leu Ile Arg Trp
            100                 105                 110
```

```
Gly Gln Gly Thr Leu Val Thr Val Ser Arg Gly Gly Gly Ser Gly
        115                 120                 125

Gly Gly Gly Ser Gly Gly Gly Ser Ser Glu Leu Thr Gln Asp Pro
        130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
            180                 185                 190

Ile Pro Asp Arg Phe Ser Gly Ser Ser Ser Gly Asn Thr Ala Ser Leu
            195                 200                 205

Thr Ile Thr Gly Ala Gln Ala Glu Asp Glu Ala Asp Tyr Tyr Cys Asn
    210                 215                 220

Ser Arg Asp Ser Ser Gly Asn His Val Val Phe Gly Gly Gly Thr Lys
225                 230                 235                 240

Leu Thr Val Leu Gly Ala Ala Ala
                245
```

```
<210> SEQ ID NO 17
<211> LENGTH: 249
<212> TYPE: PRT
<213> ORGANISM: Artificial Sequence
<220> FEATURE:
<223> OTHER INFORMATION: synthetic peptide

<400> SEQUENCE: 17
```

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Leu Arg Gly Thr Lys Met Phe Arg His
            100                 105                 110

Trp Gly Gln Gly Thr Leu Val Thr Val Ser Arg Gly Gly Gly Gly Ser
        115                 120                 125

Gly Gly Gly Gly Ser Gly Gly Gly Gly Ser Ser Glu Leu Thr Gln Asp
        130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
            180                 185                 190

Gly Ile Pro Asp Arg Phe Ser Gly Ser Ser Ser Gly Asn Thr Ala Ser
            195                 200                 205

Leu Thr Ile Thr Gly Ala Gln Ala Glu Asp Glu Ala Asp Tyr Tyr Cys
    210                 215                 220
```

-continued

Asn Ser Arg Asp Ser Ser Gly Asn His Val Val Phe Gly Gly Gly Thr
225             230                 235                 240

Lys Leu Thr Val Leu Gly Ala Ala Ala
            245

<210> SEQ ID NO 18
<211> LENGTH: 249
<212> TYPE: PRT
<213> ORGANISM: Artificial Sequence
<220> FEATURE:
<223> OTHER INFORMATION: synthetic peptide

<400> SEQUENCE: 18

Ala Met Ala Gln Val Gln Leu Val Gln Ser Gly Ala Glu Val Lys Lys
1               5                   10                  15

Pro Gly Ala Thr Val Lys Ile Ser Cys Lys Val Ser Gly Tyr Thr Phe
            20                  25                  30

Thr Asp Tyr Tyr Met His Trp Val Gln Gln Ala Pro Gly Lys Gly Leu
        35                  40                  45

Glu Trp Met Gly Leu Val Asp Pro Glu Asp Gly Glu Thr Ile Tyr Ala
    50                  55                  60

Glu Lys Phe Gln Gly Arg Val Thr Ile Thr Ala Asp Thr Ser Thr Asp
65                  70                  75                  80

Thr Ala Tyr Met Glu Leu Ser Ser Leu Arg Ser Glu Asp Thr Ala Val
            85                  90                  95

Tyr Tyr Cys Ala Arg Ser Arg Lys Thr Pro Lys Pro Phe Met Arg Lys
            100                 105                 110

Trp Gly Gln Gly Thr Leu Val Thr Val Ser Arg Gly Gly Gly Gly Ser
            115                 120                 125

Gly Gly Gly Gly Ser Gly Gly Gly Ser Ser Glu Leu Thr Gln Asp
        130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
            165                 170                 175

Gly Gln Ala Pro Val Leu Val Ile Tyr Gly Lys Asn Asn Arg Pro Ser
            180                 185                 190

Gly Ile Pro Asp Arg Phe Ser Gly Ser Ser Ser Gly Asn Thr Ala Ser
            195                 200                 205

Leu Thr Ile Thr Gly Ala Gln Ala Glu Asp Glu Ala Asp Tyr Tyr Cys
        210                 215                 220

Asn Ser Arg Asp Ser Ser Gly Asn His Val Val Phe Gly Gly Gly Thr
225             230                 235                 240

Lys Leu Thr Val Leu Gly Ala Ala Ala
            245

<210> SEQ ID NO 19
<211> LENGTH: 243
<212> TYPE: PRT
<213> ORGANISM: Artificial Sequence
<220> FEATURE:
<223> OTHER INFORMATION: synthetic peptide

<400> SEQUENCE: 19

Ala Met Ala Glu Val Gln Leu Val Glu Ser Gly Gly Gly Leu Ile Gln
1               5                   10                  15

Pro Gly Gly Ser Leu Arg Leu Ser Cys Ala Ala Ser Gly Phe Thr Val
            20                  25                  30

-continued

```
Ser Ser Asn Tyr Met Ser Trp Val Arg Gln Ala Pro Gly Lys Gly Leu
        35              40              45

Glu Trp Val Ser Val Ile Tyr Ser Gly Gly Ser Thr Tyr Tyr Ala Asp
    50              55              60

Ser Val Lys Gly Arg Phe Thr Ile Ser Arg Asp Asn Ser Lys Asn Thr
65              70              75              80

Leu Tyr Leu Gln Met Asn Ser Leu Arg Ala Glu Asp Thr Ala Val Tyr
                85              90              95

Tyr Cys Ala Arg Gly Ala Arg Leu Lys Arg Trp Gly Gln Gly Thr Leu
            100             105             110

Val Thr Val Ser Arg Gly Gly Gly Ser Gly Gly Gly Ser Gly
            115             120             125

Gly Gly Gly Ser Ser Glu Leu Thr Gln Asp Pro Ala Val Ser Val Ala
    130             135             140

Leu Gly Gln Thr Val Arg Ile Thr Cys Gln Gly Asp Ser Leu Arg Ser
145             150             155             160

Tyr Tyr Ala Ser Trp Tyr Gln Gln Lys Pro Gly Gln Ala Pro Val Leu
                165             170             175

Val Ile Tyr Gly Lys Asn Asn Arg Pro Ser Gly Ile Pro Asp Arg Phe
            180             185             190

Ser Gly Ser Ser Ser Gly Asn Thr Ala Ser Leu Thr Ile Thr Gly Ala
            195             200             205

Gln Ala Glu Asp Glu Ala Asp Tyr Tyr Cys Asn Ser Arg Asp Ser Ser
    210             215             220

Gly Asn His Val Val Phe Gly Gly Gly Thr Lys Leu Thr Val Leu Gly
225             230             235             240

Ala Ala Ala
```

```
<210> SEQ ID NO 20
<211> LENGTH: 247
<212> TYPE: PRT
<213> ORGANISM: Artificial Sequence
<220> FEATURE:
<223> OTHER INFORMATION: synthetic peptide

<400> SEQUENCE: 20
```

```
Ala Met Ala Glu Val Gln Leu Val Glu Ser Gly Gly Gly Leu Val Lys
1               5               10              15

Pro Gly Gly Ser Leu Arg Leu Ser Cys Ala Ala Ser Gly Phe Thr Phe
            20              25              30

Ser Asn Ala Trp Met Ser Trp Val Arg Gln Ala Pro Gly Lys Gly Leu
        35              40              45

Glu Trp Val Gly Arg Ile Lys Ser Lys Thr Asp Gly Gly Thr Thr Asp
    50              55              60

Tyr Ala Ala Pro Val Lys Gly Arg Phe Thr Ile Ser Arg Asp Asp Ser
65              70              75              80

Lys Asn Thr Leu Tyr Leu Gln Met Asn Ser Leu Lys Thr Glu Asp Thr
                85              90              95

Ala Val Tyr Tyr Cys Ala Arg Gly Lys Val Lys Leu Pro Asn Trp Gly
            100             105             110

Gln Gly Thr Leu Val Thr Val Ser Arg Gly Gly Gly Ser Gly Gly
    115             120             125

Gly Gly Ser Gly Gly Gly Gly Ser Ser Glu Leu Thr Gln Asp Pro Ala
    130             135             140
```

```
Val Ser Val Ala Leu Gly Gln Thr Val Arg Ile Thr Cys Gln Gly Asp
145             150                 155                 160

Ser Leu Arg Ser Tyr Tyr Ala Ser Trp Tyr Gln Gln Lys Pro Gly Gln
                165                 170                 175

Ala Pro Val Leu Val Ile Tyr Gly Lys Asn Asn Arg Pro Ser Gly Ile
            180                 185                 190

Pro Asp Arg Phe Ser Gly Ser Ser Gly Asn Thr Ala Ser Leu Thr
            195                 200                 205

Ile Thr Gly Ala Gln Ala Glu Asp Glu Ala Asp Tyr Tyr Cys Asn Ser
        210                 215                 220

Arg Asp Ser Ser Gly Asn His Val Val Phe Gly Gly Gly Thr Lys Leu
225                 230                 235                 240

Thr Val Leu Gly Ala Ala Ala
                245

<210> SEQ ID NO 21
<211> LENGTH: 244
<212> TYPE: PRT
<213> ORGANISM: Artificial Sequence
<220> FEATURE:
<223> OTHER INFORMATION: synthetic peptide

<400> SEQUENCE: 21

Ala Met Ala Glu Val Gln Leu Val Glu Ser Gly Gly Gly Leu Val Gln
1               5                   10                  15

Pro Gly Gly Ser Leu Arg Leu Ser Cys Ala Gly Ser Gly Phe Thr Phe
                20                  25                  30

Ser Ser Tyr Ala Met His Trp Val Arg Gln Ala Pro Gly Lys Gly Leu
            35                  40                  45

Glu Trp Val Ser Ala Ile Gly Thr Gly Gly Gly Thr Tyr Tyr Ala Asp
        50                  55                  60

Ser Val Lys Gly Arg Phe Thr Ile Ser Arg Asp Asn Ala Lys Asn Ser
65                  70                  75                  80

Leu Tyr Leu Gln Met Asn Ser Leu Arg Ala Glu Asp Thr Ala Val Tyr
                85                  90                  95

Tyr Cys Ala Arg Gly Thr Lys Lys Leu Gly Lys Trp Gly Gln Gly Thr
            100                 105                 110

Leu Val Thr Val Ser Arg Gly Gly Gly Gly Ser Gly Gly Gly Gly Ser
            115                 120                 125

Gly Gly Gly Gly Ser Ser Glu Leu Thr Gln Asp Pro Ala Val Ser Val
        130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
            180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Gly Ala Ala Ala
```

<210> SEQ ID NO 22
<211> LENGTH: 246
<212> TYPE: PRT
<213> ORGANISM: Artificial Sequence
<220> FEATURE:
<223> OTHER INFORMATION: synthetic peptide

<400> SEQUENCE: 22

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Gly Met Arg Pro Arg Leu Trp Gly Gln
            100                 105                 110

Gly Thr Leu Val Thr Val Ser Arg Gly Gly Gly Ser Gly Gly Gly
            115                 120                 125

Gly Ser Gly Gly Gly Gly Ser Ser Glu Leu Thr Gln Asp Pro Ala Val
        130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
        210                 215                 220

Asp Ser Ser Gly Asn His Val Val Phe Gly Gly Gly Thr Lys Leu Thr
225                 230                 235                 240

Val Leu Gly Ala Ala Ala
                245

<210> SEQ ID NO 23
<211> LENGTH: 249
<212> TYPE: PRT
<213> ORGANISM: Artificial Sequence
<220> FEATURE:
<223> OTHER INFORMATION: synthetic peptide

<400> SEQUENCE: 23

Ala Met Ala Gln Val Gln Leu Val Gln Ser Gly Ala Glu Val Lys Lys
1               5                   10                  15

Pro Gly Ala Thr Val Lys Ile Ser Cys Lys Val Ser Gly Tyr Thr Phe
            20                  25                  30

Thr Asp Tyr Tyr Met His Trp Val Gln Gln Ala Pro Gly Lys Gly Leu
        35                  40                  45

Glu Trp Met Gly Leu Val Asp Pro Glu Asp Gly Glu Thr Ile Tyr Ala
    50                  55                  60

-continued

```
Glu Lys Phe Gln Gly Arg Val Thr Ile Thr Ala Asp Thr Ser Thr Asp
65                  70                  75                  80

Thr Ala Tyr Met Glu Leu Ser Ser Leu Arg Ser Glu Asp Thr Ala Val
                85                  90                  95

Tyr Tyr Cys Ala Arg Ser Arg Lys Thr Arg Lys Pro Phe Met Arg Lys
            100                 105                 110

Trp Gly Gln Gly Thr Leu Val Thr Val Ser Arg Gly Gly Gly Gly Ser
            115                 120                 125

Gly Gly Gly Gly Ser Gly Gly Gly Gly Ser Ser Glu Leu Thr Gln Asp
            130                 135                 140

Pro Ala Val Ser Val Ala Leu Gly Gln Thr Val Arg Ile Thr Cys Gln
145                 150                 155                 160

Gly Asp Ser Leu Arg Ser Tyr Tyr Ala Ser Trp Tyr Gln Gln Lys Pro
                165                 170                 175

Gly Gln Ala Pro Val Leu Val Ile Tyr Gly Lys Asn Asn Arg Pro Ser
                180                 185                 190

Gly Ile Pro Asp Arg Phe Ser Gly Ser Ser Ser Gly Asn Thr Ala Ser
                195                 200                 205

Leu Thr Ile Thr Gly Ala Gln Ala Glu Asp Glu Ala Asp Tyr Tyr Cys
            210                 215                 220

Asn Ser Arg Asp Ser Ser Gly Asn His Val Val Phe Gly Gly Gly Thr
225                 230                 235                 240

Lys Leu Thr Val Leu Gly Ala Ala Ala
                245
```

```
<210> SEQ ID NO 24
<211> LENGTH: 245
<212> TYPE: PRT
<213> ORGANISM: Artificial Sequence
<220> FEATURE:
<223> OTHER INFORMATION: synthetic peptide

<400> SEQUENCE: 24
```

```
Ala Met Ala Gln Val Gln Leu Val Gln Ser Gly Ala Glu Val Lys Lys
1               5                   10                  15

Pro Gly Ala Ser Val Lys Val Ser Cys Lys Ala Ser Gly Tyr Thr Phe
            20                  25                  30

Thr Gly Tyr Tyr Met His Trp Val Arg Gln Ala Pro Gly Gln Gly Leu
            35                  40                  45

Glu Trp Met Gly Trp Ile Asn Pro Asn Ser Gly Gly Thr Asn Tyr Ala
        50                  55                  60

Gln Lys Phe Gln Gly Trp Val Thr Met Thr Arg Asp Thr Ser Ile Ser
65                  70                  75                  80

Thr Ala Tyr Met Glu Leu Ser Arg Leu Arg Ser Asp Asp Thr Ala Val
                85                  90                  95

Tyr Tyr Cys Ala Arg Tyr Tyr His Tyr Lys Val Asn Trp Gly Gln Gly
            100                 105                 110

Thr Leu Val Thr Val Ser Arg Gly Gly Gly Gly Ser Gly Gly Gly Gly
            115                 120                 125

Ser Gly Gly Gly Gly Ser Ser Glu Leu Thr Gln Asp Pro Ala Val Ser
            130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175
```

```
Val Leu Val Ile Tyr Gly Lys Asn Asn Arg Pro Ser Gly Ile Pro Asp
                180                 185                 190

Arg Phe Ser Gly Ser Ser Ser Gly Asn Thr Ala Ser Leu Thr Ile Thr
            195                 200                 205

Gly Ala Gln Ala Glu Asp Glu Ala Asp Tyr Tyr Cys Asn Ser Arg Asp
        210                 215                 220

Ser Ser Gly Asn His Val Val Phe Gly Gly Gly Thr Lys Leu Thr Val
225                 230                 235                 240

Leu Gly Ala Ala Ala
                245

<210> SEQ ID NO 25
<211> LENGTH: 244
<212> TYPE: PRT
<213> ORGANISM: Artificial Sequence
<220> FEATURE:
<223> OTHER INFORMATION: synthetic peptide

<400> SEQUENCE: 25

Ala Met Ala Gln Val Gln Leu Gln Glu Ser Gly Pro Gly Leu Val Lys
1               5                   10                  15

Pro Ser Gln Thr Leu Ser Leu Thr Cys Thr Val Ser Gly Gly Ser Ile
            20                  25                  30

Ser Ser Gly Gly Tyr Tyr Trp Ser Trp Ile Arg Gln His Pro Gly Lys
        35                  40                  45

Gly Leu Glu Trp Ile Gly Tyr Ile Tyr Tyr Ser Gly Ser Thr Tyr Tyr
    50                  55                  60

Asn Pro Ser Leu Lys Ser Arg Val Thr Ile Ser Val Asp Thr Ser Lys
65                  70                  75                  80

Asn Gln Phe Ser Leu Lys Leu Ser Ser Val Thr Ala Ala Asp Thr Ala
            85                  90                  95

Val Tyr Tyr Cys Ala Arg Trp Val Thr Glu Pro Trp Gly Gln Gly Thr
            100                 105                 110

Leu Val Thr Val Ser Arg Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
            165                 170                 175

Leu Val Ile Tyr Gly Lys Asn Asn Arg Pro Ser Gly Ile Pro Asp Arg
                180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
        210                 215                 220

Ser Gly Asn His Val Val Phe Gly Gly Gly Thr Lys Leu Thr Val Leu
225                 230                 235                 240

Gly Ala Ala Ala

<210> SEQ ID NO 26
<211> LENGTH: 246
<212> TYPE: PRT
<213> ORGANISM: Artificial Sequence
<220> FEATURE:
<223> OTHER INFORMATION: synthetic peptide
```

-continued

<400> SEQUENCE: 26

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
            85                  90                  95

Ala Val Tyr Tyr Cys Ala Arg Gly Arg Arg Leu Lys Asp Trp Gly Gln
            100                 105                 110

Gly Thr Leu Val Thr Val Ser Arg Gly Gly Gly Ser Gly Gly Gly
            115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
            165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
    210                 215                 220

Asp Ser Ser Gly Asn His Val Val Phe Gly Gly Gly Thr Lys Leu Thr
225                 230                 235                 240

Val Leu Gly Ala Ala Ala
                245

<210> SEQ ID NO 27
<211> LENGTH: 244
<212> TYPE: PRT
<213> ORGANISM: Artificial Sequence
<220> FEATURE:
<223> OTHER INFORMATION: synthetic peptide

<400> SEQUENCE: 27

Ala Met Ala Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Glu Met Asn Trp Val Arg Gln Ala Pro Gly Lys Gly Leu
        35                  40                  45

Glu Trp Val Ser Tyr Ile Ser Ser Ser Gly Ser Thr Ile Tyr Tyr Ala
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
            85                  90                  95

-continued

```
Tyr Tyr Cys Ala Arg Gly Met Arg Pro Arg Leu Trp Gly Gln Gly Thr
            100                 105                 110

Leu Val Thr Val Ser Arg Gly Gly Gly Gly Ser Gly Gly Gly Gly Ser
            115                 120                 125

Gly Gly Gly Gly Ser Ser Glu Leu Thr Gln Asp Pro Ala Val Ser Val
            130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
                165                 170                 175

Leu Val Ile Tyr Gly Lys Asn Asn Arg Pro Ser Gly Ile Pro Asp Arg
                180                 185                 190

Phe Ser Gly Ser Ser Ser Gly Asn Thr Ala Ser Leu Thr Ile Thr Gly
            195                 200                 205

Ala Gln Ala Glu Asp Glu Ala Asp Tyr Tyr Cys Asn Ser Arg Asp Ser
            210                 215                 220

Ser Gly Asn His Val Val Phe Gly Gly Gly Thr Lys Leu Thr Val Leu
225                 230                 235                 240

Gly Ala Ala Ala

<210> SEQ ID NO 28
<211> LENGTH: 248
<212> TYPE: PRT
<213> ORGANISM: Artificial Sequence
<220> FEATURE:
<223> OTHER INFORMATION: synthetic peptide

<400> SEQUENCE: 28

Ala Met Ala Glu Val Gln Leu Val Glu Ser Gly Gly Gly Leu Ile Gln
1               5                   10                  15

Pro Gly Gly Ser Leu Arg Leu Ser Cys Ala Ala Ser Gly Phe Thr Val
                20                  25                  30

Ser Ser Asn Tyr Met Ser Trp Val Arg Gln Ala Pro Gly Lys Gly Leu
            35                  40                  45

Glu Trp Val Ser Val Ile Tyr Ser Gly Gly Ser Thr Tyr Tyr Ala Asp
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ser Leu Arg Met Asn Gly Cys Gly Ala His Gln Trp
            100                 105                 110

Gly Gln Gly Thr Leu Val Thr Val Ser Arg Gly Gly Gly Gly Ser Gly
            115                 120                 125

Gly Gly Gly Ser Gly Gly Gly Ser Ser Glu Leu Thr Gln Asp Pro
            130                 135                 140

Ala Val Ser Val Ala Leu Gly Gln Thr Val Arg Ile Thr Cys Gln Gly
145                 150                 155                 160

Asp Ser Leu Arg Ser Tyr Tyr Ala Ser Trp Tyr Gln Gln Lys Pro Gly
                165                 170                 175

Gln Ala Pro Val Leu Val Ile Tyr Gly Lys Asn Asn Arg Pro Ser Gly
                180                 185                 190

Ile Pro Asp Arg Phe Ser Gly Ser Ser Ser Gly Asn Thr Ala Ser Leu
            195                 200                 205

Thr Ile Thr Gly Ala Gln Ala Glu Asp Glu Ala Asp Tyr Tyr Cys Asn
```

-continued

```
         210                 215                 220

Ser Arg Asp Ser Ser Gly Asn His Val Val Phe Gly Gly Gly Thr Lys
225                 230                 235                 240

Leu Thr Val Leu Gly Ala Ala Ala
                245

<210> SEQ ID NO 29
<211> LENGTH: 251
<212> TYPE: PRT
<213> ORGANISM: Artificial Sequence
<220> FEATURE:
<223> OTHER INFORMATION: synthetic peptide

<400> SEQUENCE: 29

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
                20                  25                  30

Ser Asn Ala Trp Met Ser Trp Val Arg Gln Ala Pro Gly Lys Gly Leu
            35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg His Ala Pro Leu Arg Asn Thr Arg Thr
                100                 105                 110

Asn Thr Trp Gly Gln Gly Thr Leu Val Thr Val Ser Arg Gly Gly Gly
            115                 120                 125

Gly Ser Gly Gly Gly Gly Ser Gly Gly Gly Gly Ser Ser Glu Leu Thr
            130                 135                 140

Gln Asp Pro Ala Val Ser Val Ala Leu Gly Gln Thr Val Arg Ile Thr
145                 150                 155                 160

Cys Gln Gly Asp Ser Leu Arg Ser Tyr Tyr Ala Ser Trp Tyr Gln Gln
                165                 170                 175

Lys Pro Gly Gln Ala Pro Val Leu Val Ile Tyr Gly Lys Asn Asn Arg
                180                 185                 190

Pro Ser Gly Ile Pro Asp Arg Phe Ser Gly Ser Ser Ser Gly Asn Thr
            195                 200                 205

Ala Ser Leu Thr Ile Thr Gly Ala Gln Ala Glu Asp Glu Ala Asp Tyr
            210                 215                 220

Tyr Cys Asn Ser Arg Asp Ser Ser Gly Asn His Val Val Phe Gly Gly
225                 230                 235                 240

Gly Thr Lys Leu Thr Val Leu Gly Ala Ala Ala
                245                 250

<210> SEQ ID NO 30
<211> LENGTH: 246
<212> TYPE: PRT
<213> ORGANISM: Artificial Sequence
<220> FEATURE:
<223> OTHER INFORMATION: synthetic peptide

<400> SEQUENCE: 30

Ala Met Ala Glu Val Gln Leu Val Glu Ser Gly Gly Gly Leu Val Lys
1               5                   10                  15
```

```
Pro Gly Gly Ser Leu Arg Leu Ser Cys Ala Ala Ser Gly Phe Thr Phe
        20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Gly Ser Arg Ser Ser Arg Trp Gly Gln
            100                 105                 110

Gly Thr Leu Val Thr Val Ser Arg Gly Gly Gly Gly Ser Gly Gly Gly
            115                 120                 125

Gly Ser Gly Gly Gly Gly Ser Ser Glu Leu Thr Gln Asp Pro Ala Val
        130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
        210                 215                 220

Asp Ser Ser Gly Asn His Val Val Phe Gly Gly Gly Thr Lys Leu Thr
225                 230                 235                 240

Val Leu Gly Ala Ala Ala
                245
```

```
<210> SEQ ID NO 31
<211> LENGTH: 245
<212> TYPE: PRT
<213> ORGANISM: Artificial Sequence
<220> FEATURE:
<223> OTHER INFORMATION: synthetic peptide

<400> SEQUENCE: 31
```

```
Ala Met Ala Glu Val Gln Leu Leu Glu Ser Gly Gly Gly Leu Val Gln
1                   5                   10                  15

Pro Gly Gly Ser Leu Arg Leu Ser Cys Ala Ala Ser Gly Phe Thr Phe
        20                  25                  30

Ser Ser Tyr Ala Met Ser Trp Val Arg Gln Ala Pro Gly Lys Gly Leu
        35                  40                  45

Glu Trp Val Ser Ala Ile Ser Gly Ser Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Gln Lys Lys Arg Pro Arg Phe Trp Gly Gln Gly
            100                 105                 110

Thr Leu Val Thr Val Ser Arg Gly Gly Gly Gly Ser Gly Gly Gly Gly
            115                 120                 125
```

-continued

```
Ser Gly Gly Gly Gly Ser Ser Glu Leu Thr Gln Asp Pro Ala Val Ser
    130             135                 140

Val Ala Leu Gly Gln Thr Val Arg Ile Thr Cys Gln Gly Asp Ser Leu
145             150                 155                 160

Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
        195                 200                 205

Gly Ala Gln Ala Glu Asp Glu Ala Asp Tyr Tyr Cys Asn Ser Arg Asp
    210                 215                 220

Ser Ser Gly Asn His Val Val Phe Gly Gly Gly Thr Lys Leu Thr Val
225                 230                 235                 240

Leu Gly Ala Ala Ala
            245
```

```
<210> SEQ ID NO 32
<211> LENGTH: 246
<212> TYPE: PRT
<213> ORGANISM: Artificial Sequence
<220> FEATURE:
<223> OTHER INFORMATION: synthetic peptide

<400> SEQUENCE: 32
```

```
Ala Met Ala Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Trp Met His Trp Val Arg Gln Ala Pro Gly Lys Gly Leu
        35                  40                  45

Val Trp Val Ser Arg Ile Asn Ser Asp Gly Ser Ser Thr Thr Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Arg Ala Glu Asp Thr Ala Val
            85                  90                  95

Tyr Tyr Cys Ala Arg Ser Gly Arg Lys Gly Arg Met Arg Trp Gly Gln
            100                 105                 110

Gly Thr Leu Val Thr Val Ser Arg Gly Gly Gly Gly Ser Gly Gly Gly
        115                 120                 125

Gly Ser Gly Gly Gly Gly Ser Ser Glu Leu Thr Gln Asp Pro Ala Val
    130                 135                 140

Ser Val Ala Leu Gly Gln Thr Val Arg Ile Thr Cys Gln Gly Asp Ser
145             150                 155                 160

Leu Arg Ser Tyr Tyr Ala Ser Trp Tyr Gln Gln Lys Pro Gly Gln Ala
            165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
        195                 200                 205

Thr Gly Ala Gln Ala Glu Asp Glu Ala Asp Tyr Tyr Cys Asn Ser Arg
    210                 215                 220

Asp Ser Ser Gly Asn His Val Val Phe Gly Gly Gly Thr Lys Leu Thr
225                 230                 235                 240
```

```
Val Leu Gly Ala Ala Ala
            245

<210> SEQ ID NO 33
<211> LENGTH: 245
<212> TYPE: PRT
<213> ORGANISM: Artificial Sequence
<220> FEATURE:
<223> OTHER INFORMATION: synthetic peptide

<400> SEQUENCE: 33

Ala Met Ala Glu Val Gln Leu Val Glu Ser Gly Gly Val Val Arg
1               5                   10                  15

Pro Gly Gly Ser Leu Arg Leu Ser Cys Ala Ala Ser Gly Phe Thr Phe
            20                  25                  30

Asp Asp Tyr Gly Met Ser Trp Val Arg Gln Ala Pro Gly Lys Gly Leu
        35                  40                  45

Glu Trp Val Ser Gly Ile Asn Trp Asn Gly Gly Ser Thr Gly Tyr Ala
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Arg Arg Arg Tyr Ala Leu Asp Tyr Trp Gly Gln Gly
            100                 105                 110

Thr Leu Val Thr Val Ser Arg Gly Gly Gly Gly Ser Gly Gly Gly Gly
            115                 120                 125

Ser Gly Gly Gly Gly Ser Ser Glu Leu Thr Gln Asp Pro Ala Val Ser
        130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
                165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
            195                 200                 205

Gly Ala Gln Ala Glu Asp Glu Ala Asp Tyr Tyr Cys Asn Ser Arg Asp
        210                 215                 220

Ser Ser Gly Asn His Val Val Phe Gly Gly Gly Thr Lys Leu Thr Val
225                 230                 235                 240

Leu Gly Ala Ala Ala
            245

<210> SEQ ID NO 34
<211> LENGTH: 250
<212> TYPE: PRT
<213> ORGANISM: Artificial Sequence
<220> FEATURE:
<223> OTHER INFORMATION: synthetic peptide

<400> SEQUENCE: 34

Ala Met Ala Gln Val Gln Leu Val Gln Ser Gly Ala Glu Val Lys Lys
1               5                   10                  15

Pro Gly Ala Ser Val Lys Val Ser Cys Lys Ala Ser Gly Tyr Thr Phe
            20                  25                  30

Thr Ser Tyr Tyr Met His Trp Val Arg Gln Ala Pro Gly Gln Gly Leu
        35                  40                  45
```

```
Glu Trp Met Gly Ile Ile Asn Pro Ser Gly Gly Ser Thr Ser Tyr Ala
    50              55              60
Gln Lys Phe Gln Gly Arg Val Thr Met Thr Arg Asp Thr Ser Thr Ser
65              70              75              80
Thr Val Tyr Met Glu Leu Ser Ser Leu Arg Ser Glu Asp Thr Ala Val
            85              90              95
Tyr Tyr Cys Ala Arg Ala Met Thr Gln Lys Lys Pro Arg Lys Leu Ser
            100             105             110
Leu Trp Gly Gln Gly Thr Leu Val Thr Val Ser Arg Gly Gly Gly Gly
            115             120             125
Ser Gly Gly Gly Gly Ser Gly Gly Gly Ser Ser Glu Leu Thr Gln
    130             135             140
Asp Pro Ala Val Ser Val Ala Leu Gly Gln Thr Val Arg Ile Thr Cys
145             150             155             160
Gln Gly Asp Ser Leu Arg Ser Tyr Tyr Ala Ser Trp Tyr Gln Gln Lys
            165             170             175
Pro Gly Gln Ala Pro Val Leu Val Ile Tyr Gly Lys Asn Asn Arg Pro
            180             185             190
Ser Gly Ile Pro Asp Arg Phe Ser Gly Ser Ser Ser Gly Asn Thr Ala
            195             200             205
Ser Leu Thr Ile Thr Gly Ala Gln Ala Glu Asp Glu Ala Asp Tyr Tyr
    210             215             220
Cys Asn Ser Arg Asp Ser Ser Gly Asn His Val Val Phe Gly Gly Gly
225             230             235             240
Thr Lys Leu Thr Val Leu Gly Ala Ala Ala
            245             250
```

```
<210> SEQ ID NO 35
<211> LENGTH: 250
<212> TYPE: PRT
<213> ORGANISM: Artificial Sequence
<220> FEATURE:
<223> OTHER INFORMATION: synthetic peptide

<400> SEQUENCE: 35
```

```
Ala Met Ala Gln Met Gln Leu Val Gln Ser Gly Ala Glu Val Lys Lys
1               5               10              15
Thr Gly Ser Ser Val Lys Val Ser Cys Lys Ala Ser Gly Tyr Thr Phe
            20              25              30
Thr Tyr Arg Tyr Leu His Trp Val Arg Gln Ala Pro Gly Gln Ala Leu
            35              40              45
Glu Trp Met Gly Trp Ile Thr Pro Phe Asn Gly Asn Thr Asn Tyr Ala
    50              55              60
Gln Lys Phe Gln Asp Arg Val Thr Ile Thr Arg Asp Arg Ser Met Ser
65              70              75              80
Thr Ala Tyr Met Glu Leu Ser Ser Leu Arg Ser Glu Asp Thr Ala Met
            85              90              95
Tyr Tyr Cys Ala Arg Ser Gly Arg Lys Tyr Phe Arg Ala Arg Asp Met
            100             105             110
Asn Trp Gly Gln Gly Thr Leu Val Thr Val Ser Arg Gly Gly Gly Gly
            115             120             125
Ser Gly Gly Gly Gly Ser Gly Gly Gly Gly Ser Ser Glu Leu Thr Gln
    130             135             140
Asp Pro Ala Val Ser Val Ala Leu Gly Gln Thr Val Arg Ile Thr Cys
145             150             155             160
```

```
Gln Gly Asp Ser Leu Arg Ser Tyr Tyr Ala Ser Trp Tyr Gln Gln Lys
            165                 170                 175

Pro Gly Gln Ala Pro Val Leu Val Ile Tyr Gly Lys Asn Asn Arg Pro
            180                 185                 190

Ser Gly Ile Pro Asp Arg Phe Ser Gly Ser Ser Ser Gly Asn Thr Ala
            195                 200                 205

Ser Leu Thr Ile Thr Gly Ala Gln Ala Glu Asp Glu Ala Asp Tyr Tyr
    210                 215                 220

Cys Asn Ser Arg Asp Ser Ser Gly Asn His Val Val Phe Gly Gly Gly
225                 230                 235                 240

Thr Lys Leu Thr Val Leu Gly Ala Ala Ala
                245                 250

<210> SEQ ID NO 36
<211> LENGTH: 245
<212> TYPE: PRT
<213> ORGANISM: Artificial Sequence
<220> FEATURE:
<223> OTHER INFORMATION: synthetic peptide

<400> SEQUENCE: 36

Ala Met Ala Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Trp Met His Trp Val Arg Gln Ala Pro Gly Lys Gly Leu
            35                  40                  45

Val Trp Val Ser Arg Ile Asn Ser Asp Gly Ser Ser Thr Thr Tyr Ala
    50                  55                  60

Asp Ser Val Lys Gly Arg Phe Thr Ile Ser Arg Asp Asn Ala Lys Asn
65                  70                  75                  80

Thr Leu Tyr Leu Gln Met Asn Ser Leu Arg Ala Glu Asp Thr Ala Val
            85                  90                  95

Tyr Tyr Cys Ala Arg Leu Lys Gln Gln Gly Ile Ser Trp Gly Gln Gly
            100                 105                 110

Thr Leu Val Thr Val Ser Arg Gly Gly Gly Ser Gly Gly Gly Gly
            115                 120                 125

Ser Gly Gly Gly Gly Ser Ser Glu Leu Thr Gln Asp Pro Ala Val Ser
            130                 135                 140

Val Ala Leu Gly Gln Thr Val Arg Ile Thr Cys Gln Gly Asp Ser Leu
145                 150                 155                 160

Arg Ser Tyr Tyr Ala Ser Trp Tyr Gln Gln Lys Pro Gly Gln Ala Pro
            165                 170                 175

Val Leu Val Ile Tyr Gly Lys Asn Asn Arg Pro Ser Gly Ile Pro Asp
            180                 185                 190

Arg Phe Ser Gly Ser Ser Ser Gly Asn Thr Ala Ser Leu Thr Ile Thr
            195                 200                 205

Gly Ala Gln Ala Glu Asp Glu Ala Asp Tyr Tyr Cys Asn Ser Arg Asp
    210                 215                 220

Ser Ser Gly Asn His Val Val Phe Gly Gly Gly Thr Lys Leu Thr Val
225                 230                 235                 240

Leu Gly Ala Ala Ala
                245

<210> SEQ ID NO 37
```

<211> LENGTH: 246
<212> TYPE: PRT
<213> ORGANISM: Artificial Sequence
<220> FEATURE:
<223> OTHER INFORMATION: synthetic peptide

<400> SEQUENCE: 37

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Trp Arg Asn Asp Arg Gln Trp Gly Gln
            100                 105                 110

Gly Thr Leu Val Thr Val Ser Arg Gly Gly Gly Gly Ser Gly Gly Gly
            115                 120                 125

Gly Ser Gly Gly Gly Gly Ser Ser Glu Leu Thr Gln Asp Pro Ala Val
        130                 135                 140

Ser Val Ala Leu Gly Gln Thr Val Arg Ile Thr Cys Gln Gly Asp Ser
145                 150                 155                 160

Leu Arg Ser Tyr Tyr Ala Ser Trp Tyr Gln Gln Lys Pro Gly Gln Ala
                165                 170                 175

Pro Val Leu Val Ile Tyr Gly Lys Asn Asn Arg Pro Ser Gly Ile Pro
            180                 185                 190

Asp Arg Phe Ser Gly Ser Ser Ser Gly Asn Thr Ala Ser Leu Thr Ile
            195                 200                 205

Thr Gly Ala Gln Ala Glu Asp Glu Ala Asp Tyr Tyr Cys Asn Ser Arg
    210                 215                 220

Asp Ser Ser Gly Asn His Val Val Phe Gly Gly Gly Thr Lys Leu Thr
225                 230                 235                 240

Val Leu Gly Ala Ala Ala
                245
```

<210> SEQ ID NO 38
<211> LENGTH: 243
<212> TYPE: PRT
<213> ORGANISM: Artificial Sequence
<220> FEATURE:
<223> OTHER INFORMATION: synthetic peptide

<400> SEQUENCE: 38

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
```

```
65                    70                    75                    80

Met Glu Leu Ser Ser Leu Arg Ser Glu Asp Thr Ala Val Tyr Tyr Cys
             85                    90                    95

Ala Arg Gly Ile Lys His Arg His Thr Gln Trp Gly Gln Gly Thr Leu
            100                   105                   110

Val Thr Val Ser Arg Gly Gly Gly Ser Gly Gly Gly Gly Ser Gly
            115                   120                   125

Gly Gly Gly Ser Ser Glu Leu Thr Gln Asp Pro Ala Val Ser Val Ala
        130                   135                   140

Leu Gly Gln Thr Val Arg Ile Thr Cys Gln Gly Asp Ser Leu Arg Ser
145                   150                   155                   160

Tyr Tyr Ala Ser Trp Tyr Gln Gln Lys Pro Gly Gln Ala Pro Val Leu
                  165                   170                   175

Val Ile Tyr Gly Lys Asn Asn Arg Pro Ser Gly Ile Pro Asp Arg Phe
            180                   185                   190

Ser Gly Ser Ser Ser Gly Asn Thr Ala Ser Leu Thr Ile Thr Gly Ala
            195                   200                   205

Gln Ala Glu Asp Glu Ala Asp Tyr Tyr Cys Asn Ser Arg Asp Ser Ser
        210                   215                   220

Gly Asn His Val Val Phe Gly Gly Gly Thr Lys Leu Thr Val Leu Gly
225                   230                   235                   240

Ala Ala Ala

<210> SEQ ID NO 39
<211> LENGTH: 241
<212> TYPE: PRT
<213> ORGANISM: Artificial Sequence
<220> FEATURE:
<223> OTHER INFORMATION: synthetic peptide

<400> SEQUENCE: 39

Gln Val Gln Leu Val Gln Ser Gly Ala Glu Val Lys Lys Pro Gly Ala
1                 5                    10                    15

Ser Val Lys Val Ser Cys Lys Ala Ser Gly Tyr Thr Phe Thr Ser Tyr
            20                    25                    30

Tyr Met His Trp Val Arg Gln Ala Pro Gly Gln Gly Leu Glu Trp Met
        35                    40                    45

Gly Ile Ile Asn Pro Ser Gly Gly Ser Thr Ser Tyr Ala Gln Lys Phe
        50                    55                    60

Gln Gly Arg Val Thr Met Thr Arg Asp Thr Ser Thr Ser Thr Val Tyr
65                    70                    75                    80

Met Glu Leu Ser Ser Leu Arg Ser Glu Asp Thr Ala Val Tyr Tyr Cys
             85                    90                    95

Ala Arg Ala Lys Arg Leu Asp Trp Trp Gly Gln Gly Thr Leu Val Thr
            100                   105                   110

Val Ser Arg Gly Gly Gly Gly Ser Gly Gly Gly Gly Ser Gly Gly Gly
            115                   120                   125

Gly Ser Ser Glu Leu Thr Gln Asp Pro Ala Val Ser Val Ala Leu Gly
        130                   135                   140

Gln Thr Val Arg Ile Thr Cys Gln Gly Asp Ser Leu Arg Ser Tyr Tyr
145                   150                   155                   160

Ala Ser Trp Tyr Gln Gln Lys Pro Gly Gln Ala Pro Val Leu Val Ile
                  165                   170                   175

Tyr Gly Lys Asn Asn Arg Pro Ser Gly Ile Pro Asp Arg Phe Ser Gly
            180                   185                   190
```

-continued

```
Ser Ser Ser Gly Asn Thr Ala Ser Leu Thr Ile Thr Gly Ala Gln Ala
        195             200             205

Glu Asp Glu Ala Asp Tyr Tyr Cys Asn Ser Arg Asp Ser Ser Gly Asn
    210             215             220

His Val Val Phe Gly Gly Gly Thr Lys Leu Thr Val Leu Gly Ala Ala
225             230             235             240

Ala

<210> SEQ ID NO 40
<211> LENGTH: 242
<212> TYPE: PRT
<213> ORGANISM: Artificial Sequence
<220> FEATURE:
<223> OTHER INFORMATION: synthetic peptide

<400> SEQUENCE: 40

Gln Val Gln Leu Val Glu Ser Gly Gly Gly Val Val Gln Pro Gly Arg
1               5               10              15

Ser Leu Arg Leu Ser Cys Ala Ala Ser Gly Phe Thr Phe Ser Ser Tyr
        20              25              30

Ala Met His Trp Val Arg Gln Ala Pro Gly Lys Gly Leu Glu Trp Val
        35              40              45

Ala Val Ile Ser Tyr Asp Gly Ser Asn Lys Tyr Tyr Ala Asp Ser Val
    50              55              60

Lys Gly Arg Phe Thr Ile Ser Arg Asp Asn Ser Lys Asn Thr Leu Tyr
65              70              75              80

Leu Gln Met Asn Ser Leu Arg Ala Glu Asp Thr Ala Val Tyr Tyr Cys
            85              90              95

Ala Arg Met Lys Thr Arg Leu Asp Val Trp Gly Gln Gly Thr Leu Val
            100             105             110

Thr Val Ser Arg Gly Gly Gly Gly Ser Gly Gly Gly Gly Ser Gly Gly
        115             120             125

Gly Gly Ser Ser Glu Leu Thr Gln Asp Pro Ala Val Ser Val Ala Leu
        130             135             140

Gly Gln Thr Val Arg Ile Thr Cys Gln Gly Asp Ser Leu Arg Ser Tyr
145             150             155             160

Tyr Ala Ser Trp Tyr Gln Gln Lys Pro Gly Gln Ala Pro Val Leu Val
            165             170             175

Ile Tyr Gly Lys Asn Asn Arg Pro Ser Gly Ile Pro Asp Arg Phe Ser
            180             185             190

Gly Ser Ser Ser Gly Asn Thr Ala Ser Leu Thr Ile Thr Gly Ala Gln
        195             200             205

Ala Glu Asp Glu Ala Asp Tyr Tyr Cys Asn Ser Arg Asp Ser Ser Gly
    210             215             220

Asn His Val Val Phe Gly Gly Gly Thr Lys Leu Thr Val Leu Gly Ala
225             230             235             240

Ala Ala

<210> SEQ ID NO 41
<211> LENGTH: 241
<212> TYPE: PRT
<213> ORGANISM: Artificial Sequence
<220> FEATURE:
<223> OTHER INFORMATION: synthetic peptide

<400> SEQUENCE: 41
```

-continued

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
            35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Lys Gln Arg Tyr Ser Trp Gly Gln Gly Thr Leu Val Thr
            100                 105                 110

Val Ser Arg Gly Gly Gly Gly Ser Gly Gly Gly Gly Ser Gly Gly Gly
            115                 120                 125

Gly Ser Ser Glu Leu Thr Gln Asp Pro Ala Val Ser Val Ala Leu Gly
    130                 135                 140

Gln Thr Val Arg Ile Thr Cys Gln Gly Asp Ser Leu Arg Ser Tyr Tyr
145                 150                 155                 160

Ala Ser Trp Tyr Gln Gln Lys Pro Gly Gln Ala Pro Val Leu Val Ile
            165                 170                 175

Tyr Gly Lys Asn Asn Arg Pro Ser Gly Ile Pro Asp Arg Phe Ser Gly
            180                 185                 190

Ser Ser Ser Gly Asn Thr Ala Ser Leu Thr Ile Thr Gly Ala Gln Ala
            195                 200                 205

Glu Asp Glu Ala Asp Tyr Tyr Cys Asn Ser Arg Asp Ser Ser Gly Asn
    210                 215                 220

His Val Val Phe Gly Gly Gly Thr Lys Leu Thr Val Leu Gly Ala Ala
225                 230                 235                 240

Ala
```

```
<210> SEQ ID NO 42
<211> LENGTH: 244
<212> TYPE: PRT
<213> ORGANISM: Artificial Sequence
<220> FEATURE:
<223> OTHER INFORMATION: synthetic peptide

<400> SEQUENCE: 42
```

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Gly Arg Trp Thr Gln Met Thr Trp Gly Gln Gly Thr
            100                 105                 110

Leu Val Thr Val Ser Arg Gly Gly Gly Gly Ser Gly Gly Gly Gly Ser
```

-continued

```
              115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
              165                 170                 175

Leu Val Ile Tyr Gly Lys Asn Asn Arg Pro Ser Gly Ile Pro Asp Arg
              180                 185                 190

Phe Ser Gly Ser Ser Ser Gly Asn Thr Ala Ser Leu Thr Ile Thr Gly
              195                 200                 205

Ala Gln Ala Glu Asp Glu Ala Asp Tyr Tyr Cys Asn Ser Arg Asp Ser
    210                 215                 220

Ser Gly Asn His Val Val Phe Gly Gly Gly Thr Lys Leu Thr Val Leu
225                 230                 235                 240

Gly Ala Ala Ala
```

```
<210> SEQ ID NO 43
<211> LENGTH: 11
<212> TYPE: PRT
<213> ORGANISM: Artificial Sequence
<220> FEATURE:
<223> OTHER INFORMATION: synthetic peptide

<400> SEQUENCE: 43

Ser Leu Arg Met Asn Gly Trp Arg Ala His Gln
1               5                   10
```

```
<210> SEQ ID NO 44
<211> LENGTH: 7
<212> TYPE: PRT
<213> ORGANISM: Artificial Sequence
<220> FEATURE:
<223> OTHER INFORMATION: synthetic peptide

<400> SEQUENCE: 44

Gly Lys Met Lys Leu Asn Arg
1               5
```

```
<210> SEQ ID NO 45
<211> LENGTH: 6
<212> TYPE: PRT
<213> ORGANISM: Artificial Sequence
<220> FEATURE:
<223> OTHER INFORMATION: synthetic peptide

<400> SEQUENCE: 45

Gly Tyr Arg Pro Arg Phe
1               5
```

```
<210> SEQ ID NO 46
<211> LENGTH: 12
<212> TYPE: PRT
<213> ORGANISM: Artificial Sequence
<220> FEATURE:
<223> OTHER INFORMATION: synthetic peptide

<400> SEQUENCE: 46

Ser Ile Ser Met Asn Gly Val Gly Val Arg Ile Gln
1               5                   10
```

```
<210> SEQ ID NO 47
```

```
<211> LENGTH: 7
<212> TYPE: PRT
<213> ORGANISM: Artificial Sequence
<220> FEATURE:
<223> OTHER INFORMATION: synthetic peptide

<400> SEQUENCE: 47

Gly Arg Thr Val Gly Arg Asn
1               5

<210> SEQ ID NO 48
<211> LENGTH: 12
<212> TYPE: PRT
<213> ORGANISM: Artificial Sequence
<220> FEATURE:
<223> OTHER INFORMATION: synthetic peptide

<400> SEQUENCE: 48

Asp Arg Arg Asn Thr Gln Lys Thr Arg Tyr Arg Thr
1               5                   10

<210> SEQ ID NO 49
<211> LENGTH: 12
<212> TYPE: PRT
<213> ORGANISM: Artificial Sequence
<220> FEATURE:
<223> OTHER INFORMATION: synthetic peptide

<400> SEQUENCE: 49

Ser Gly Arg Gln Ala Arg Gln Gly Arg Phe Pro Lys
1               5                   10

<210> SEQ ID NO 50
<211> LENGTH: 8
<212> TYPE: PRT
<213> ORGANISM: Artificial Sequence
<220> FEATURE:
<223> OTHER INFORMATION: synthetic peptide

<400> SEQUENCE: 50

Gly Gly Thr Thr Arg Ile Arg Lys
1               5

<210> SEQ ID NO 51
<211> LENGTH: 8
<212> TYPE: PRT
<213> ORGANISM: Artificial Sequence
<220> FEATURE:
<223> OTHER INFORMATION: synthetic peptide

<400> SEQUENCE: 51

Gly Thr Lys Leu Lys Met Thr Lys
1               5

<210> SEQ ID NO 52
<211> LENGTH: 7
<212> TYPE: PRT
<213> ORGANISM: Artificial Sequence
<220> FEATURE:
<223> OTHER INFORMATION: synthetic peptide

<400> SEQUENCE: 52

Glu Arg Asn Thr Ile Arg Arg
1               5

<210> SEQ ID NO 53
<211> LENGTH: 8
```

```
<212> TYPE: PRT
<213> ORGANISM: Artificial Sequence
<220> FEATURE:
<223> OTHER INFORMATION: synthetic peptide

<400> SEQUENCE: 53

Gly Arg Leu His Leu Pro Arg Lys
1               5

<210> SEQ ID NO 54
<211> LENGTH: 10
<212> TYPE: PRT
<213> ORGANISM: Artificial Sequence
<220> FEATURE:
<223> OTHER INFORMATION: synthetic peptide

<400> SEQUENCE: 54

Ser Ser Ser Arg His His Arg Leu His Arg
1               5                   10

<210> SEQ ID NO 55
<211> LENGTH: 12
<212> TYPE: PRT
<213> ORGANISM: Artificial Sequence
<220> FEATURE:
<223> OTHER INFORMATION: synthetic peptide

<400> SEQUENCE: 55

Gln Arg Trp Lys Pro Ala Val Thr Pro Lys Leu Val
1               5                   10

<210> SEQ ID NO 56
<211> LENGTH: 12
<212> TYPE: PRT
<213> ORGANISM: Artificial Sequence
<220> FEATURE:
<223> OTHER INFORMATION: synthetic peptide

<400> SEQUENCE: 56

Ala Arg Met Thr Gly His Val Arg Asn Val Met Ile
1               5                   10

<210> SEQ ID NO 57
<211> LENGTH: 11
<212> TYPE: PRT
<213> ORGANISM: Artificial Sequence
<220> FEATURE:
<223> OTHER INFORMATION: synthetic peptide

<400> SEQUENCE: 57

Pro Val Ser His Arg Lys Trp Arg Val Thr Val
1               5                   10

<210> SEQ ID NO 58
<211> LENGTH: 8
<212> TYPE: PRT
<213> ORGANISM: Artificial Sequence
<220> FEATURE:
<223> OTHER INFORMATION: synthetic peptide

<400> SEQUENCE: 58

Gly Arg Arg His Lys Leu Ile Arg
1               5

<210> SEQ ID NO 59
<211> LENGTH: 9
<212> TYPE: PRT
```

```
<213> ORGANISM: Artificial Sequence
<220> FEATURE:
<223> OTHER INFORMATION: synthetic peptide

<400> SEQUENCE: 59

Leu Arg Gly Thr Lys Met Phe Arg His
1               5

<210> SEQ ID NO 60
<211> LENGTH: 11
<212> TYPE: PRT
<213> ORGANISM: Artificial Sequence
<220> FEATURE:
<223> OTHER INFORMATION: synthetic peptide

<400> SEQUENCE: 60

Ser Arg Lys Thr Pro Lys Pro Phe Met Arg Lys
1               5                   10

<210> SEQ ID NO 61
<211> LENGTH: 6
<212> TYPE: PRT
<213> ORGANISM: Artificial Sequence
<220> FEATURE:
<223> OTHER INFORMATION: synthetic peptide

<400> SEQUENCE: 61

Gly Ala Arg Leu Lys Arg
1               5

<210> SEQ ID NO 62
<211> LENGTH: 7
<212> TYPE: PRT
<213> ORGANISM: Artificial Sequence
<220> FEATURE:
<223> OTHER INFORMATION: synthetic peptide

<400> SEQUENCE: 62

Gly Lys Val Lys Leu Pro Asn
1               5

<210> SEQ ID NO 63
<211> LENGTH: 7
<212> TYPE: PRT
<213> ORGANISM: Artificial Sequence
<220> FEATURE:
<223> OTHER INFORMATION: synthetic peptide

<400> SEQUENCE: 63

Gly Thr Lys Lys Leu Gly Lys
1               5

<210> SEQ ID NO 64
<211> LENGTH: 6
<212> TYPE: PRT
<213> ORGANISM: Artificial Sequence
<220> FEATURE:
<223> OTHER INFORMATION: synthetic peptide

<400> SEQUENCE: 64

Gly Met Arg Pro Arg Leu
1               5

<210> SEQ ID NO 65
<211> LENGTH: 11
<212> TYPE: PRT
<213> ORGANISM: Artificial Sequence
```

<220> FEATURE:
<223> OTHER INFORMATION: synthetic peptide

<400> SEQUENCE: 65

Ser Arg Lys Thr Arg Lys Pro Phe Met Arg Lys
1               5                   10

<210> SEQ ID NO 66
<211> LENGTH: 7
<212> TYPE: PRT
<213> ORGANISM: Artificial Sequence
<220> FEATURE:
<223> OTHER INFORMATION: synthetic peptide

<400> SEQUENCE: 66

Tyr Tyr His Tyr Lys Val Asn
1               5

<210> SEQ ID NO 67
<211> LENGTH: 5
<212> TYPE: PRT
<213> ORGANISM: Artificial Sequence
<220> FEATURE:
<223> OTHER INFORMATION: synthetic peptide

<400> SEQUENCE: 67

Trp Val Thr Glu Pro
1               5

<210> SEQ ID NO 68
<211> LENGTH: 6
<212> TYPE: PRT
<213> ORGANISM: Artificial Sequence
<220> FEATURE:
<223> OTHER INFORMATION: synthetic peptide

<400> SEQUENCE: 68

Gly Arg Arg Leu Lys Asp
1               5

<210> SEQ ID NO 69
<211> LENGTH: 6
<212> TYPE: PRT
<213> ORGANISM: Artificial Sequence
<220> FEATURE:
<223> OTHER INFORMATION: synthetic peptide

<400> SEQUENCE: 69

Gly Met Arg Pro Arg Leu
1               5

<210> SEQ ID NO 70
<211> LENGTH: 11
<212> TYPE: PRT
<213> ORGANISM: Artificial Sequence
<220> FEATURE:
<223> OTHER INFORMATION: synthetic peptide

<400> SEQUENCE: 70

Ser Leu Arg Met Asn Gly Cys Gly Ala His Gln
1               5                   10

<210> SEQ ID NO 71
<211> LENGTH: 11
<212> TYPE: PRT
<213> ORGANISM: Artificial Sequence
<220> FEATURE:

<223> OTHER INFORMATION: synthetic peptide

<400> SEQUENCE: 71

His Ala Pro Leu Arg Asn Thr Arg Thr Asn Thr
1               5                   10

<210> SEQ ID NO 72
<211> LENGTH: 6
<212> TYPE: PRT
<213> ORGANISM: Artificial Sequence
<220> FEATURE:
<223> OTHER INFORMATION: synthetic peptide

<400> SEQUENCE: 72

Gly Ser Arg Ser Ser Arg
1               5

<210> SEQ ID NO 73
<211> LENGTH: 7
<212> TYPE: PRT
<213> ORGANISM: Artificial Sequence
<220> FEATURE:
<223> OTHER INFORMATION: synthetic peptide

<400> SEQUENCE: 73

Gln Lys Lys Arg Pro Arg Phe
1               5

<210> SEQ ID NO 74
<211> LENGTH: 8
<212> TYPE: PRT
<213> ORGANISM: Artificial Sequence
<220> FEATURE:
<223> OTHER INFORMATION: synthetic peptide

<400> SEQUENCE: 74

Ser Gly Arg Lys Gly Arg Met Arg
1               5

<210> SEQ ID NO 75
<211> LENGTH: 7
<212> TYPE: PRT
<213> ORGANISM: Artificial Sequence
<220> FEATURE:
<223> OTHER INFORMATION: synthetic peptide

<400> SEQUENCE: 75

Arg Arg Tyr Ala Leu Asp Tyr
1               5

<210> SEQ ID NO 76
<211> LENGTH: 7
<212> TYPE: PRT
<213> ORGANISM: Artificial Sequence
<220> FEATURE:
<223> OTHER INFORMATION: synthetic peptide

<400> SEQUENCE: 76

Leu Lys Gln Gln Gly Ile Ser
1               5

<210> SEQ ID NO 77
<211> LENGTH: 12
<212> TYPE: PRT
<213> ORGANISM: Artificial Sequence
<220> FEATURE:
<223> OTHER INFORMATION: synthetic peptide

<400> SEQUENCE: 77

Ala Met Thr Gln Lys Lys Pro Arg Lys Leu Ser Leu
1               5                   10

<210> SEQ ID NO 78
<211> LENGTH: 12
<212> TYPE: PRT
<213> ORGANISM: Artificial Sequence
<220> FEATURE:
<223> OTHER INFORMATION: synthetic peptide

<400> SEQUENCE: 78

Ser Gly Arg Lys Tyr Phe Arg Ala Arg Asp Met Asn
1               5                   10

<210> SEQ ID NO 79
<211> LENGTH: 6
<212> TYPE: PRT
<213> ORGANISM: Artificial Sequence
<220> FEATURE:
<223> OTHER INFORMATION: synthetic peptide

<400> SEQUENCE: 79

Trp Arg Asn Asp Arg Gln
1               5

<210> SEQ ID NO 80
<211> LENGTH: 8
<212> TYPE: PRT
<213> ORGANISM: Artificial Sequence
<220> FEATURE:
<223> OTHER INFORMATION: synthetic peptide

<400> SEQUENCE: 80

Gly Ile Lys His Arg His Thr Gln
1               5

<210> SEQ ID NO 81
<211> LENGTH: 6
<212> TYPE: PRT
<213> ORGANISM: Artificial Sequence
<220> FEATURE:
<223> OTHER INFORMATION: synthetic peptide

<400> SEQUENCE: 81

Ala Lys Arg Leu Asp Trp
1               5

<210> SEQ ID NO 82
<211> LENGTH: 7
<212> TYPE: PRT
<213> ORGANISM: Artificial Sequence
<220> FEATURE:
<223> OTHER INFORMATION: synthetic peptide

<400> SEQUENCE: 82

Met Lys Thr Arg Leu Asp Val
1               5

<210> SEQ ID NO 83
<211> LENGTH: 6
<212> TYPE: PRT
<213> ORGANISM: Artificial Sequence
<220> FEATURE:
<223> OTHER INFORMATION: synthetic peptide

```
<400> SEQUENCE: 83

Gly Lys Gln Arg Tyr Ser
1               5

<210> SEQ ID NO 84
<211> LENGTH: 7
<212> TYPE: PRT
<213> ORGANISM: Artificial Sequence
<220> FEATURE:
<223> OTHER INFORMATION: synthetic peptide

<400> SEQUENCE: 84

Gly Arg Trp Thr Gln Met Thr
1               5

<210> SEQ ID NO 85
<211> LENGTH: 5
<212> TYPE: PRT
<213> ORGANISM: Artificial Sequence
<220> FEATURE:
<223> OTHER INFORMATION: CDR1H

<400> SEQUENCE: 85

Ser Tyr Ala Met Ser
1               5

<210> SEQ ID NO 86
<211> LENGTH: 17
<212> TYPE: PRT
<213> ORGANISM: Artificial Sequence
<220> FEATURE:
<223> OTHER INFORMATION: CDR2H

<400> SEQUENCE: 86

Ala Ile Ser Gly Ser Gly Gly Ser Thr Tyr Tyr Ala Asp Ser Val Lys
1               5                   10                  15

Gly

<210> SEQ ID NO 87
<211> LENGTH: 11
<212> TYPE: PRT
<213> ORGANISM: Artificial Sequence
<220> FEATURE:
<223> OTHER INFORMATION: CDR1L

<400> SEQUENCE: 87

Gln Gly Asp Ser Leu Arg Ser Tyr Tyr Ala Ser
1               5                   10

<210> SEQ ID NO 88
<211> LENGTH: 7
<212> TYPE: PRT
<213> ORGANISM: Artificial Sequence
<220> FEATURE:
<223> OTHER INFORMATION: CDR2L

<400> SEQUENCE: 88

Gly Lys Asn Asn Arg Pro Ser
1               5

<210> SEQ ID NO 89
<211> LENGTH: 11
<212> TYPE: PRT
<213> ORGANISM: Artificial Sequence
<220> FEATURE:
<223> OTHER INFORMATION: CRD3L
```

-continued

<400> SEQUENCE: 89

Asn Ser Arg Asp Ser Ser Gly Asn His Val Val
1               5                   10

<210> SEQ ID NO 90
<211> LENGTH: 5
<212> TYPE: PRT
<213> ORGANISM: Artificial Sequence
<220> FEATURE:
<223> OTHER INFORMATION: CDR1H

<400> SEQUENCE: 90

Asn Ala Trp Met Ser
1               5

<210> SEQ ID NO 91
<211> LENGTH: 19
<212> TYPE: PRT
<213> ORGANISM: Artificial Sequence
<220> FEATURE:
<223> OTHER INFORMATION: CDR2H

<400> SEQUENCE: 91

Arg Ile Lys Ser Lys Thr Asp Gly Gly Thr Thr Asp Tyr Ala Ala Pro
1               5                   10                  15

Val Lys Gly

<210> SEQ ID NO 92
<211> LENGTH: 5
<212> TYPE: PRT
<213> ORGANISM: Artificial Sequence
<220> FEATURE:
<223> OTHER INFORMATION: CDR1H

<400> SEQUENCE: 92

Ser Tyr Glu Met Asn
1               5

<210> SEQ ID NO 93
<211> LENGTH: 17
<212> TYPE: PRT
<213> ORGANISM: Artificial Sequence
<220> FEATURE:
<223> OTHER INFORMATION: CDR2H

<400> SEQUENCE: 93

Tyr Ile Ser Ser Ser Gly Ser Thr Ile Tyr Tyr Ala Asp Ser Val Lys
1               5                   10                  15

Gly

<210> SEQ ID NO 94
<211> LENGTH: 5
<212> TYPE: PRT
<213> ORGANISM: Artificial Sequence
<220> FEATURE:
<223> OTHER INFORMATION: CDR1H

<400> SEQUENCE: 94

Asp Tyr Gly Met Ser
1               5

<210> SEQ ID NO 95
<211> LENGTH: 17
<212> TYPE: PRT

<213> ORGANISM: Artificial Sequence
<220> FEATURE:
<223> OTHER INFORMATION: CDR2H

<400> SEQUENCE: 95

Gly Ile Asn Trp Asn Gly Gly Ser Thr Gly Tyr Ala Asp Ser Val Lys
1               5                   10                  15

Gly

<210> SEQ ID NO 96
<211> LENGTH: 121
<212> TYPE: PRT
<213> ORGANISM: Artificial Sequence
<220> FEATURE:
<223> OTHER INFORMATION: VH

<400> SEQUENCE: 96

Ala Met Ala Glu Val Gln Leu Leu Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Ala Ile Ser Gly Ser Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Ser Leu Arg Met Asn Gly Trp Arg Ala His Gln
            100                 105                 110

Trp Gly Gln Gly Thr Leu Val Thr Val
        115                 120

<210> SEQ ID NO 97
<211> LENGTH: 112
<212> TYPE: PRT
<213> ORGANISM: Artificial Sequence
<220> FEATURE:
<223> OTHER INFORMATION: VL

<400> SEQUENCE: 97

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu Gly Ala Ala Ala
            100                 105                 110

<210> SEQ ID NO 98
<211> LENGTH: 122

<212> TYPE: PRT
<213> ORGANISM: Artificial Sequence
<220> FEATURE:
<223> OTHER INFORMATION: VH

<400> SEQUENCE: 98

```
Ala Met Ala Glu Val Gln Leu Leu Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Ala Met Ser Trp Val Arg Gln Ala Pro Gly Lys Gly Leu
        35                  40                  45

Glu Trp Val Ser Ala Ile Ser Gly Ser Gly Gly Ser Thr Tyr Tyr Ala
    50                  55                  60

Asp Ser Val Lys Gly Arg Phe Thr Ile Ser Arg Asp Asn Ser Lys Asn
65                  70                  75                  80

Thr Leu Tyr Leu Gln Met Asn Ser Leu Arg Ala Glu Asp Thr Ala Val
                85                  90                  95

Tyr Tyr Cys Ala Arg Ser Ile Ser Met Asn Gly Val Gly Val Arg Ile
            100                 105                 110

Gln Trp Gly Gln Gly Thr Leu Val Thr Val
            115                 120
```

<210> SEQ ID NO 99
<211> LENGTH: 124
<212> TYPE: PRT
<213> ORGANISM: Artificial Sequence
<220> FEATURE:
<223> OTHER INFORMATION: VH

<400> SEQUENCE: 99

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Ser Gly Arg Gln Ala Arg Gln Gly Arg
            100                 105                 110

Phe Pro Lys Trp Gly Gln Gly Thr Leu Val Thr Val
            115                 120
```

<210> SEQ ID NO 100
<211> LENGTH: 121
<212> TYPE: PRT
<213> ORGANISM: Artificial Sequence
<220> FEATURE:
<223> OTHER INFORMATION: VH

<400> SEQUENCE: 100

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
```

```
                20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Leu Arg Gly Thr Lys Met Phe Arg His
                100                 105                 110

Trp Gly Gln Gly Thr Leu Val Thr Val
        115                 120
```

<210> SEQ ID NO 101
<211> LENGTH: 119
<212> TYPE: PRT
<213> ORGANISM: Artificial Sequence
<220> FEATURE:
<223> OTHER INFORMATION: VH

<400> SEQUENCE: 101

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
                20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Gly Lys Val Lys Leu Pro Asn Trp Gly
                100                 105                 110

Gln Gly Thr Leu Val Thr Val
        115
```

<210> SEQ ID NO 102
<211> LENGTH: 118
<212> TYPE: PRT
<213> ORGANISM: Artificial Sequence
<220> FEATURE:
<223> OTHER INFORMATION: VH

<400> SEQUENCE: 102

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
                20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80
```

-continued

```
Lys Asn Thr Leu Tyr Leu Gln Met Asn Ser Leu Lys Thr Glu Asp Thr
            85                  90                  95

Ala Val Tyr Tyr Cys Ala Arg Gly Met Arg Pro Arg Leu Trp Gly Gln
            100                 105                 110

Gly Thr Leu Val Thr Val
        115
```

```
<210> SEQ ID NO 103
<211> LENGTH: 118
<212> TYPE: PRT
<213> ORGANISM: Artificial Sequence
<220> FEATURE:
<223> OTHER INFORMATION: VH

<400> SEQUENCE: 103
```

```
Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
            35                  40                  45

Glu Trp Val Gly Arg Ile Lys Ser Lys Thr Asp Gly Gly Thr Thr Asp
        50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
            85                  90                  95

Ala Val Tyr Tyr Cys Ala Arg Gly Arg Arg Leu Lys Asp Trp Gly Gln
            100                 105                 110

Gly Thr Leu Val Thr Val
        115
```

```
<210> SEQ ID NO 104
<211> LENGTH: 116
<212> TYPE: PRT
<213> ORGANISM: Artificial Sequence
<220> FEATURE:
<223> OTHER INFORMATION: VH

<400> SEQUENCE: 104
```

```
Ala Met Ala Glu Val Gln Leu Val Glu Ser Gly Gly Gly Leu Val Gln
1               5                   10                  15

Pro Gly Gly Ser Leu Arg Leu Ser Cys Ala Ala Ser Gly Phe Thr Phe
            20                  25                  30

Ser Ser Tyr Glu Met Asn Trp Val Arg Gln Ala Pro Gly Lys Gly Leu
            35                  40                  45

Glu Trp Val Ser Tyr Ile Ser Ser Ser Gly Ser Thr Ile Tyr Tyr Ala
        50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
            85                  90                  95

Tyr Tyr Cys Ala Arg Gly Met Arg Pro Arg Leu Trp Gly Gln Gly Thr
            100                 105                 110

Leu Val Thr Val
        115
```

```
<210> SEQ ID NO 105
```

```
<211> LENGTH: 123
<212> TYPE: PRT
<213> ORGANISM: Artificial Sequence
<220> FEATURE:
<223> OTHER INFORMATION: VH

<400> SEQUENCE: 105

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg His Ala Pro Leu Arg Asn Thr Arg Thr
            100                 105                 110

Asn Thr Trp Gly Gln Gly Thr Leu Val Thr Val
        115                 120

<210> SEQ ID NO 106
<211> LENGTH: 118
<212> TYPE: PRT
<213> ORGANISM: Artificial Sequence
<220> FEATURE:
<223> OTHER INFORMATION: VH

<400> SEQUENCE: 106

Ala Met Ala Glu Val Gln Leu Val Glu Ser Gly Gly Gly Leu Val Lys
1               5                   10                  15

Pro Gly Gly Ser Leu Arg Leu Ser Cys Ala Ala Ser Gly Phe Thr Phe
            20                  25                  30

Ser Asn Ala Trp Met Ser Trp Val Arg Gln Ala Pro Gly Lys Gly Leu
        35                  40                  45

Glu Trp Val Gly Arg Ile Lys Ser Lys Thr Asp Gly Gly Thr Thr Asp
    50                  55                  60

Tyr Ala Ala Pro Val Lys Gly Arg Phe Thr Ile Ser Arg Asp Asp Ser
65                  70                  75                  80

Lys Asn Thr Leu Tyr Leu Gln Met Asn Ser Leu Lys Thr Glu Asp Thr
                85                  90                  95

Ala Val Tyr Tyr Cys Ala Arg Gly Ser Arg Ser Ser Arg Trp Gly Gln
            100                 105                 110

Gly Thr Leu Val Thr Val
        115

<210> SEQ ID NO 107
<211> LENGTH: 117
<212> TYPE: PRT
<213> ORGANISM: Artificial Sequence
<220> FEATURE:
<223> OTHER INFORMATION: VH

<400> SEQUENCE: 107

Ala Met Ala Glu Val Gln Leu Val Glu Ser Gly Gly Gly Val Val Arg
1               5                   10                  15
```

```
Pro Gly Gly Ser Leu Arg Leu Ser Cys Ala Ala Ser Gly Phe Thr Phe
            20                  25                  30

Asp Asp Tyr Gly Met Ser Trp Val Arg Gln Ala Pro Gly Lys Gly Leu
        35                  40                  45

Glu Trp Val Ser Gly Ile Asn Trp Asn Gly Gly Ser Thr Gly Tyr Ala
    50                  55                  60

Asp Ser Val Lys Gly Arg Phe Thr Ile Ser Arg Asp Asn Ala Lys Asn
65                  70                  75                  80

Ser Leu Tyr Leu Gln Met Asn Ser Leu Arg Ala Glu Asp Thr Ala Val
                85                  90                  95

Tyr Tyr Cys Ala Arg Arg Arg Tyr Ala Leu Asp Tyr Trp Gly Gln Gly
            100                 105                 110

Thr Leu Val Thr Val
        115

<210> SEQ ID NO 108
<211> LENGTH: 5
<212> TYPE: PRT
<213> ORGANISM: Artificial Sequence
<220> FEATURE:
<223> OTHER INFORMATION: CDR1H

<400> SEQUENCE: 108

Ser Asn Tyr Met Ser
1                5

<210> SEQ ID NO 109
<211> LENGTH: 16
<212> TYPE: PRT
<213> ORGANISM: Artificial Sequence
<220> FEATURE:
<223> OTHER INFORMATION: CDR2H

<400> SEQUENCE: 109

Val Ile Tyr Ser Gly Gly Ser Thr Tyr Tyr Ala Asp Ser Val Lys Gly
1                5                  10                  15

<210> SEQ ID NO 110
<211> LENGTH: 17
<212> TYPE: PRT
<213> ORGANISM: Artificial Sequence
<220> FEATURE:
<223> OTHER INFORMATION: CDR2H

<400> SEQUENCE: 110

Trp Ile Asn Pro Asn Ser Gly Gly Thr Asn Tyr Ala Gln Lys Phe Gln
1                5                  10                  15

Gly

<210> SEQ ID NO 111
<211> LENGTH: 16
<212> TYPE: PRT
<213> ORGANISM: Artificial Sequence
<220> FEATURE:
<223> OTHER INFORMATION: CDR2H

<400> SEQUENCE: 111

Ala Ile Gly Thr Gly Gly Gly Thr Tyr Tyr Ala Asp Ser Val Lys Gly
1                5                  10                  15

<210> SEQ ID NO 112
<211> LENGTH: 17
<212> TYPE: PRT
```

-continued

<213> ORGANISM: Artificial Sequence
<220> FEATURE:
<223> OTHER INFORMATION: CDR2H

<400> SEQUENCE: 112

Leu Val Asp Pro Glu Asp Gly Glu Thr Ile Tyr Ala Glu Lys Phe Gln
1               5                   10                  15

Gly

<210> SEQ ID NO 113
<211> LENGTH: 16
<212> TYPE: PRT
<213> ORGANISM: Artificial Sequence
<220> FEATURE:
<223> OTHER INFORMATION: CDR2H

<400> SEQUENCE: 113

Trp Ile Asn Pro Asn Ser Gly Gly Thr Asn Tyr Ala Gln Lys Phe Gln
1               5                   10                  15

<210> SEQ ID NO 114
<211> LENGTH: 17
<212> TYPE: PRT
<213> ORGANISM: Artificial Sequence
<220> FEATURE:
<223> OTHER INFORMATION: CDR2H

<400> SEQUENCE: 114

Trp Ile Asn Ala Gly Asn Gly Asn Thr Lys Tyr Ser Gln Lys Phe Gln
1               5                   10                  15

Gly

<210> SEQ ID NO 115
<211> LENGTH: 5
<212> TYPE: PRT
<213> ORGANISM: Artificial Sequence
<220> FEATURE:
<223> OTHER INFORMATION: CDR1H

<400> SEQUENCE: 115

Ser Tyr Ala Met His
1               5

<210> SEQ ID NO 116
<211> LENGTH: 16
<212> TYPE: PRT
<213> ORGANISM: Artificial Sequence
<220> FEATURE:
<223> OTHER INFORMATION: CDR2H

<400> SEQUENCE: 116

Tyr Ile Tyr Tyr Ser Gly Ser Thr Tyr Tyr Asn Pro Ser Leu Lys Ser
1               5                   10                  15

<210> SEQ ID NO 117
<211> LENGTH: 5
<212> TYPE: PRT
<213> ORGANISM: Artificial Sequence
<220> FEATURE:
<223> OTHER INFORMATION: CDR1H

<400> SEQUENCE: 117

Ser Tyr Trp Met His
1               5

-continued

```
<210> SEQ ID NO 118
<211> LENGTH: 5
<212> TYPE: PRT
<213> ORGANISM: Artificial Sequence
<220> FEATURE:
<223> OTHER INFORMATION: CDR1H

<400> SEQUENCE: 118

Asp Tyr Tyr Met His
1               5

<210> SEQ ID NO 119
<211> LENGTH: 5
<212> TYPE: PRT
<213> ORGANISM: Artificial Sequence
<220> FEATURE:
<223> OTHER INFORMATION: CDR1H

<400> SEQUENCE: 119

Gly Tyr Tyr Met His
1               5

<210> SEQ ID NO 120
<211> LENGTH: 7
<212> TYPE: PRT
<213> ORGANISM: Artificial Sequence
<220> FEATURE:
<223> OTHER INFORMATION: CDR1H

<400> SEQUENCE: 120

Ser Gly Gly Tyr Tyr Trp Ser
1               5

<210> SEQ ID NO 121
<211> LENGTH: 5
<212> TYPE: PRT
<213> ORGANISM: Artificial Sequence
<220> FEATURE:
<223> OTHER INFORMATION: CDR1H

<400> SEQUENCE: 121

Ser Tyr Tyr Met His
1               5

<210> SEQ ID NO 122
<211> LENGTH: 17
<212> TYPE: PRT
<213> ORGANISM: Artificial Sequence
<220> FEATURE:
<223> OTHER INFORMATION: CDR2H

<400> SEQUENCE: 122

Ile Ile Asn Pro Ser Gly Gly Ser Thr Ser Tyr Ala Gln Lys Phe Gln
1               5                   10                  15

Gly

<210> SEQ ID NO 123
<211> LENGTH: 17
<212> TYPE: PRT
<213> ORGANISM: Artificial Sequence
<220> FEATURE:
<223> OTHER INFORMATION: CDR2H

<400> SEQUENCE: 123

Trp Ile Thr Pro Phe Asn Gly Asn Thr Asn Tyr Ala Gln Lys Phe Gln
1               5                   10                  15
```

-continued

```
Asp

<210> SEQ ID NO 124
<211> LENGTH: 17
<212> TYPE: PRT
<213> ORGANISM: Artificial Sequence
<220> FEATURE:
<223> OTHER INFORMATION: CDR2H

<400> SEQUENCE: 124

Arg Ile Asn Ser Asp Gly Ser Ser Thr Thr Tyr Ala Asp Ser Val Lys
1               5                   10                  15

Gly

<210> SEQ ID NO 125
<211> LENGTH: 5
<212> TYPE: PRT
<213> ORGANISM: Artificial Sequence
<220> FEATURE:
<223> OTHER INFORMATION: CDR1H

<400> SEQUENCE: 125

Tyr Arg Tyr Leu His
1               5
```